US011352315B2

(12) United States Patent
Looper et al.

(10) Patent No.: US 11,352,315 B2
(45) Date of Patent: Jun. 7, 2022

(54) COMPOSITIONS AND METHODS COMPRISING A TRIARYL POLYAMINE

(71) Applicants: Curza Global, LLC, Provo, UT (US); University of Utah Research Foundation, Salt Lake City, UT (US)

(72) Inventors: Ryan E. Looper, Salt Lake City, UT (US); Dustin Williams, Bountiful, UT (US); Paul R. Sebahar, Sandy, UT (US); Travis J. Haussener, Salt Lake City, UT (US); Hariprasada R. Kanna Reddy, Salt Lake City, UT (US)

(73) Assignees: Curza Global, LLC, Provo, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/593,143

(22) Filed: Oct. 4, 2019

(65) Prior Publication Data
US 2020/0031757 A1 Jan. 30, 2020

Related U.S. Application Data

(63) Continuation of application No. PCT/US2018/026320, filed on Apr. 5, 2018.

(60) Provisional application No. 62/482,106, filed on Apr. 5, 2017.

(51) Int. Cl.
*C07C 211/27* (2006.01)
*A61P 17/02* (2006.01)

(52) U.S. Cl.
CPC ............ *C07C 211/27* (2013.01); *A61P 17/02* (2018.01)

(58) Field of Classification Search
CPC .................................................. C07C 211/27
See application file for complete search history.

(56) References Cited

U.S. PATENT DOCUMENTS

| 4,038,312 | A  | 7/1977  | Atkins          |
|-----------|----|---------|-----------------|
| 4,340,756 | A  | 7/1982  | Dybas et al.    |
| 4,505,861 | A  | 3/1985  | Bergeron, Jr.   |
| 4,522,811 | A  | 6/1985  | Eppstein et al. |
| 5,583,239 | A  | 12/1996 | Regen           |
| 6,077,954 | A  | 6/2000  | Cook et al.     |
| 6,149,822 | A  | 11/2000 | Fabri et al.    |
| 6,329,523 | B1 | 12/2001 | Cook et al.     |
| 6,395,189 | B1 | 5/2002  | Fabri et al.    |
| 6,555,228 | B2 | 4/2003  | Guritza         |
| 6,613,435 | B1 | 9/2003  | Guritza         |
| 6,982,351 | B2 | 1/2006  | Frydman et al.  |
| 7,425,579 | B2 | 9/2008  | Poulin et al.   |
| 8,853,278 | B1 | 10/2014 | Looper et al.   |
| 9,034,927 | B2 | 5/2015  | Williams et al. |
| 9,220,267 | B2 | 12/2015 | Williams et al. |
| 9,439,433 | B2 | 9/2016  | Looper et al.   |
| 9,839,219 | B2 | 12/2017 | Looper et al.   |
| 10,440,955 | B2 | 10/2019 | Looper et al.  |
| 2004/0209926 | A1 | 10/2004 | Burns et al.  |
| 2007/0208082 | A1 | 9/2007 | Woster et al.   |
| 2008/0199509 | A1 | 8/2008 | Nick et al.     |
| 2008/0274929 | A1 | 11/2008 | Whitekettle et al. |
| 2009/0124591 | A1 | 5/2009 | Diamond et al.  |
| 2010/0093973 | A1 | 4/2010 | Nakagawa et al. |
| 2012/0015865 | A1 | 1/2012 | Zelphati et al. |
| 2014/0350017 | A1 | 11/2014 | Williams et al. |
| 2015/0038512 | A1 | 2/2015 | Looper et al.   |
| 2015/0038705 | A1 | 2/2015 | Williams et al. |
| 2015/0274639 | A1 | 10/2015 | Williams et al. |

FOREIGN PATENT DOCUMENTS

| FR | 2 860 129 A1   | 1/2005  |
|----|----------------|---------|
| JP | 2005520821 A   | 7/2005  |
| JP | 2016526038 A   | 9/2016  |
| WO | 93/12097 A1    | 6/1993  |
| WO | 94/19311 A1    | 9/1994  |
| WO | 97/01360 A2    | 1/1997  |
| WO | 2004/030672 A1 | 4/2004  |
| WO | 2005/105729 A1 | 11/2005 |
| WO | 2007/071396 A2 | 6/2007  |
| WO | 2008/137195 A1 | 11/2008 |
| WO | 2010/010345 A2 | 1/2010  |
| WO | 2010/148390 A2 | 12/2010 |
| WO | 2012/151554 A1 | 11/2012 |
| WO | 2012/151555 A1 | 11/2012 |
| WO | 2013/072491 A1 | 5/2013  |
| WO | 2013/148230 A1 | 10/2013 |

(Continued)

OTHER PUBLICATIONS

Bolognesi, Maria et al. (J. Med. Chem. 2002, 45, 3286-3295).*
Bachrach et al., "Antibacterial Action of Oxidized Spermine," J. gen. Microbiol., 1964, vol. 37, pp. 195-204.
Barry et al., "Methods for Determining Bactericidal Activity of Antimicrobial Agents: Approved Guidelines," NCCLS, Sep. 1999, vol. 19(18), pp. 1-28.
Baxter et al., "Reductive Aminations of Carbonyl Compounds with Borohydride and Borane Reducing Agents," Org Reac, 2004, 1, 59.
Boncher et al., "Polyamine-Based Analogues as Biochemical Probes and Potential Therapeutics," Biochemical Society Transactions, 2007, 35(Part 2); 356-363.

(Continued)

*Primary Examiner* — Valerie Rodriguez-Garcia
(74) *Attorney, Agent, or Firm* — Kilpatrick Townsend & Stockton LLP

(57) ABSTRACT

Compounds, compositions, and methods comprising a polyamine compound are described, which may be used to kill, disperse, treat, or reduce biofilms, or to inhibit or substantially prevent biofilm formation. In some aspects, the present invention relates to polyamine compounds that have antimicrobial or dispersing activity against a variety of bacterial strains capable of forming biofilms. In some aspects, the present invention relates to compositions and methods comprising the polyamine compound. In some aspects, the compounds, compositions, and methods enhance wound healing.

20 Claims, 8 Drawing Sheets

(56) References Cited

FOREIGN PATENT DOCUMENTS

| WO | 2014/078801 A1 | 5/2014 |
| WO | 2014/190096 A1 | 11/2014 |
| WO | 2014/190097 A1 | 11/2014 |
| WO | 2017147335 A1 | 8/2017 |
| WO | WO2017/218922 | * 12/2017 |
| WO | 2018/187615 A1 | 10/2018 |

OTHER PUBLICATIONS

Bottcher et al., "Synthesis and Activity of Biomimetic Biofilm Disruptors," J. of the American Chem. Society, 2013, vol. 135, pp. 2927-2930.

Chinese Application No. 201480041542.1, First Office Action dated Nov. 7, 2016, 7 pages, English translation.

Company et al., "$O_2$ Chemistry of Dicopper Complexes with Alkyltriamine Ligands. Comparing Synergistic Effects on $O_2$ Binding," Inorganic Chemistry, 2006, 45(14), 5239-41.

Company et al., "$O_2$ Chemistry of Dicopper Complexes with Alkyltriamine Ligands. Comparing Synergistic Effects on $O_2$ Binding," Inorganic Chemistry, 2006, Supporting Information, 14 pages.

Database CAPLUS in STN, Acc. No. 1996:198207, Rehse et al., Archiv der Pharmazie (1996), 329(3), pp. 155-160 (abstract).

Database CAPLUS on STN, Acc. No. 2003:265709, Ambrosi et al., Polyhedron (2003), 22(8), pp. 1135-1146 (abstract).

Database CAPLUS on STN, Acc. No. 2006:525185, Company et al., Inorganic Chemistry (2006), 45(14), pp. 5239-5241 (abstract).

Database CAPLUS on STN, Acc. No. 2010:1600778, Phanstiel et al., WO2010/148390 A2, Dec. 23, 2010 (abstract).

De Almeida et al., "Synthesis and antitubercular activity of lipophilic moxifloxacin and gatifloxacin derivatives," Bioorganic and Medicinal Chemistry Letters, 2007, vol. 17, pp. 5661-5664.

Dietrich et al., "123. Synthesis and Protonation Features of 24-, 27- and 32-membered Macrocyclic Polyamines," Helvetica Chimica Acta, 1983, vol. 66, Fasc. 4,—Nr. 123.

Dou, D. et al., "Design and synthesis of inhibitors of noroviruses by scaffold hopping," Bioorganic & Medicinal Chemistry, Pergamon, GB, vol. 19, No. 19, Aug. 15, 2011, pp. 5749-5755.

European Application No. 14735722.2, Communication pursuant to Article 94(3) EPC, dated Feb. 28, 2019, 4 pages.

European Application No. 14735722.2, Communication pursuant to Article 94(3) EPC, dated Nov. 9, 2017, 4 pages.

European Application No. 14735722.2, Office Action dated Oct. 31, 2016, 5 pages.

Jayaraman et al., "Inhibiting sulfate-reducing bacteria in biofilms by expressing the antimicrobial peptides indolicidin and bactenecin," Journal of Industrial Microbiology & Biotechnology, 1999, vol. 22, pp. 167-175.

Joshi et al., "Synthesis, antibacterial activity and mode of action of novel linoleic acid—dipeptide—spermidine conjugates," Org. Biomol. Chem, 2012, vol. 10, pp. 8326-8335.

Karatan et al., "NspS, a Predicted Polyamine Sensor, Mediates Activation of *Vibrio cholera* Biofilm Formation by Norspermidine," Journal of Bacteriology, Nov. 2005, vol. 187(21), pp. 7434-7443, doi: 10.1128/jb.187.21.7434-7443.2005.

Kaur et al., "A Comparison of Chloroambucil- and Xylene-Containing Polyamines Leads to Improved Ligands for Accessing the Polyamine Transport System," J. Med. Chem., 2008, vol. 51, pp. 1393-1401.

Kikuchi et al., "Antimicrobial activities of squalamine mimics," Antimicrob. Agents Chemother., 1997, vol. 41(7):1433-1438.

Kim et al., "Synthesis and Antimicrobial Activity of Squalamine Analogue," Bioorganic & Medicinal Chemistry, 2000, vol. 8, pp. 2059-2065.

Klink et al., "A Systematic Study of the Photophysical Processes in Polydentate Triphenylene-Functionalized $Eu^{3+}$, $Tb^{3+}$, $Nd^{3+}$, $Yb^{3+}$, and $Er^{3+}$ Complexes," J. Phys. Chem. A, 2000, vol. 104, No. 23, pp. 5457-5468.

Kolodkin-Gal et al., "A Self-Produced Trigger for Biofilm Disassembly that Targets Exopolysaccharide," Cell, Apr. 2012, vol. 149, pp. 684-692.

Kolodkin-Gal et al., "D-Amino Acids Trigger Biofilm Disassembly," Science, Apr. 2010, vol. 328, pp. 627-629.

Kuca et al., "Preparation of Benzalkonium Salts Differing in the Length of a Side Alkyl Chain," Molecules, 2007, vol. 12, pp. 2341-2347.

Kwon et al., "Polyamine Effects on Antibiotic Susceptibility in Bacteria," Antimicrobial Agents and Chemotherapy, Jun. 2007, vol. 51(6), pp. 2070-2077.

LaDow et al., "Bicephalic amphiphile architecture affects antibacterial activity," European Journal of Medicinal Chemistry, 2011, vol. 46, pp. 4219-4226.

Liao et al., "Polyamine Transport as a Target for Treatment of *Pneumocystis* Pneumonia," Antimicrobial Agents and Chemotherapy, Dec. 2009, vol. 53(12), pp. 5259-5264.

Loncle et al., "Synthesis of new 7-aminosterol squalamine analogues with high antimicrobial activities through a stereoselective titanium reductive amination reaction," Tetrahedron, 2007, vol. 63, pp. 12968-12974.

Martin, B. et al., "N-Benzylpolyamines as vectors of boron and fluorine for cancer therapy and imaging: Synthesis and biological evaluation," Journal of Medicinal Chemistry, American Chemical Society, US, vol. 44, No. 22, Oct. 25, 2001, pp. 3653-3664.

Muth et al., "Polyamine transport inhibitors: design, synthesis, and combination therapies with Difluoromethylornithine," Journal of Medicinal Chemistry, 2014, vol. 57, pp. 348-363.

Patel et al., "Polyamines are Essential for the Formation of Plague Biofilm," Journal of Bacteriology, 2006, 188(7); 2355-2363.

PCT/US2014/039039, International Preliminary Report on Patentability, dated Dec. 3, 2015, 10 pages.

PCT/US2014/039039, International Search Report and Written Opinion, dated Aug. 11, 2014, 11 pages.

PCT/US2014/039040, International Preliminary Report on Patentability, dated Dec. 3, 2015, 8 pages.

PCT/US2014/039040, International Search Report and Written Opinion, dated Aug. 11, 2014, 10 pages.

PCT/US2018/026320, International Preliminary Report on Patentability dated Oct. 17, 2019, 11 pages.

PCT/US2018/026320, International Search Report dated Jul. 31, 2018, 7 pages.

Pernak et al., "Antimicrobial activities of new analogues of benzalkonium chloride," Eur. J. Med. Chem., 1999, vol. 34, pp. 765-771.

PubChem CID 24807066, http://pubchem.ncbi.nlm.nih.gov/summary/summary.cgi?q=all&cid=24807066, retrieve date Feb. 12, 2014, 3 pages.

PubChem CID 24807068, http://pubchem.ncbi.nlm.nih.gov/summary/summary.cgi?q=all&cid=24807068, retrieve date Feb. 12, 2014, 3 pages.

PubChem CID 24807458, http://pubchem.ncbi.nlm.nih.gov/summary/summary.cgi?q=all&cid=24807458, retrieve date Feb. 12, 2014, 2 pages.

Randazzo et al., "A series of cationic sterol lipids with gene transfer and bactericidal activity," Bioorganic & Medicinal Chemistry, 2009, vol. 17, pp. 3257-3265.

Rehse et al., "Antimicrobial Effects of Oligoamines," Arch. Pharm. Pharm. Med. Chem., 1996, vol. 329, pp. 155-160.

Rosini et al., "Structure-Activity Relationships of Methoctramine-Related Polyamines as Muscular Nicotinic Receptor Noncompetitive Antagonists. 2.[1] Role of Polymethylene Chain Lengths Separating Amine Functions and of Substituents on the Terminal Nitrogen Atoms," J. Med. Chem., 2002, vol. 45, No. 9, pp. 1860-1878.

Rozansky et al., "Studies on the Antibacterial Action of Spermine," J. gen. Microbiol., 1954, vol. 10, pp. 11-16.

Sadownik et al., "Rapid Construction of a Squalamine Mimic," J. Am. Chem. Soc., 1995, vol. 117, pp. 6138-6139.

Salunke et al., "Bile acid-polyamine conjugates as synthetic ionophores," ARKIVOC, 2003 (ix) 115-125.

Shu et al., "The synthesis of spermine analogs of the shark aminosterol squalamine," Steroids, 2002, vol. 67, pp. 291-304.

(56) References Cited

OTHER PUBLICATIONS

Strekowski et al., "Quantitative Structure-Activity Relationship Analysis of Cation-Substituted Polyaromatic Compounds as Potentiators (Amplifiers) of Bleomycin-Mediated Degradation of DNA," J. Med. Chem., 1991, vol. 34, No. 2, pp. 580-588.
Sutar et al., "Tunable emission in lanthanide coordination polymer gels based on a rationally designed blue emissive gelator," Chem. Commun., 2015, vol. 51, pp. 9876-9879.
Tan et al., Pharm. Res. 24:2297-2308 (2007).
Thorsteinsson et al., "Soft Antimicrobial Agents: Synthesis and Activity of Labile Environmentally Friendly Long Chain Quarternary Ammonium Compounds," J. Med. Chem., 2003, vol. 46, pp. 4173-4181.
U.S. Appl. No. 14/076,143, Final Office Action, dated Apr. 3, 2014.
U.S. Appl. No. 14/076,143, Non-Final Office Action, dated Feb. 6, 2014, 13 pages.
U.S. Appl. No. 14/507,701, Final Office Action, dated Apr. 13, 2016, 10 pages.
U.S. Appl. No. 14/507,701, Non-Final Office Action, dated Sep. 17, 2015, 17 pages.
U.S. Appl. No. 14/683,075, Final Office Action dated Apr. 7, 2017, 23 pages.
U.S. Appl. No. 14/683,075, Non-final Office Action, dated Sep. 23, 2016, 15-pages.
U.S. Appl. No. 15/806,701, Non-final Office Action dated Mar. 6, 2019, 8 pages.
Wang et al., "Defining the Molecular Requirements for the Selective Delivery of Polyamine Conjugates into Cells Containing Active Polyamines Transporters," J. Med. Chem., 2003, vol. 46, pp. 5129-5138.
Williams et al., "A modified CDC biofilm reactor to produce mature biofilms on the surface of PEEK membranes for an in vivo animal model application," Curr Microbiol 62, 1657-1663 (2011).
Williams et al., "In Vivo Efficacy of a Silicone-Catonic Steriod Antimicrobial Coating to Prevent Implant-Related Infection," Biomaterials 33, 8641-8656 (2012).
Williams et al., "Observing the Biofilm Matrix of *Staphylococcus epidermidis* ATCC 35984 Grown Using the CDC Biofilm Reactor," Microsc. Microanal. 16,, 143-152, 2010, doi: 10.1017/s143192760999136x.
Williams et al., "Use of delrin plastic in a modified CDC biofilm reactor," Res J. Microbiol 6, 425-429 (2011).
Williams et al., "Using biofilms as initial inocula in animal models of biofilm-related infections," J Biomed Mater Res Part B Appl. Biomater. 2012, 100, 1163-69; 10.1002/jbm.b.31979.
Williams et al., Experimental model of biofilm implant-related osteomyelitis to test combination biomaterial using biofilms as initial inocula, J. Biomed Mat Res A 100, 1888-1900 (2012).
Williams, Preventing Biofilm Implant-Related Osteomyelitis Using a Novel Synthetic Analog of Antimicrobial Peptides, 2012, Doctoral Dissertation, 296 pages.
Application No. JP2019-554606, Notice of Decision to Grant, dated Feb. 8, 2022, 2 pages.

\* cited by examiner

COMPOSITIONS AND METHODS COMPRISING A TRIARYL POLYAMINE

CROSS-REFERENCES TO RELATED APPLICATIONS

The present application is a continuation of International Patent Application No. PCT/US2018/026320, filed Apr. 5, 2018, which claims priority to U.S. Provisional Application No. 62/482,106, filed Apr. 5, 2017, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

Part of the work leading to this invention was carried out with U.S. Government support provided by the Henry M. Jackson Foundation for the Advancement of Military Medicine (Grant No. HU0001-15-2-0003) and the Veterans Affairs Medical Center (Grant No. 1I01RX002287-01). The U.S. Government therefore has certain rights in this invention.

FIELD OF THE INVENTION

The present invention is directed to triaryl polyamine compounds, compositions, and methods, which preferably have antimicrobial or dispersing activity against a variety of bacterial strains capable of forming biofilms. Various aspects and embodiments relate generally to triaryl polyamine compounds and to methods of preparing or using such compounds.

BACKGROUND OF THE INVENTION

Antimicrobial compounds, such as traditional antibiotics, have the ability to kill or to retard the growth of bacteria, fungi, and other microorganisms. Some antimicrobial compounds also are effective against viruses. Antimicrobial compounds are used in a wide variety of clinical settings, industrial applications, food production facilities and environmental applications all across the globe in an effort to reduce the risk of, for example, bacterial colonization and development of disease in people.

Traditional antibiotics are primarily derivatives or synthetic mimics of natural compounds secreted by bacteria, plants, or fungi. These compounds typically have very specific methods of action against a cell wall/membrane component of bacteria, or an enzyme/protein in a metabolic pathway. Examples of traditional antibiotics on the market include penicillin, oxacillin, vancomycin, gentamicin, rifampicin and amoxicillin, among others.

Because bacteria have the ability to develop resistance genes to these antibiotics as a result of genetic mutations or acquired defense mechanisms that target the specific activity of the antibiotics, bacteria typically have the ability to develop resistance to traditional antibiotics. Increasingly more prevalent bacterial resistance has made traditional antibiotics to become less and less effective in a variety of applications.

Bacterial resistance to antibiotics represents one of the most underappreciated threats to modern society. See Zhang et al., *Antibiotic resistance as a global threat: Evidence from China, Kuwait and the United States*, Global Health 2, 6 (2006). Currently, more than 90% of clinical isolates of *Staphylococcus aureus* display resistance to penicillin. See Balaban et al., *Control of Biofilm Infections by Signal Manipulation*, Ch. 1, 1-11 (Springer, 2008). Recent reports have even indicated that bacteria in natural ecosystems metabolize antibiotics as an energy source. See Leslie, *Germs Take a Bite Out of Antibiotics*, Science 320, 33 (2008). The trend of bacterial resistance continues to increase as indicated by almost daily scientific publications and world news reports of antibiotic resistant superbugs such as carbapenem-resistant Enterobacteriacea, vancomycin-resistant Enterococci, multidrug-resistant *Pseudomonas aeruginosa* and methicillin-resistant *Staphylococcus aureus* (MRSA). See, e.g., FoxNews.com. *Europe in the Grip of Drug-Resistant Superbugs* (2011); Melnick, M., TIME (2010); Arias et al., *The rise of the Enterococcus: beyond vancomycin resistance*, Nat Rev Microbiol 10, 266-278 (2012); Jain, R. et al., *Veterans affairs initiative to prevent methicillin-resistant Staphylococcus aureus infections*, N Engl J Med 364, 1419-1430 (2011); Nordmann et al., *The real threat of Klebsiella pneumoniae carbapenemase-producing bacteria*, Lancet Infect Dis 9, 228-236 (2009); Aloush et al., *Multidrug-resistant Pseudomonas aeruginosa: risk factors and clinical impact*, Antimicrob Agents Chem 50, 43-48 (2006).

Biofilm-impaired wounds and antibiotic resistance constitute significant concerns to military and civilian healthcare organizations worldwide. Multiple reports from Operation Iraqi Freedom/Operation Enduring Freedom have indicated that multidrug-resistant bacteria and antibiotic resistance constitute one of the most disconcerting aspects of military theater treatment. See, e.g., Calhoun et al., *Multidrug-resistant Organisms in Military Wounds from Iraq and Afghanistan*, Clinical Orthopaedics and Related Research 466, 1356-1362 (2008); Murray et al., *Bacteriology of War Wounds at the Time of Injury*, Military Medicine 171, 826-829 (2006); Hujer et al., *Analysis of Antibiotic Resistance Genes in Multidrug-Resistant Acinetobacter sp. Isolates from Military and Civilian Patients Treated at the Walter Reed Army Medical Center*, Antmicrobial Agents and Chemotherapy 50, 4114-4123 (2006). *A. baumannii* is a common complicating organism in wounded warriors returning from current conflicts in Iraq and Afghanistan that is well-known for its biofilm forming nature. Its multidrug-resistant characteristic has made it difficult to treat in injured soldiers, has led to delayed wound healing and many other complications. Limited therapeutic options exist for this organism.

Multiple factors contribute to bacterial cells' ability to resist the effects of antibiotics. See, e.g., Morita et al., *Antibiotic Inducibility of the MexXY Multidrug Efflux System of Pseudomonas aeruginosa: Involvement of the Antibiotic-Inducible PA5471 Gene Product*, Journal of Bacteriology 188, 1847-1855 (2006); Tran et al., *Heat-Shock Protein ClpL/HSP100 Increases Penicillin Tolerance in Streptococcus pneumoniae*, Advances in Oto-rhino-laryngology 72, 126-128 (2011); Livorsi et al., *Virulence Factors of Gram-Negative Bacteria in Sepsis With a Focus on Neisseria meningitidis*, Contributions to Microbiology 17, 31-47 (2011); Nostro, et al., *Specific Ion Effects on the Growth Rates of Staphylococus aureus and Pseudomonas aeruginosa*, Physical Biology 2, 1-7 (2005). Amongst these factors is the ability of bacteria to develop a biofilm. See, e.g., Costerton et al., *How bacteria stick*, Sci Am 238, 86-95 (1978); Lawrence et al., *Optical sectioning of microbial biofilms*, J Bacteriol 173, 6558-6567 (1991); ZoBell, *The Effect of Solid Surfaces upon Bacterial Activity*, Journal of Bacteriology 46, 39-56 (1943). Biofilms have unique characteristics that allow them to withstand, or defend themselves against a variety of perturbations including exposure to antibiotics.

Biofilms are surface-attached communities of bacteria, often polymicrobial, that produce a slimy, extracellular polysaccharide substance (EPS) that encapsulates them. The EPS provides protection, Leid et al., *The Exopolysacharide Alginate Protects Pseudomonas aeruginosa Biofilm Bacteria from IFN-γ-Mediated Macrophage Killing*, The Journal of Immunology 175, 7512-7518 (2005), as well as a reserve of nutrients, water and trace elements to sustain life. Costerton et al., *The Bacterial Glycocalyx in Nature and Disease*, Annual Review of Microbiology 35, 299-324 (1981). Biofilms are the predominant phenotype of bacteria in natural ecosystems. Gram-negative bacteria, Gram-positive bacteria, and mycobacteria, in addition to other unicellular organisms, can produce biofilms.

Within the biofilm community, bacteria may have several methods of defending themselves against the biocidal effects of antibiotics. First, they have strength in numbers. Biofilms may contain millions or trillions of cells in a very small volume. Second, bacteria in a biofilm have the ability to rapidly transfer genetic material, such as plasmids, that specifically code for the production of molecules that protect them against antibiotics. Lujan et al., *Disrupting Antibiotic Resistance Propagation by Inhibiting the Conjugative DNA Relaxase*, PNAS 104, 12282-12287 (2007); Lederberg et al., *Gene Recombination in Escherichia coli*. Nature 158, 529-564 (1946). Rates of plasmid transfer in biofilms have been shown to be much higher than amongst planktonic bacteria, which are free-floating in an environment. Hausner et al., *High Rates of Conjugation in Bacterial Biofilms as Determined by Quantitative In Situ Analysis*, Applied and Environmental Microbiology 65, 3710-3713 (1999). Third, as a biofilm community matures, it creates an oxygen gradient such that an oxygen-rich environment exists on the outer edges of a biofilm, whereas an oxygen-deprived, or anaerobic, area exists in the deepest portions of a biofilm. Walters et al., *Contributions of Antibiotic Penetration, Oxygen Limitation, and Low Metabolic Activity to Tolerance of Pseudomonas aeruginosa biofilms to Ciprofloxacin and Tobramycin*, Antimicrobial Agents and Chemotherapy 47, 317-323 (2003); Borriello et al., *Oxygen Limitation Contributes to Antibiotic Tolerance of Pseudomonas aeruginosa in Biofilms*, Antimicrobial Agents and Chemotherapy 48, 2659-2664 (2004). This may result in reduced metabolic activity in those cells that dwell in the interior of the biofilm. Importantly, traditional antibiotics are typically effective against bacterial cells that are rapidly dividing, i.e., in a logarithmic phase of growth. Mandell, *Interaction of Intraleukocytic Bacteria and Antibiotics*, The Journal of Clinical Investigation 52, 1673-1673 (1973); Gilbert et al., *Influence of Growth Rate on Susceptibility to Antimicrobial Agents: Biofilms, Cell Cycle, Dormancy, and Stringent Response*, Antimicrobial Agents and Chemotherapy 34, 1865-1868 (1990). Fourth, in a mature biofilm, water channels form throughout the community. Stoodley et al., *Liquid flow in biofilm systems*, App Env Microbiol 60, 2711-2716 (1994). These water channels have the ability to diffuse, remove or prevent toxic byproducts as well as antibiotics from interacting with cells in the biofilm. For novel antimicrobial agents to be effective over the long term, addressing each of these four characteristics may increase the potential for success in a variety of applications including healthcare, industrial, environmental, agricultural and sanitation industries. Furthermore, biofilms tend to secrete proteoglycan materials that create an extracellular matrix, which has the ability to potentially bind and hinder the activity of antibiotics. These conditions reduce the efficacy of traditional antibiotic agents, rendering them up to 1,000× less active against biofilms.

Alternative approaches to killing bacteria include the use of antimicrobial agents that have fast-acting and nonspecific mode of activity against the cell membrane of bacteria. These alternate compounds include detergents, squalamine, quaternary ammonium compounds, and naturally occurring antimicrobial peptides, among others. By attacking and depolarizing the cell membrane in a nonspecific fashion at a faster rate, agents that attack the cell membrane globally can kill bacteria before they have time to upregulate their defense mechanisms. In addition, modes of action of these alternate antimicrobials are not limited to a specific protein or enzyme within a metabolic pathway.

A hallmark of biofilm exopolysaccharides is the presentation of acidic residues from repeated glucoronic acid motifs and pyruvate derived acetals. Losick et al. have demonstrated that the simple polyamines spermine and norspermidine were naturally occurring inhibitors of biofilm formation, endogenously produced at high concentrations (50-80 µM) in response to nutrient limiting conditions and waste accumulation in mature pellicles (Kolodkin-Gal, I. et al., A self-produced trigger for biofilm disassembly that targets exopolysaccharide. *Cell* 149 (2012)). In this study, they were able to demonstrate that norspermidine could inhibit biofilm formation at 25 µM and showed that, at similar concentrations, it could disperse the exopolysaccharide component of the matrix but not the protein component. Interestingly, spermidine was only active at much higher concentrations (~1 mM) leading them to propose a rationale for this activity in the ability of the polyamines to engage the acidic residues in the matrix at regular intervals.

However, as important as it is to kill bacteria and prevent their ability to cause infections in humans or animals, or contaminate unwanted processes in industrial, agricultural or environmental applications, when bacteria are attached to a surface, it sometimes may be more beneficial to not only kill bacteria, but also to cause them to "fall off" of a surface as well, e.g. disperse or dislodge bacteria in a biofilm community. In some aspects, the present invention provides compounds, compositions, and methods that have shown the ability to disperse or dislodge bacterial cells in a biofilm, such that the cells are no longer able to reattach and form new biofilm communities, and, notably, the same compounds, compositions, and methods kill substantially all bacteria cells in a biofilm.

By dispersing a biofilm and killing the cells within it, at least two benefits are provided. This may be particularly important when considering the fact that although bacteria in a biofilm, which may be attached to a surface, can be killed by an antimicrobial agent, the dead cells and extracellular matrix residues may provide an attachment point for viable bacteria to re-adhere and form a biofilm once again with greater affinity. If biofilms are dispersed and killed, viable bacteria that are introduced to a surface will have reduced ability to preferentially adhere to that area. This can be particularly important in industrial applications wherein the formation of biofilms on a surface can be problematic, as well as medical applications wherein bacteria may adhere to the surface of a medical device.

Thus, there is a need for novel compounds, compositions, and methods that have potent antimicrobial and anti-biofilm activity against a variety of bacterial strains, especially at high bacterial concentrations and against antibiotic-resistant bacteria. In an era of reduced antibiotic efficacy, the development of a new class of antibiofilm agent that is active against *A. baumannii* and other organisms is important. The addition of a topical therapy that can be used in conjunction with and improve standards of care would be advantageous, and it potentially could address current clinical limitations in the management of biofilm wound-related infections.

BRIEF SUMMARY OF THE INVENTION

It is an object of the present invention to provide novel compounds, compositions, and methods having antimicrobial activity and dispersing activity against a wide variety of bacterial strains capable of forming biofilms. In some preferred aspects, the invention provides compounds, compositions, and methods that are effective against antibiotic-resistant bacterial biofilms.

It has been discovered that compounds, compositions, and methods of the present invention rapidly disperse biofilms and kill microorganisms such as bacteria, so that the microorganisms do not have an opportunity to upregulate their defense mechanisms. Thus, there may be a reduced risk of bacteria developing resistance to the compounds, compositions, and methods of the present invention. Furthermore, such compounds, compositions, and methods may not be limited to eradicating bacteria that are in log-phase growth. The ability of compounds, compositions, and methods of the present invention to disperse biofilms while demonstrating antimicrobial activity may address many of the characteristics that make biofilm communities difficult to treat using traditional antibiotics. More specifically, by dispersing and killing bacteria in a biofilm, water channels and the bacterial community as a whole may be broken apart, allowing for broader distribution of antimicrobial agent(s) to a greater number, or even substantially all, of the cells within a biofilm.

Aspects of this disclosure feature methods of killing, dispersing, dislodging, treating, and reducing biofilms as well as preventing or inhibiting biofilm formation. In some embodiments, the method comprises exposing a biofilm to an effective amount of a composition of the present invention to thereby kill, disperse, dislodge, treat, reduce, prevent, or inhibit bacterial biofilms.

In some aspects, the compounds, compositions, and methods of the present invention have significant potential to eradicate bacteria within a biofilm as well as cause the biofilm to disperse or dislodge, resulting in a variety of potential applications across multiple settings. The inventive compounds, compositions, and methods could reduce the risk of antibiotic resistance development that is common with traditional antibiotics, and they could also provide a targeted class of compounds against biofilms. In some aspects, they are effective in treating or preventing biofilm-impaired wounds that are caused by well-established biofilms.

In some embodiments, the present invention provides a triaryl polyamine compound.

In some embodiments, the present invention provides a compound compound selected from the group including an $A^{1-6}$ ring

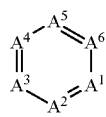

and a salt thereof;

wherein:

each $A^{1-6}$ ring member $A^1$, $A^2$, $A^3$, $A^4$, $A^5$, and $A^6$ is independently selected from the group including N, $CR^t$, $CR^a$, and $CR^b$; or, alternatively, a pair of adjacent $A^{1-6}$ ring members join to form an independently selected aryl, cycloalkyl, heterocyclyl, or heterocycloaryl $B^1$ ring that is fused with the $A^{1-6}$ ring at the pair's adjacent $A^{1-6}$ ring positions;

wherein two of the $A^{1-6}$ ring members are each an independently selected $CR^t$;

each $R^t$ is an independently selected $A^{7-11}$ ring

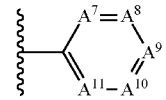

each $A^{7-11}$ ring member $A^7$, $A^8$, $A^9$, $A^{10}$, and $A^{11}$ is independently selected from the group including N, $CR^t$, $CR^a$, and $CR^b$; or, alternatively, a pair of adjacent $A^{7-1}$ ring members join to form an independently selected aryl, cycloalkyl, heterocyclyl, or heterocycloaryl $B^2$ ring that is fused with the $A^{7-11}$ ring at the pair's adjacent $A^{7-11}$ ring positions;

wherein for each $R^t$, one $A^{7-11}$ ring member is an independently selected $CR^a$;

each $B^1$ or $B^2$ ring, if present, is optionally substituted with up to one $R^a$ group and with up to three independently selected $R^5$ groups;

each $R^a$ is a member independently selected from the group including

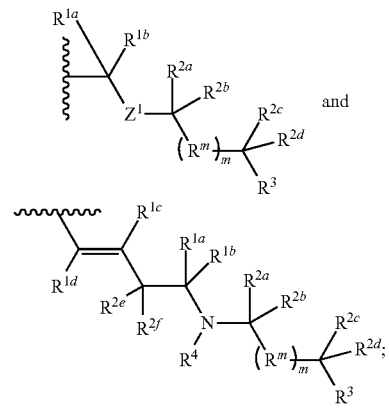

each $R^{1a}$, $R^{1b}$, $R^{1c}$, and $R^{1d}$ is a member independently selected from the group including hydrogen, fluoro, alkyl, and fluoroalkyl; or, alternatively, an $R^{1a}$ and an $R^{1b}$ join to form an oxo group;

each $R^{2a}$, $R^{2b}$, $R^{2c}$, $R^{2d}$, $R^{2e}$, and $R^{2f}$ is a member independently selected from the group including hydrogen, alkyl, fluoroalkyl, alkenyl, alkynyl, aryl, heteroaryl, arylalkyl, or heteroarylalkyl; alternatively, a pair of $R^2$ members from the same $R^a$ group independently selected from the group $R^{2a}$ and $R^{2b}$, $R^{2c}$ and $R^{2d}$, and $R^{2e}$ and $R^{2f}$ join to form a member independently selected from the group including spirocycloalkyl, spiroheterocycyl, and oxo; or, alternatively, an $R^{2a}$ and an $R^{2c}$ from the same $R^a$ group join to form a ring independently selected from the group including cycloalkyl and heterocycyl;

each $R^m$ is a member independently selected from the group including $—CR^{2a}R^{2b}—$, $—CR^{2c}R^{2d}—$, $—C(R^{2a})=(R^{2b})—$, $—CC—$, and $—C(R^{2a})(R^{2b})-L-C(R^{2c})(R^{2d})—$;

each m is an integer independently selected from 1 to 20;

each L is a member independently selected from the group including a bond, $—O—$, $—C(O)O—$, $—NR^4—$, $—NR^4C(O)—$, and $—C(O)NR^4—$;

each $R^3$ is a member independently selected from the group including $—Z^1—R^4$, $—Z^1—Y^1—R^4$, $—Z^1—Y^1—Y^2—R^4$, and $—Z^1—Y^1—Y^2—Y^3—R^4$;

each $R^4$ is a member independently selected from the group including hydrogen, alkyl, fluoroalkyl, alkenyl, alkynyl, aryl, cycloalkyl, heteroaryl, arylalkyl, cycloalkylalkyl, and heteroarylalkyl; or, alternatively, for an $—N(R^4)_2$ group, one of the two $R^4$ in the group is a member selected from the group including $—(CO)OR^{6a}—$, $—(CO)N(R^{6a})(R^{6b})$, and $—C(NR^{6a})N(R^{6b})(R^{6c})$; or, alternatively, for an $—N(R^4)_2$ group, the two $R^4$ groups join to form a heterocyclic ring;

each $Y^1$, $Y^2$, and $Y^3$ is an independently selected group of Formula IA:

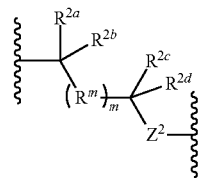

IA each $Z^1$ and $Z^2$ is a member independently selected from the group including $—N(R^4)—$ and $—O—$; and each $R^b$ is a member independently selected from hydrogen or an $R^5$;

each $R^5$ is a member independently selected from the group including alkyl, hydroxyl, alkoxy, aminoalkoxy, alkylamino, alkylaminoalkoxy, alkenyl, alkynyl, aryl, aryloxy, arylamino, cycloalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino; hydroxyalkyl, aminoalkyl, and alkylaminoalkyl;

each $R^{6a}$, $R^{6b}$, and $R^{6c}$ is a member independently selected from the group including hydrogen, alkyl, fluoroalkyl, alkenyl, alkynyl, aryl, heteroaryl, cycloalkyl, arylalkyl, heteroarylalkyl, and cycloalkylalkyl; or, alternatively, two $R^{6n}$ members $R^{6a}$ and $R^{6b}$ or $R^{6a}$ and $R^{6c}$ join to form a heterocyclyl ring;

wherein the polyamine compound comprises at least two primary or secondary amino groups.

In some embodiments, the present invention provides an antibacterial composition, the composition comprising, consisting of, or consisting essentially of a polyamine compound as set forth in any of the embodiments, aspects, or combination of aspects herein; and an excipient.

In some embodiments, the present invention provides a method of inhibiting the formation of a biofilm comprising, consisting of, or consisting essentially of the step of administering a polyamine compound, or a composition comprising the polyamine compound, as set forth in any of the embodiments, aspects, or combination of aspects herein; thereby inhibiting incorporation of the planktonic bacteria into the biofilm.

In some embodiments, the present invention provides a method of enhancing wound healing comprising, consisting of, or consisting essentially of the step of treating a patient with a polyamine compound, or a composition comprising the polyamine compound, as set forth in any of the embodiments, aspects, or combination of aspects herein, thereby enhancing healing of a wound in the patient.

In some embodiments, the present invention provides a method of making a polyamine compound, or a composition comprising, consisting essentially of, or consisting of the polyamine compound, as set forth in any of the embodiments, aspects, or combination of aspects herein.

In some embodiments, a method of the instant invention comprising a combination of therapies, e.g., IV+topical, may provide advantages to treat or to prevent biofilm-related infection.

These and other objects, aspects, and embodiments will become more apparent when read with the following detailed description and drawings.

BRIEF DESCRIPTION OF THE DRAWINGS

Various embodiments and aspects of the present invention are shown and described in reference to the numbered drawings. The skilled artisan will understand, however, that the inventions described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

FIG. 1A shows the partial thickness wounds surgically created on a pig back. Bacteria were inoculated in 50 µL of PBS or on collagen plugs. FIG. 1B shows scanning electron microscope (SEM) images of *A. baumannii* biofilms grown on the surface of a collagen plug.

FIG. 2A shows wound inoculation with planktonic bacteria, while FIG. 2B shows the results of planktonic wound infection. FIG. 2C shows wound inoculation with a biofilm, while FIG. 2D shows the results of biofilm wound infection.

Figure 1:
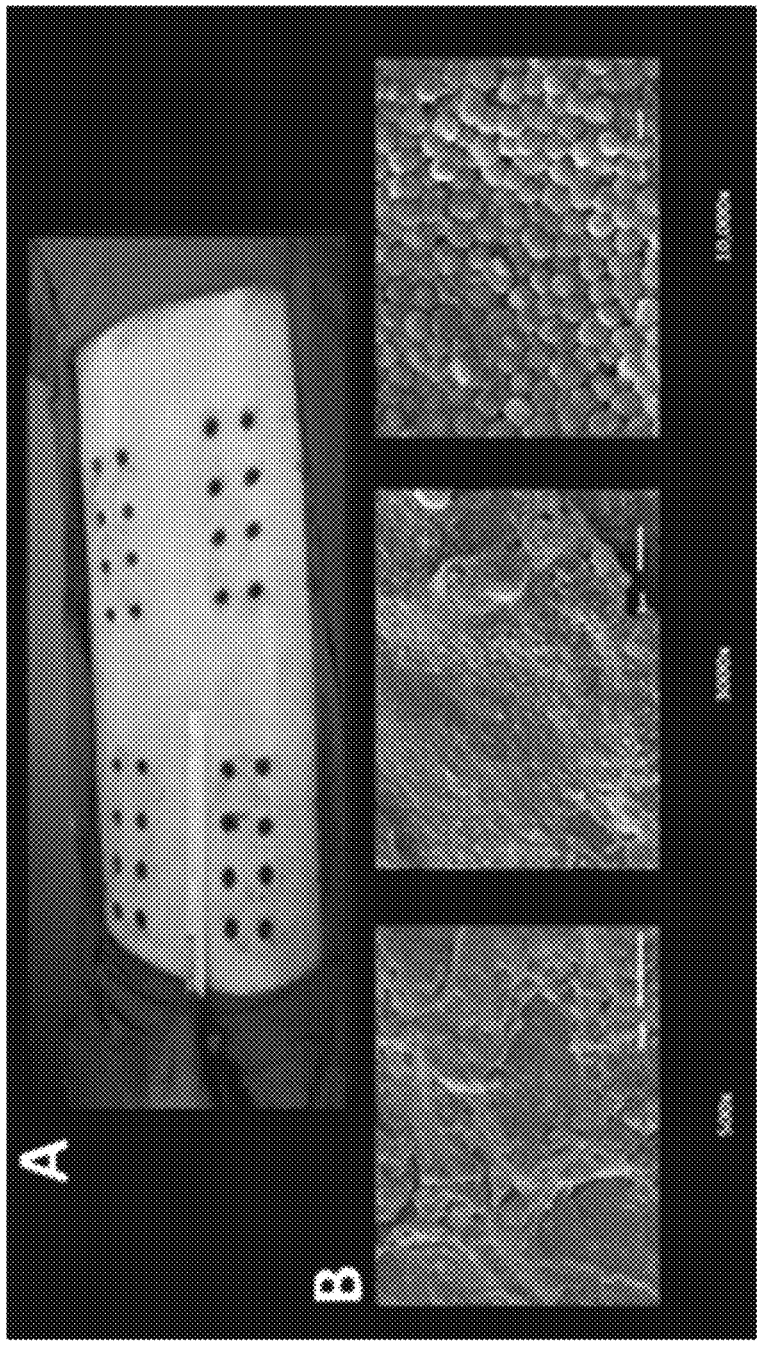
FIGS. 1A and 1B show materials from the wound healing study of Example 3.
Figure 2:
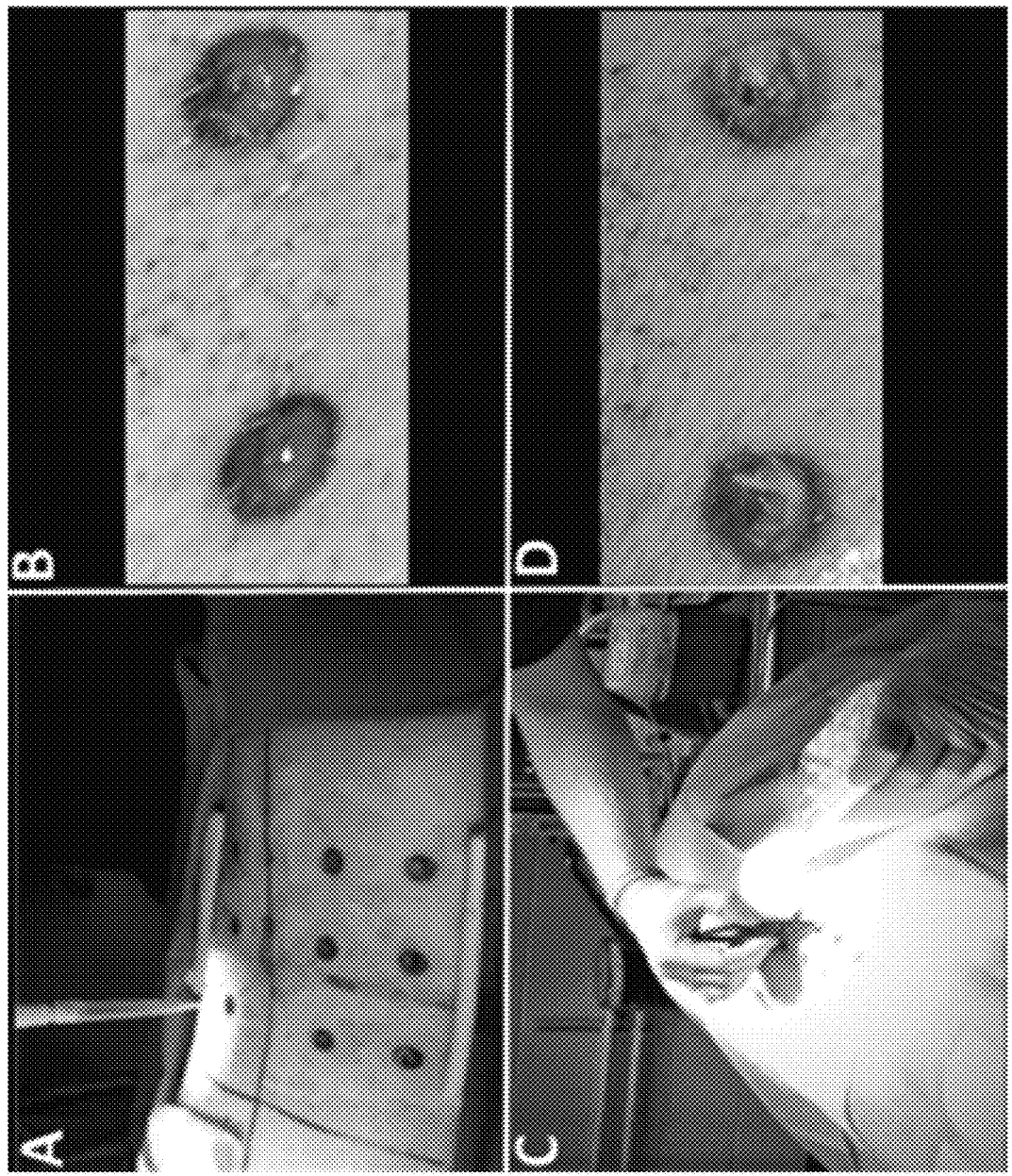
FIG. 2A through FIG. 2D show methods and results from the wound healing study of Example 3.
Figure 3:
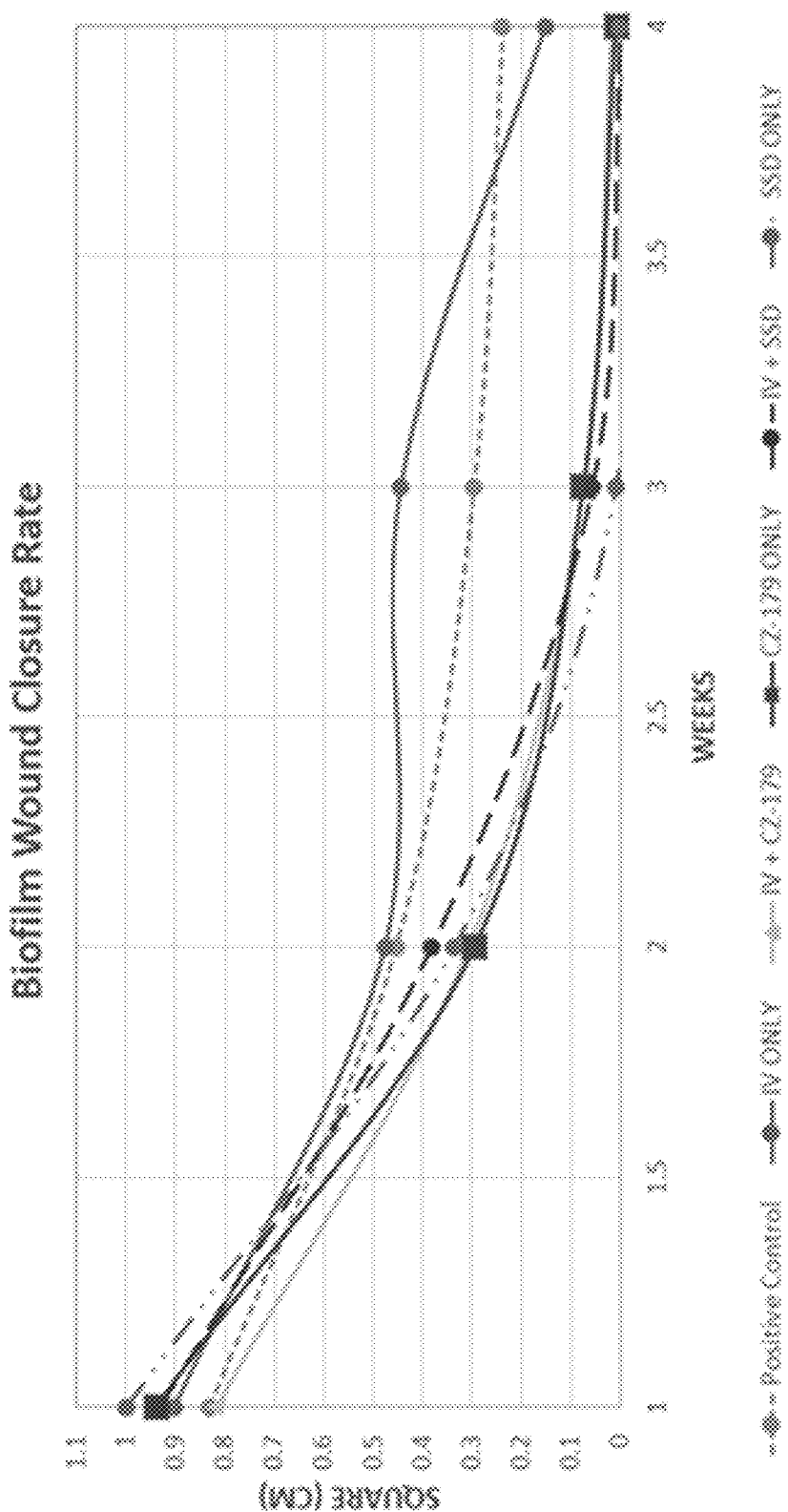
FIG. 3 shows the wound closures rates from the planktonic inoculations of Example 3 with controls.

It will be appreciated that the drawings are illustrative and not limiting of the scope of the invention, which is defined by the appended claims. The embodiments shown accomplish various aspects and objects of the invention; however, it will be understood that other aspects, features or modifications may be within the scope of the appended claims. It is appreciated that it is not possible to clearly show each element and aspect of the invention in a single figure, and as such, multiple figures are presented to separately illustrate various details of the invention in greater clarity. Similarly, not every embodiment need accomplish all advantages of the present invention.

DETAILED DESCRIPTION OF THE INVENTION

It will be appreciated that reference throughout this specification to aspects, features, advantages, or similar language does not imply that all of the aspects and advantages that may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but does not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in some embodiments that may not be present in all embodiments of the invention.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including U.S. Appl. Nos. 61/482,522; 61/482,523; 61/591,601; 61/616,944; 61/826,453; 61/826,761; 61/836,555; 61/834,149; Ser. Nos. 13/379,191; 14/076,143; 14/076,149; 14/507,701; 14/683,075; and 15/222,576; as well as Int'l Pat. Publ. Nos. WO 2010/148390, 2012/151555, and 2013/148230 and PCT Appl. No. PCT/US14/39039. In case of conflict, the present specification, including these definitions, will control.

The terms "a," "an," and "the" as used herein not only includes aspects with one member, but also includes aspects with more than one member. For example, an embodiment including "a polyamine compound and an excipient" should be understood to present some aspects with at least a second polyamine compound, at least a second excipient, or both.

The term "about" as used herein to modify a numerical value indicates a defined range around that value. If "X" were the value, "about X" would generally indicate a value from 0.90X to 1.10X. Any reference to "about X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20" is equivalent to "from about 5 to about 20." When "about" is applied to the first value of a set of values, it applies to all values in that set. Thus, "about 7, 9, or 11" is equivalent to "about 7, about 9, or about 11."

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "alkanoyl" as used herein includes an alkyl-C(O)— group wherein the alkyl group is as defined herein. Examples of alkanoyl groups include, but are not limited to, acetyl and propanoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond. When the indicated number of carbon atoms is 1, then the $C_i$ alkenyl is double bonded to a carbon (i.e., a carbon equivalent to an oxo group). In some aspects, the chain includes 1 to 12, about 2 to 15, about 2 to 12, about 2 to 8, or about 2 to 6 carbon atoms. Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, 3-(1,4-pentadienyl), and hexadienyl.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from fluoro, hydroxy, alkoxy, amino, alkylamino, acylamino, thio, and alkylthio, with the proviso that no hydrogen atom substituent on the carbon-carbon double bond is replaced by a hydroxy, amino, or thio group. In some aspects, the alkenyl group is unsubstituted or not optionally substituted.

The term "alkyl" as used herein includes an aliphatic hydrocarbon chain that may be straight chain or branched. The chain may contain an indicated number of carbon atoms: For example, $C_1$-$C_{12}$ indicates that the group may have from 1 to 12 (inclusive) carbon atoms in it. If not otherwise indicated, an alkyl group contains from 1 to about 20 carbon atoms. In some aspects, alkyl groups have 1 to about 12 carbon atoms in the chain. In some aspects, alkyl groups ("lower alkyl") have 1 to about 6 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, or dodecyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from fluoro, hydroxy, alkoxy, amino, alkylamino, acylamino, thio, and alkylthio. In some aspects, the alkyl group is unsubstituted or not optionally substituted.

The term "alkoxy" as used herein includes a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of a $C_1$-$C_{12}$ alkoxy group include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from fluoro, hydroxy, alkoxy, amino, alkylamino, acylamino, thio, and alkylthio, with the proviso that no hydrogen atom alpha to the ether oxygen is replaced by a hydroxy, amino, or thio group. In some aspects, the alkoxy group is unsubstituted or not optionally substituted.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4, from 1 to 2, or 1) may be replaced with a moiety independently selected from fluoro, hydroxy, alkoxy, amino, alkylamino, acylamino, thio, and alkylthio, with the proviso that no sp-hybridized hydrogen atom substituent is replaced by a hydroxy, amino, or thio group. In some aspects, the alkynyl group is unsubstituted or not optionally substituted.

The term "aroyl" as used herein includes an aryl-CO— group wherein aryl is as defined herein. Examples include, but are not limited to, benzoyl, naphth-1-oyl and naphth-2-oyl.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

An aryl group can be unsubstituted or optionally substituted. When optionally substituted, one or more hydrogen atoms of the aryl group (e.g., from 1 to 5, from 1 to 2, or 1) may be replaced with a moiety independently selected from alkyl, cyano, acyl, halo, hydroxy, alkoxy, amino, alkylamino, acylamino, thio, and alkylthio. In some aspects, the alkoxy group is unsubstituted or not optionally substituted.

The term "arylalkyl" or "aralkyl" as used herein includes an alkyl group as defined herein where at least one hydrogen substituent has been replaced with an aryl group as defined herein. Examples include, but are not limited to, benzyl, 1-phenylethyl, 4-methylbenzyl, and 1,1,-dimethyl-1-phenylmethyl.

A arylalkyl or aralkyl group can be unsubstituted or optionally substituted as per its component groups. For example, but without limitation, the aryl group of an arylalkyl group can be substituted, such as in 4-methylbenzyl, 2,4,6-trimethylbenzyl, 4-tert-butylbenzyl, 4-isopropylbenzyl, and the like. In some aspects, the group is unsubstituted or not optionally substituted, especially if including a defined substituent, such as a hydroxyalkyl or alkylaminoalkoxy group.

The linking term "comprising" or "comprise" as used herein is not closed. For example, "a composition comprising A" must include at least the component A, but it may also include one or more other components (e.g., B; B and C; B, C, and D; and the like).

A composition or method comprising certain claim elements presents an aspect that consists of those claim elements and an aspect that consists essentially of those claim elements. For example, the description of a method comprising the step A is intended to present (and provide support for) a method consisting of the step A and a method consisting essentially of the step A.

The term "cycloalkyl" as used herein includes a cyclic hydrocarbon group that may contain an indicated number of carbon atoms: For example, $C_3$-$C_{12}$ indicates that the group may have from 3 to 12 (inclusive) carbon atoms in it. If not otherwise indicated, a cycloalkyl group includes about 3 to about 20 carbon atoms. In some aspects, cyclo alkyl groups have 3 to about 12 carbon atoms in the group. In some aspects, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted cycloalkyl group can incorporate an exo- or endocyclic alkene (e.g., cyclohex-2-en-1-yl). In some aspects, a cycloalkyl group is unsubstituted or not optionally substituted.

As used herein, "cycloalkylalkyl" includes an alkyl group wherein the alkyl group includes one or more cycloalkyl substituents (typically one). Examples include, but are not limited to, cyclohexylmethyl, cyclopentylmethyl, and cyclopropylmethyl.

The terms "disorder," "disease," and "condition" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms. A disorder or disease can refer to a biofilm-related disorder or disorder caused by a planktonic bacterial phenotype that is characterized by a disease-related growth of bacteria.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, or iodo.

The term "heteroaryl" includes mono and bicyclic aromatic groups of about 4 to about 14 ring atoms (e.g., 4 to 10 or 5 to 10 atoms) containing at least one heteroatom. Heteroatom as used in the term heteroaryl refers to oxygen, sulfur and nitrogen. A nitrogen atom of a heteroaryl is optionally oxidized to the corresponding N-oxide. Examples include, but are not limited to, pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

A heteroaryl group can be unsubstituted or optionally substituted. When optionally substituted, one or more hydrogen atoms of the heteroaryl group (e.g., from 1 to 5, from 1 to 2, or 1) may be replaced with a moiety independently selected from alkyl, cyano, acyl, halo, hydroxy, alkoxy, amino, alkylamino, acylamino, thio, and alkylthio. In some aspects, the heteroaryl group is unsubstituted or not optionally substituted.

In some embodiments, a heteroaryl group includes includes mono and bicyclic aromatic groups of about 4 to about 14 ring atoms (e.g., 4 to 10 or 5 to 10 atoms) containing at least one heteroatom, but no such groups with a six-membered ring bonded to the site to which the heteroaryl group is a substituent (i.e., a "non-six-membered heteroaryl" or "n6m heteroaryl"). For example, for a group A with a non-six-membered heteroaryl substituent, A could be bonded to an indolyl moiety at the indole nitrogen, the 2-position, or the 3-position, but not at the positions on the indolyl's phenyl ring (i.e., the six-membered ring).

The term "heteroaroyl" as used herein includes a heteroaryl-C(O)— group wherein heteroaryl is as defined herein. Heteroaroyl groups include, but are not limited to, thiophenoyl, nicotinoyl, pyrrol-2-ylcarbonyl, and pyridinoyl.

The term "heterocycloyl" as used herein includes a heterocyclyl-C(O)— group wherein heterocyclyl is as defined herein. Examples include, but are not limited to, N-methyl prolinoyl and tetrahydrofuranoyl.

As used herein, "heterocyclyl" includes a non-aromatic saturated monocyclic or multicyclic ring system of about 3 to about 10 ring atoms (e.g., 5 to about 10 ring atoms, or 3 to about 6 ring atoms), in which one or more of the atoms in the ring system is an element or elements other than carbon, e.g., nitrogen, oxygen or sulfur. A heterocyclyl group optionally comprises at least one $sp^2$-hybridized atom (e.g., a ring incorporating an carbonyl, endocyclic olefin, or exocyclic olefin). In some embodiments, a nitrogen or sulfur atom of the heterocyclyl is optionally oxidized to the corresponding N-oxide, S-oxide or S,S-dioxide. Examples of monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

A heterocyl group can be unsubstituted or optionally substituted. When optionally substituted, one or more hydrogen atoms of the group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycyl group is unsubstituted or not optionally substituted.

The term "hydrophobic moiety" or "hydrophobic group" as used herein includes a moiety or a functional group that repels water. Examples may include, but are not limited to, a non-polar alkyl moiety, such as an unsubstituted alkyl group having more than five carbons; a phenyl group; and an anthracenyl group.

As used herein, the terms "hydrophilic moiety" or "hydrophilic group" includes a moiety or a functional group that has a strong affinity to water. Examples may include, but are not limited to, a charged moiety, such as a cationic moiety or an anionic moiety, or a polar uncharged moiety, such as an alkoxy group or an amine group.

As used herein, the term "hydroxyalkyl" includes an alkyl group where at least one hydrogen substituent has been replaced with an alcohol (—OH) group. In some aspects, the hydroxyalkyl group has one alcohol group. In some aspects, the hydroxyalkyl group has one or two alcohol groups, each on a different carbon atom. In some aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

As used herein, "polyamine" includes a compound that has at least two amine groups, which may be the same or different. The amine group may be a primary amine, a secondary amine, a tertiary amine, or quaternary ammonium salt. Examples may include, but are not limited to, 1,3-diaminopropane, 1,4-diaminobutane, hexamethylenediamine, dodecan-1,12-diamine, spermine, spermidine, norspermine, and norspermidine.

As used herein, "or" should in general be construed non-exclusively. For example, an embodiment of "a composition comprising A or B" would typically present an aspect with a composition comprising both A and B, and an embodiment of "a method to disperse or kill biofilms" could disperse, kill, or a combination of both. "Or" should, however, be construed to exclude those aspects presented that cannot be combined without contradiction (e.g., a composition pH that is between 9 and 10 or between 7 and 8).

As used herein, "spirocycloalkyl" includes a cycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a cyclopropyl ring incorporating the carbon to which $R^1$ and $R^2$ were bonded, this would be a spirocycloalkyl group (i.e., spirocyclopropyl).

As used herein, the term "salt" refers to acid or base salts of a compound, although for a polyamine compound, the salt is generally an acid salt of the polyamine. Illustrative examples of pharmaceutically acceptable acid salts are mineral acids (e.g., hydrochloric acid, hydrobromic acid, phosphoric acid, and the like) salts, organic carboxylic acid (e.g., acetic acid, propionic acid, glutamic acid, citric acid, and the like) salts, and organic sulfonic acid (methanesulfonic acid) salts. In some aspects, a salt may be a quaternary ammonium salts produced by reaction with an alkylating agent (e.g., methyl iodide, ethyl iodide, and the like). Additional information on suitable pharmaceutically acceptable salts can be found in Remington's, Pharmaceutical Sciences (current edition), Mack Publishing Co., Easton, Pa., which is incorporated herein by reference.

As used herein, a reference to a composition of formula A, B, C, or a salt thereof may indicate A, a salt of A, B, a salt of B, C, or a salt of C.

As used herein, "spiroheterocyclyl" includes a heterocycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a pyrrolidine ring incorporating the carbon to which $R^1$ and $R^2$ were bonded, this would be a spiroheterocyclyl group.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to prevent, to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

This can be evidenced by, e.g., an improvement in a parameter associated with a biofilm or with a biofilm-related disorder or an indication or symptom thereof, a biofilm-related industrial, agricultural, environmental, etc. condition, e.g., to a statistically significant degree or to a degree detectable to one skilled in the art. For example, "treating" a planktonic bacteria with the polyamine composition may provide a decrease in the rate or extent of biofilm formation from the planktonic bacteria as compared to a similar system without the polyamine composition. An effective amount, manner, or mode can vary depending on the surface, application, or subject and may be tailored to the surface, application, or subject. By eradicating a biofilm or preventing or slowing progression of a biofilm or of a biofilm-related disorder or an indication or symptom thereof, or a biofilm-related industrial, agricultural, environmental, etc. condition, a treatment can prevent or slow deterioration or corrosion resulting from a biofilm or from a biofilm-related disorder or an indication or symptom thereof on an affected surface or in an affected or diagnosed subject.

"Treating" and "treatment" as used herein also include prophylactic treatment in some embodiments. In some embodiments, treatment methods comprise administering to a subject a therapeutically effective amount of a composition of the invention. The administering step may consist of a single administration or may comprise a series of administrations. The length of the treatment period depends on a variety of factors, such as the severity of the condition, the age of the patient, the concentration of active agent in the composition, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some aspects, chronic administration may be required. For example, the compositions are administered to the subject in an amount, and for a duration, sufficient to treat the patient.

In the Summary of the Invention above, Detailed Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents aspects A, B, and C of an embodiment, it is understood that this also discloses particular embodiments including both aspects A and B, both aspects B and C, and both aspects A and C, as well as an embodiment with aspects A, B, and C.

Polyamine Compounds and Compositions

In some aspects, the invention provides a compound or composition that comprises, consists essentially of, or consists of a polyamine compound or composition used in any of the embodiments or aspects of the methods described herein.

In some aspects, the invention provides a compound selected from the group including an $A^{1-6}$ ring

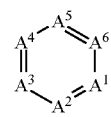

and a salt thereof;
wherein:

each $A^{1-6}$ ring member $A^1$, $A^2$, $A^3$, $A^4$, $A^5$, and $A^6$ is independently selected from the group including N, $CR^t$, $CR^a$, and $CR^b$; or, alternatively, a pair of adjacent $A^{1-6}$ ring members join to form an independently selected aryl, cycloalkyl, heterocyclyl, or heterocycloaryl $B^1$ ring that is fused with the $A^{1-6}$ ring at the pair's adjacent $A^{1-6}$ ring positions;

wherein two of the $A^{1-6}$ ring members are each an independently selected $CR^t$;

each $R^t$ is an independently selected $A^{7-11}$ ring

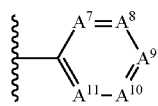

each $A^{7-11}$ ring member $A^7$, $A^8$, $A^9$, $A^{10}$, and $A^{11}$ is independently selected from the group including N, $CR^t$, $CR^a$, and $CR^b$; or, alternatively, a pair of adjacent $A^{7-11}$ ring members join to form an independently selected aryl, cycloalkyl, heterocyclyl, or heterocycloaryl $B^2$ ring that is fused with the $A^{7-11}$ ring at the pair's adjacent $A^{7-11}$ ring positions;

wherein for each $R^t$, one $A^{7-11}$ ring member is an independently selected $CR^a$;

each $B^1$ or $B^2$ ring, if present, is optionally substituted with up to one $R^a$ group and with up to three independently selected $R^5$ groups;

each $R^a$ is a member independently selected from the group including

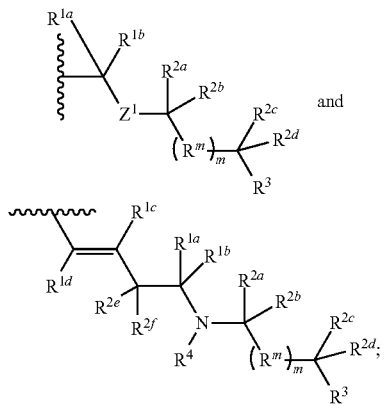

each $R^{1a}$, $R^{1b}$, $R^{1c}$, and $R^{1d}$ is a member independently selected from the group including hydrogen, fluoro, alkyl, and fluoroalkyl; or, alternatively, an $R^{1a}$ and an $R^{1b}$ join to form an oxo group;

each $R^{2a}$, $R^{2b}$, $R^{2c}$, $R^{2d}$, $R^{2e}$, and $R^{2f}$ is a member independently selected from the group including hydrogen, alkyl, fluoroalkyl, alkenyl, alkynyl, aryl, heteroaryl, arylalkyl, or heteroarylalkyl; alternatively, a pair of $R^2$ members from the same $R^a$ group independently selected from the group $R^{2a}$ and $R^{2b}$, $R^{2c}$ and $R^{2d}$, and $R^{2e}$ and $R^{2f}$ join to form a member independently selected from the group including spirocycloalkyl, spiroheterocycyl, and oxo; or, alternatively, an $R^{2a}$ and an $R^{2c}$ from the same $R^a$ group join to form a ring independently selected from the group including cycloalkyl and heterocycyl;

each $R^m$ is a member independently selected from the group including $-CR^{2a}R^{2b}-$, $-CR^{2c}R^{2d}-$, $-C(R^{2a})=(R^{2b})-$, $-CC-$, and $-C(R^{2a})(R^{2b})-L-C(R^{2c})(R^{2d})-$;

each m is an integer independently selected from 1 to 20;

each L is a member independently selected from the group including a bond, $-O-$, $-C(O)O-$, $-NR^4-$, $-NR^4C(O)-$, and $-C(O)NR^4-$;

each $R^3$ is a member independently selected from the group including $-Z^1-R^4$, $-Z^1-Y^1-R^4$, $-Z^1-Y^1-Y^2-R^4$, and $-Z^1-Y^1-Y^2-Y^3-R^4$;

each $R^4$ is a member independently selected from the group including hydrogen, alkyl, fluoroalkyl, alkenyl, alkynyl, aryl, cycloalkyl, heteroaryl, arylalkyl, cycloalkylalkyl, and heteroarylalkyl; or, alternatively, for an $-N(R^4)_2$ group, one of the two $R^4$ in the group is a member selected from the group including $-(CO)OR^{6a}-$, $-(CO)N(R^{6a})(R^{6b})$, and $-C(NR^{6a})N(R^{6b})(R^{6c})$; or, alternatively, for an $-N(R^4)_2$ group, the two $R^4$ groups join to form a heterocyclic ring;

each $Y^1$, $Y^2$, and $Y^3$ is an independently selected group of Formula IA:

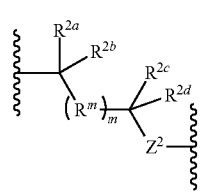

IA each $Z^1$ and $Z^2$ is a member independently selected from the group including $-N(R^4)-$ and $-O-$; and each $R^b$ is a member independently selected from hydrogen or an $R^5$;

each $R^5$ is a member independently selected from the group including alkyl, hydroxyl, alkoxy, aminoalkoxy, alkylamino, alkylaminoalkoxy, alkenyl, alkynyl, aryl, aryloxy, arylamino, cycloalkyl, cycloalkoxy, cycloalkylalkoxy, cycloalkylamino, cycloalkylalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino; hydroxyalkyl, aminoalkyl, and alkylaminoalkyl;

each $R^{6a}$, $R^{6c}$, and $R^{6c}$ is a member independently selected from the group including hydrogen, alkyl, fluoroalkyl, alkenyl, alkynyl, aryl, heteroaryl, cycloalkyl, arylalkyl, heteroarylalkyl, and cycloalkylalkyl; or, alternatively, two $R^{6n}$ members $R^{6a}$ and $R^{6b}$ or $R^{6a}$ and $R^{6c}$ join to form a heterocycyl ring;

wherein the polyamine compound comprises at least two primary or secondary amino groups. wherein the polyamine compound comprises at least two primary or secondary amino groups.

In some aspects, the compound is selected from the group including

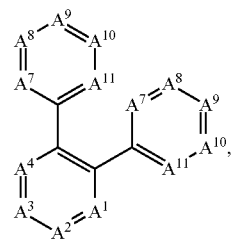

-continued

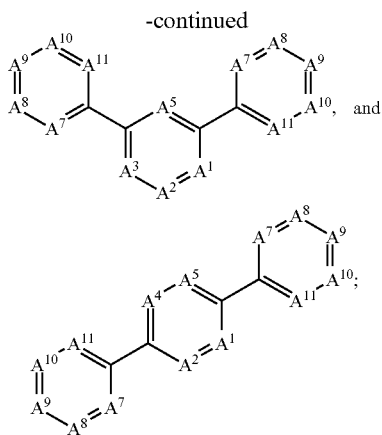

or a salt thereof.

In some aspects, the compound is

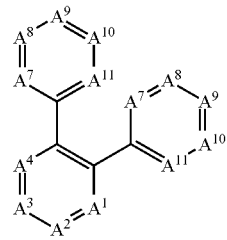

or a salt thereof.

In some aspects, the compound is

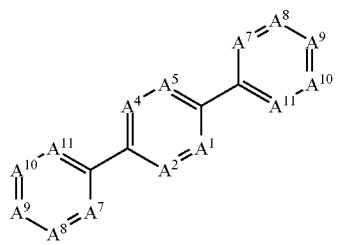

or a salt thereof.

In some aspects, the compound is

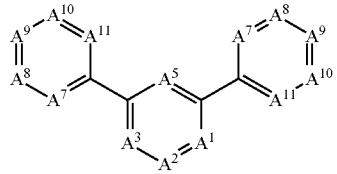

or a salt thereof.

In some aspects, at least one $A^9$ is a $CR^a$. In some aspects, each $A^9$ is a $CR^a$ (e.g., the pair of $A^9$ members are both the same $CR^a$).

In some aspects, $A^2$ is $CR^b$. In some specific aspects, the $A^2$ $R^b$ is selected from the group including alkyl, alkoxy, cylcloalkyl, cycloalkoxy, arylalkyl, and arylalkoxy. In some more specific aspects, the $A^2$ $R^b$ is selected from the group including alkyl, alkoxy, and arylalkoxy.

In some aspects, the $A^2$ $R^b$ is alkoxy. In some more specific aspects, the $A^2$ $R^b$ alkoxy is selected from the group including methoxy, ethoxy, n-propoxy, isopropoxy, n-butoxy, iso-butoxy, t-butoxy, n-pentoxy, and isopentoxy.

In some aspects, the $A^2$ $R^b$ is alkyl (e.g., lower alkyl). In some more specific aspects, the $A^2$ $R^b$ alkyl is selected from the group including methyl, ethyl, n-propyl, isopropyl, n-butyl, iso-butyl, t-butyl, n-pentyl, and isopentyl. In some more specific aspects, the $A^2$ $R^b$ alkyl is t-butyl.

In some aspects, at least one $A^{1-6}$ ring member is $CR^b$. In some aspects, at least one of $A^1$, $A^2$, or $A^3$ is $CR^b$.

In some aspects, at least one $A^{7-11}$ ring member is $CR^b$. In some aspects, at least one of $A^8$ or $A^{10}$ is $CR^b$. In some aspects, a pair of $A^{7-11}$ ring members is $CR^b$ (e.g., both $A^8$ member or both $A^{10}$ members).

In some specific aspects, at least one $R^b$ is selected from the group including alkyl, alkoxy, cylcloalkyl, cycloalkoxy, arylalkyl, and arylalkoxy. In some more specific aspects, said $R^b$ is selected from the group including alkyl, alkoxy, and arylalkoxy.

In some aspects, at least one $R^b$ is alkoxy. In some more specific aspects, said $R^b$ alkoxy is selected from the group including methoxy, ethoxy, n-propoxy, isopropoxy, n-butoxy, iso-butoxy, t-butoxy, n-pentoxy, and isopentoxy.

In some aspects, at least one $R^b$ is alkyl (e.g., lower alkyl). In some more specific aspects, said $R^b$ alkyl is selected from the group including methyl, ethyl, n-propyl, isopropyl, n-butyl, iso-butyl, t-butyl, n-pentyl, and isopentyl. In some more specific aspects, said $R^b$ alkyl is t-butyl.

In some aspects, at least one $A^9$ is a $CR^a$. In some aspects, each each $R^a$ is an independently selected

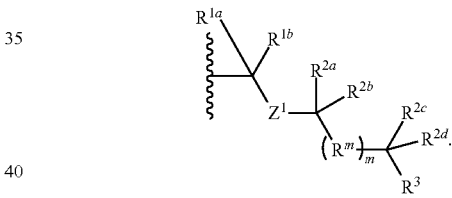

In some aspects, each $A^{7-11}$ member is independently selected from the group including $CR^a$ and $CR^b$. In some aspects, wherein each $A^{1-6}$ member is independently selected from the group consisting of $CR^t$, $CR^a$ and $CR^b$.

In some aspects, the compound comprises two independently selected $CR^a$. In some aspects, wherein the compound comprises three independently selected $CR^a$.

In some aspects, each $R^{1a}$, $R^{1b}$, $R^{1c}$, and $R^{1d}$ is a member independently selected from the group including hydrogen, fluoro, alkyl, and fluoroalkyl. In some aspects, each $R^{1a}$, $R^{1b}$, $R^{1c}$, and $R^{1d}$ is a member independently selected from hydrogen and alkyl. In some aspects, each $R^{1a}$, $R^{1b}$, $R^{1c}$, and $R^{1d}$ is hydrogen.

In some aspects, each $R^{1a}$ and $R^{1b}$ is a member independently selected from the group including hydrogen, fluoro, alkyl, and fluoroalkyl. In some aspects, each $R^{1a}$ and $R^{1b}$ is a member independently selected from hydrogen and alkyl. In some aspects, each $R^{1a}$ and $R^{1b}$ is hydrogen.

In some aspects, each $R^{2a}$, $R^{2b}$, $R^{2c}$, $R^{2d}$, $R^{2e}$, and $R^{2f}$ is a member independently selected from the group including hydrogen, alkyl, fluoroalkyl, alkenyl, alkynyl, aryl, heteroaryl, arylalkyl, and heteroarylalkyl. In some aspects, $R^{2a}$, $R^{2b}$, $R^{2c}$, $R^{2d}$, $R^{2e}$, and $R^{2f}$ is a member independently selected from hydrogen, alkyl, fluoroalkyl, and arylalkyl. In some aspects, each $R^{2a}$, $R^{2b}$, $R^{2c}$, $R^{2d}$, $R^{2e}$, and $R^{2f}$ is a member independently selected from hydrogen, alkyl, and fluoroalkyl. In some aspects, each $R^{2a}$, $R^{2b}$, $R^{2c}$, $R^{2d}$, $R^{2e}$, and $R^{2f}$ is hydrogen.

In some aspects, each $R^{2a}$, $R^{2b}$, $R^{2c}$, and $R^{2d}$ is a member independently selected from hydrogen, alkyl, and fluoroalkyl. In some aspects, each $R^{2a}$, $R^{2b}$, $R^{2c}$, and $R^{2d}$ is a member independently selected from hydrogen, alkyl, fluoroalkyl, and arylalkyl. In some aspects, each $R^{2a}$, $R^{2b}$, $R^{2c}$, and $R^{2d}$ is a member independently selected from hydrogen, alkyl, and fluoroalkyl. In some aspects, each $R^{2a}$, $R^{2b}$, $R^{2c}$, and $R^{2d}$ is hydrogen.

In some aspects, each m is an integer independently selected from 1 to 8. In some aspects, each m is an integer independently selected from 1 to 6. In some aspects, each m is an integer independently selected from 1 to 3.

In some aspects, each m is 1. In some aspects, at least one m is 1. In some aspects, each m is 2. In some aspects, at least one m is 2.

In some aspects, each L is a member independently selected from the group including a bond, —O—, and —NR$^4$—. In some aspects, each L is a bond.

In some aspects, each $R^3$ is a member independently selected from the group including —Z$^1$—R$^4$ and —Z$^1$—Y$^1$—R$^4$. In some aspects, each $R^3$ is an independently selected —Z$^1$—Y$^1$—R$^4$.

In some aspects, each $R^4$ is a member independently selected from the group including hydrogen, alkyl, fluoroalkyl, alkenyl, alkynyl, aryl, cycloalkyl, arylalkyl, cycloalkylalkyl, and heteroarylalkyl. In some aspects, each $R^4$ is a member independently selected from the group including hydrogen, alkyl, fluoroalkyl, alkenyl, alkynyl, arylalkyl, and cycloalkylalkyl. In some aspects, each $R^4$ is a member independently selected from the group including hydrogen, alkyl, arylalkyl, and cycloalkylalkyl.

In some aspects, for each —N(R$^4$)$_2$ group (e.g., the terminal amine for a polyamine side chain), one of the R$^4$ is a member independently selected from the group including alkyl, fluoroalkyl, alkenyl, alkynyl, aryl, cycloalkyl, heteroaryl, arylalkyl, cycloalkylalkyl, and heteroarylalkyl. In some more specific aspects, said R$^4$ is a member independently selected from the group including alkyl, arylalkyl, and cycloalkylalkyl. In some more specific aspects, said R$^4$ is a member independently selected from the group including n-butyl, isobuyl, 2-ethylbutyl, 2-methylbutyl, 3-methylbutyl, n-hexyl, isohexyl, and 2-ethylhexyl.

In some aspects, for each —N(R$^4$)$_2$ group (e.g., the terminal amine for a polyamine side chain), the —N(R$^4$)$_2$ group is —NH(R$^4$), and said R$^4$ is a member independently selected from the group including alkyl, fluoroalkyl, alkenyl, alkynyl, aryl, cycloalkyl, heteroaryl, arylalkyl, cycloalkylalkyl, and heteroarylalkyl. In some more specific aspects, said R$^4$ is a member independently selected from the group including alkyl, arylalkyl, and cycloalkylalkyl. In some more specific aspects, said R$^4$ is a member independently selected from the group including n-butyl, isobuyl, 2-ethylbutyl, 2-methylbutyl, 3-methylbutyl, n-hexyl, isohexyl, and 2-ethylhexyl.

In some aspects, at least one pair of R$^4$ (e.g., the terminal R$^4$ of two polyamine side chains) are both a member selected from the group including alkyl, arylalkyl, and cycloalkylalkyl. In some more specific aspects, said at least one pair of R$^4$ are both an alkyl (e.g., the same alkyl group).

In some aspects, each R$^4$ is a member independently selected from the group including hydrogen, alkyl, fluoroalkyl, alkenyl, alkynyl, aryl, heteroaryl, arylalkyl, and heteroarylalkyl; or, alternatively, for a —N(R$^4$)$_2$ group, one of the two R$^4$ in the group is a member selected from —(CO) OR$^{6a}$—, (CO)N(R$^{6a}$)(R$^{6c}$), and —C(NR$^{6a}$)N(R$^{6c}$)(R$^{6c}$); and each $R^b$ is a member independently selected from the group including hydrogen, alkyl, hydroxyl, alkoxy, alkylamino, alkenyl, alkynyl, aryl, aryloxy, arylamino, cycloalkyl, cycloalkoxy, cycloalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino, hydroxyalkyl, aminoalkyl, and alkylaminoalkyl.

In some aspects, each $R^b$ is a member independently selected from the group including hydrogen, alkyl, hydroxyl, alkoxy, alkylamino, alkenyl, alkynyl, aryl, aryloxy, arylamino, cycloalkyl, cycloalkoxy, cycloalkylamino, heterocyclyl, heterocycyloxy, heterocycylamino, halo, haloalkyl, fluoroalkyloxy, heteroaryl, heteroaryloxy, heteroarylamino, arylalkyl, arylalkyloxy, arylalkylamino, heteroarylalkyl, heteroarylalkyloxy, heteroarylalkylamino, hydroxyalkyl, aminoalkyl, and alkylaminoalkyl. In some aspects, each $R^b$ is a member independently selected from the group including hydrogen, alkyl, hydroxyl, alkoxy, aminoalkoxy, alkylamino, alkylaminoalkoxy, aryl, aryloxy, cycloalkyl, cycloalkoxy, cycloalkylalkoxy, halo, fluoroalkyl, fluoroalkyloxy, heteroaryl, arylalkyl, arylalkyloxy, hydroxyalkyl, aminoalkyl, and alkylaminoalkyl. In some aspects, each $R^b$ is a member independently selected from the group including hydrogen, alkyl, hydroxyl, alkoxy, aminoalkoxy, alkylaminoalkoxy, aryl, aryloxy, cycloalkylalkoxy, halo, fluoroalkyl, fluoroalkyloxy, arylalkyloxy, and hydroxyalkyl. In some aspects, each $R^b$ is a member independently selected from the group including hydrogen, alkyl, hydroxyl, alkoxy, aryl, aryloxy, halo, fluoroalkyl, and fluoroalkyloxy.

In some aspects, each $Z^1$ and $Z^2$ is an independently selected —N(R$^4$)— (e.g., —NH—).

In some aspects, each $R^{6a}$, $R^{6b}$, and $R^{6c}$ is a member independently selected from the group including hydrogen, alkyl, fluoroalkyl, alkenyl, alkynyl, aryl, heteroaryl, cycloalkyl, arylalkyl, heteroarylalkyl, and cycloalkylalkyl. In some aspects, each $R^{6a}$, $R^{6b}$, and $R^{6c}$ is a member independently selected from the group including hydrogen, alkyl, fluoroalkyl, alkenyl, alkynyl, aryl, and arylalkyl. In some aspects, each $R^{6a}$, $R^{6c}$, and $R^{6c}$ is a member independently selected from the group including hydrogen and alkyl.

In some aspects, each $R^a$ is independently a group of Formula II:

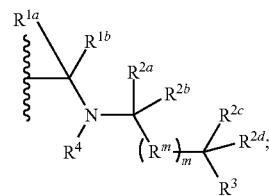

each $R^{1a}$, $R^{1b}$, $R^{1c}$, and $R^{1d}$ is a member independently selected from the group including hydrogen, fluoro, alkyl, and fluoroalkyl;

each $R^{2a}$, $R^{2b}$, $R^{2c}$, $R^{2d}$, $R^{2e}$, and $R^{2f}$ is a member independently selected from the group including hydrogen, alkyl, fluoroalkyl, alkenyl, alkynyl, aryl, heteroaryl, arylalkyl, and heteroarylalkyl;

each m is an integer independently selected from 1 to 2;
each $R^3$ is an independently selected —Z$^1$—Y$^1$—R$^4$; and
each $Z^1$ and $Z^2$ is an independently selected NR$^4$.

In some aspects, each $R^a$ is an independently selected group of Formula III:

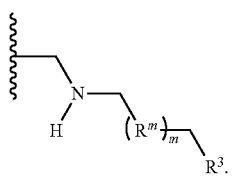

In some aspects, from 1 to 3 $R^b$ are selected from the group including alkyl, hydroxy, alkoxy, cycloalkoxy, and arylalkoxy.

In some aspects, $R^m$ is —$CH_2$—.

In some aspects, m is 1.

In some aspects, $R^a$ is —$CH_2[NH(CH_2)_3]_2NH_2$.

In some aspects, each $R^4$ is a member independently selected from hydrogen and alkyl.

In some aspects, the polyamine compound comprises at least four primary or secondary amino groups. In some aspects, the polyamine compound comprises at least six primary or secondary amino groups.

In some aspects, $R^m$ is —$CH_2$—. In some aspects, $R^a$ is —$CH_2[NH(CH_2)_n]_pNH_2$; each n is an integer independently selected from 3 to 12; and each p is an integer independently selected from 1 to 3. In some aspects, m is 1. In some aspects, each m is 1. In some aspects, at least one m is 1. In some aspects, each m is 2. In some aspects, at least one m is 2.

In some aspects, $R^5$ is hydrogen. In some aspects, $L^1$ is selected from a bond and O. In some aspects, $R^m$ is —$CH_2$—. In some aspects, m is 1. In some aspects, each m is 1. In some aspects, at least one m is 1. In some aspects, each m is 2. In some aspects, at least one m is 2.

In some aspects, $R^a$ is —$CH_2[NH(CH_2)_n]_pNH_2$; each n is an integer independently selected from 3 to 12; and each p is an integer independently selected from 1 to 3.

In some aspects, $R^a$ is —$CH_2[NH(CH_2)_n]_pNHR^4$; each n is an integer independently selected from 3 to 12; and each p is an integer independently selected from 1 to 3. In some aspects, n is 3. In some aspects, said $R^4$ is alkyl, cycloalkyl, or arylalkyl; preferably, $R^4$ is alkyl. In some aspects, said $R^4$ is isobutyl or hexyl.

In some aspects, $R^a$ is —$CH_2[NH(CH_2)_n]_pNHR^4$; each n is an integer independently selected from 3 to 12; and each p is an integer independently selected from 1 to 3. Preferably, n is 3. More preferably, said $R^4$ is not hydrogen.

In some aspects, the polyamine compound comprises at least four primary or secondary amino groups. In some aspects, the polyamine compound comprises at least six primary or secondary amino groups. In some aspects, the polyamine compound comprises at least eight primary or secondary amino groups. In some aspects, the polyamine compound comprises at least nine primary or secondary amino groups.

In some aspects, the polyamine compound is a hydrogen halide salt (e.g., a hydrochloride salt, such as a hydrochloride at each of the compound's amino groups).

In some aspects, the polyamine compound is

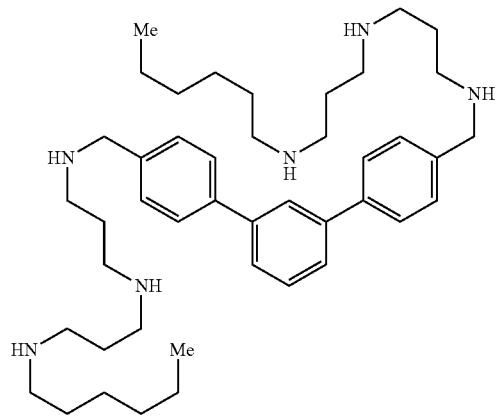 [SMILES: CCCCCCNCCCNCCCNCc1ccc(-c2cccc(-c3ccc(CNCCCNCCCNCCCCCC)cc3)c2)cc1]

or a salt thereof (e.g., a hydrogen halide salt, such as the hexahydrochloride).

In some aspects, the polyamine compound is a structure of Example 1 or a salt thereof.

In some aspects, each $R^{2a}$, $R^{2b}$, $R^{2c}$, $R^{2d}$, $R^{2e}$, and $R^{2f}$ is a member independently selected from the group including hydrogen, alkyl, fluoroalkyl, alkenyl, alkynyl, aryl, heteroaryl, arylalkyl, and heteroarylalkyl; alternatively, a pair of $R^{2n}$ members from the $R^a$ group independently selected from the group $R^{2a}$ and $R^{2b}$, $R^{2c}$ and $R^{2d}$, and $R^{2e}$ and $R^{2f}$ join to form a ring independently selected from the group including spirocycloalkyl and spiroheterocycyl; or, alternatively, the $R^{2a}$ and the $R^{2c}$ from the $R^a$ group join to form a ring independently selected from the group including cycloalkyl and heterocycyl;

each m is an integer independently selected from 1 to 3;

each $R^3$ is a member independently selected from the group including —$Z^1$—$Y^1$—$R^4$ and —$Z^1$—$Y^1$—$Y^2$—$R^4$; and each $Z^1$ and $Z^2$ is an independently selected $NR^4$.

In some aspects, $R^4$ is a member independently selected from the group including hydrogen, alkyl, fluoroalkyl, alkenyl, alkynyl, aryl, cycloalkyl, heteroaryl, arylalkyl, cycloalkylalkyl, and heteroarylalkyl. In some aspects, at least one $R^4$ is a member independently selected from the group including alkyl, fluoroalkyl, alkenyl, alkynyl, aryl, cycloalkyl, heteroaryl, arylalkyl, cycloalkylalkyl, and heteroarylalkyl. In some aspects, at least one $R^4$ is alkyl (e.g., lower alkyl; isobutyl; butyl; propyl; isopropyl). In some aspects, at least one $R^4$ is alkenyl (e.g., allyl; methallyl). In some aspects, at least one $R^4$ is alkynyl (e.g., propargyl). In some aspects, at least one $R^4$ is cycloalkylalkyl (e.g., cyclohexylmethyl). In some aspects, at least one $R^4$ is arylalkyl. In some aspects, at least one $R^4$ is heteroarylalkyl.

In some aspects, at least one $R^b$ is a member independently selected from the group including alkyl, hydroxyl, alkoxy, aminoalkoxy, alkylamino, alkylaminoalkoxy, cycloalkyl, cycloalkoxy, cycloalkylalkoxy, halo, fluoroalkyl, fluoroalkyloxy, arylalkyl, arylalkyloxy, heteroaryl, heteroaryloxy, heteroarylalkyloxy, hydroxyalkyl, aminoalkyl, and alkylaminoalkyl. In some aspects, at least one $R^b$ is a member independently selected from hydroxyl, alkoxy, aminoalkoxy, alkylaminoalkoxy, cycloalkoxy, cycloalkylalkoxy, fluoroalkyloxy, arylalkyloxy, heteroaryloxy, heteroarylalkyloxy, hydroxyalkyl, aminoalkyl, and alkylaminoalkyl. In some aspects, at least one $R^b$ is a member independently selected from the group including alkyl, hydroxyl, alkoxy, halo, fluoroalkyl, and fluoroalkyloxy.

In some aspects, at least one $R^b$ is a member independently selected from the group including hydroxyl, alkoxy, and fluoroalkyloxy. In some aspects, at least one $R^b$ is hydroxy. In some aspects, at least one $R^b$ is alkoxy. In some aspects, at least one $R^b$ is fluoroalkyloxy. In some aspects, at least one $R^b$ is a member independently selected from the group including aminoalkoxy and alkylaminoalkoxy. In some aspects, at least one $R^b$ is aminoalkoxy. In some aspects, at least one $R^5$ is alkylaminoalkoxy.

In some aspects, at least one $R^b$ is a member independently selected from the group including cycloalkoxy and cycloalkylalkoxy. In some aspects, at least one $R^b$ is cycloalkoxy. In some aspects, at least one $R^b$ is cycloalkylalkoxy. In some aspects, at least one $R^b$ is arylalkyloxy. In some aspects, at least one $R^b$ is a member independently selected from the group including heteroaryloxy and heteroarylalkyloxy. In some aspects, at least one $R^b$ is heteroaryloxy. In some aspects, at least one $R^b$ is heteroarylalkyloxy.

In some aspects, at least one $R^b$ is a member independently selected from the group including hydroxyalkyl, aminoalkyl, and alkylaminoalkyl. In some aspects, at least one $R^b$ is hydroxyalkyl. In some aspects, at least one $R^b$ is aminoalkyl or alkylaminoalkyl. In some aspects, at least one $R^b$ is aminoalkyl. In some aspects, at least one $R^5$ is alkylaminoalkyl.

In some aspects, each $R^b$ is a member independently selected from hydrogen, alkyl, hydroxyl, alkoxy, alkylamino, aryl, aryloxy, heterocyclyl, halo, fluoroalkyl, fluoroalkyloxy, heteroaryl, arylalkyl, arylalkyloxy, hydroxyalkyl, aminoalkyl, and alkylaminoalkyl.

In some aspects, at least one $R^5$ is a member independently selected from the group including alkyl, hydroxyl, alkoxy, aminoalkoxy, alkylamino, alkylaminoalkoxy, cycloalkyl, cycloalkoxy, cycloalkylalkoxy, halo, fluoroalkyl, fluoroalkyloxy, arylalkyl, arylalkyloxy, heteroaryl, heteroaryloxy, heteroarylalkyloxy, hydroxyalkyl, aminoalkyl, and alkylaminoalkyl. In some aspects, at least one $R^5$ is a member independently selected from hydroxyl, alkoxy, aminoalkoxy, alkylaminoalkoxy, cycloalkoxy, cycloalkylalkoxy, fluoroalkyloxy, arylalkyloxy, heteroaryloxy, heteroarylalkyloxy, hydroxyalkyl, aminoalkyl, and alkylaminoalkyl. In some aspects, at least one $R^5$ is a member independently selected from the group including alkyl, hydroxyl, alkoxy, halo, fluoroalkyl, and fluoroalkyloxy. In some aspects, each $R^5$ is hydrogen.

In some aspects, at least one $R^5$ is a member independently selected from the group including hydroxyl, alkoxy, and fluoroalkyloxy. In some aspects, at least one $R^5$ is hydroxy. In some aspects, at least one $R^5$ is alkoxy. In some aspects, at least one $R^5$ is fluoroalkyloxy. In some aspects, at least one $R^5$ is a member independently selected from the group including aminoalkoxy and alkylaminoalkoxy. In some aspects, at least one $R^5$ is aminoalkoxy. In some aspects, at least one $R^5$ is alkylaminoalkoxy.

In some aspects, at least one $R^5$ is a member independently selected from the group including cycloalkoxy and cycloalkylalkoxy. In some aspects, at least one $R^5$ is cycloalkoxy. In some aspects, at least one $R^5$ is cycloalkylalkoxy. In some aspects, at least one $R^5$ is arylalkyloxy. In some aspects, at least one $R^5$ is a member independently selected from the group including heteroaryloxy and heteroarylalkyloxy. In some aspects, at least one $R^5$ is heteroaryloxy. In some aspects, at least one $R^5$ is heteroarylalkyloxy.

In some aspects, at least one $R^5$ is a member independently selected from the group including hydroxyalkyl, aminoalkyl, and alkylaminoalkyl. In some aspects, at least one $R^5$ is hydroxyalkyl. In some aspects, at least one $R^5$ is aminoalkyl or alkylaminoalkyl. In some aspects, at least one $R^5$ is aminoalkyl. In some aspects, at least one $R^5$ is alkylaminoalkyl.

In some aspects, each $R^5$ is a member independently selected from hydrogen, alkyl, hydroxyl, alkoxy, alkylamino, aryl, aryloxy, heterocyclyl, halo, fluoroalkyl, fluoroalkyloxy, heteroaryl, arylalkyl, arylalkyloxy, hydroxyalkyl, aminoalkyl, and alkylaminoalkyl.

In some aspects, each $Z^1$ and $Z^2$ is an independently selected $-N(R^4)-$; and each $R^{6a}$, $R^{6b}$, and $R^{6c}$ is a member independently selected from the group including hydrogen and alkyl.

In some aspects, each $R^{1a}$, $R^{1b}$, $R^{1c}$, and $R^{1d}$ is hydrogen; each $R^{2a}$, $R^{2b}$, $R^{2c}$, $R^{2d}$, $R^{2e}$, and $R^{2f}$ is hydrogen; each $R^3$ is an independently selected $-Z^1-Y^1-R^4$; and each L is a member independently selected from the group including a bond and $-O-$.

In some aspects, at least one $R^4$ is a member independently selected from the group including alkyl, arylalkyl, and cycloalkylalkyl. In some aspects, at least one $R^4$ is alkyl (e.g., isobutyl). In some aspects, at least one $R^4$ is arylalkyl. In some aspects, at least one $R^4$ is cycloalkylalkyl (e.g., cyclohexylmethyl).

In some aspects, at least one $R^4$ is a member independently selected from the group including alkyl, arylalkyl, and cycloalkylalkyl.

In some aspects, $R^a$ is $-CH_2[NH(CH_2)_3]_2NH(R^4)$.

In some aspects, $R^a$ is $-CH_2[NH(CH_2)_n]_pNR^4$; wherein each n is an integer independently selected from 3 to 12; and wherein each p is an integer independently selected from 1 to 3. In some aspects, n is 3 or 4. In some aspects, $R^4$ is lower alkyl (e.g., isobutyl). In some aspects, n is 3 or 4, and $R^4$ is isobutyl.

In some aspects, each $R^{2a}$, $R^{2b}$, $R^{2c}$, and $R^{2d}$ is a member independently selected from the group including hydrogen, alkyl, and fluoroalkyl; and the polyamine compound comprises at least four primary or secondary amino groups.

In some aspects, m is 1 or 2. In some aspects, L is a bond. In some aspects, m is 1 or 2, and L is a bond.

In some aspects, each $R^{1a}$ and $R^{1b}$ is a member independently selected from hydrogen, fluoro, alkyl, and fluoroalkyl.

In some aspects, each $R^{2a}$, $R^{2b}$, $R^{2c}$, and $R^{2d}$ is a member independently selected from hydrogen, alkyl, fluoroalkyl, aryl, and arylalkyl.

In some aspects, each $R^m$ is a member independently selected from $-CR^{2a}R^{2b}-$ and $-C(R^{2a})(R^{2b})-L^2-C(R^{2c})(R^{2d})-$.

In some aspects, each $R^{6a}$, $R^{6b}$, and $R^{6c}$ is a member independently selected from hydrogen and alkyl; wherein if $R^4$ is $-C(O)OR^{6a}$, $R^{6a}$ is alkyl.

In some aspects, each $L^1$ is a member independently selected from a bond and $-O-$; and each $L^2$ is a member independently selected from a bond, $-O-$, and $-NR^4-$.

In still some aspects, $R^2$ is hydrogen.

In some aspects, the compounds of the present invention are antimicrobial and provide triple action against bacteria and biofilms. Advantageously, the antimicrobial compounds of the present invention have specific activity against biofilms.

In some aspects, compounds of the present invention having increased numbers of chains, produce a more effective compound against *A. baumannii*. For example, compounds with four polyamine chains can be generated with Pd(II) mediated dimerization of 5-bromoisopthalaldehyde followed by reductive amination (FIG. 26).

In some aspects, the compounds of present invention combine a hydrophobic backbone with a cationic tail that have the functionality to inhibit biofilm formation, disrupt established biofilms, and kill the emerging planktonic bacteria. In some aspects, the polyamine compound may comprise a hydrophobic moiety head and at least one hydrophilic moiety tail comprising a polyamine group. When the polyamine compound comprises more than one hydrophilic moiety tails, the hydrophilic moiety tails may be the same, or alternatively, the hydrophilic moiety tails may be different.

In some embodiments, the antimicrobial composition may comprise a polyamine compound and at least one additive. Various additives may be used for the antimicrobial composition. By way of non-limiting examples, the additives may further enhance the dispersion of microorganisms in biofilms, impart the antimicrobial effect against the dispersed microorganisms, facilitate the application/administration of the antimicrobial composition to the biofilms, improve the stability of the antimicrobial composition, control the release/application rate of the antimicrobial composition to the biofilms, etc. Non-limiting examples of additives for further enhancing the antimicrobial effect may be biocide and other bactericide. By way of non-limiting examples, the additives for facilitating the administration of the antimicrobial composition may include a pharmaceutically acceptable carrier typically used for medical or pharmaceutical applications, an emulsifier or dispersant typically used for industrial applications.

In some embodiments, the invention presents an antimicrobial composition comprising a compound as set forth in any of the aspects and embodiments herein; and an excipient. In some aspects, the excipient is pharmaceutically acceptable.

The antimicrobial composition may be formulated to provide the desired level of antimicrobial effect on the biofilms by selecting a polyamine compound and other additives as well as by adjusting the amount of each component in the antimicrobial composition. In some embodiments, the antimicrobial composition may be formulated to inhibit the formation of biofilms. In some embodiment, the antimicrobial composition may be formulated to disrupt the biofilms. In still other embodiments, the antimicrobial composition may be formulated to eradicate substantially all microorganisms in the biofilms.

Any suitable amount of polyamine can be used in the compositions and methods of the invention. In general, the polyamines are used in concentrations ranging from about 1 ppm to about 100,000 ppm, or higher. The concentration of a polyamine used in a composition or method of the invention can be, for example, from about 1 to about 100,000 ppm, or from about 10 to about 10,000 ppm, or from about 100 to about 1,000 ppm, or from about 1 to about 100 ppm, or from about 1,000 to about 10,000 ppm, or from about 10,000 to about 100,000 ppm. The concentration of a polyamine can be about 1; 2; 3; 4; 5; 6; 7; 8; 9; 10; 15; 20; 25; 30; 35; 40; 45; 50; 55; 60; 65; 70; 75; 80; 85; 90; 95; 100; 125; 150; 175; 200; 225; 250; 275; 300; 325; 350; 375; 400; 425; 450; 475; 500; 525; 550; 575; 600; 625; 650; 675; 700; 725; 750; 775; 800; 825; 850; 875; 900; 925; 950; 975; 1000; 1500; 2000; 2500; 3000; 3500; 4000; 4500; 5000; 5500; 6000; 6500; 7000; 7500; 8000; 8500; 9000; 9500; 10,000; 12,500; 15,000; 17,500; 20,000; 22,500; 25,000; 27,500; 30,000; 32,500; 35,000; 37,500; 40,000; 42,500; 45,000; 47,500; 50,000; 52,500; 55,000; 57,500; 60,000; 62,500; 65,000; 67,500; 70,000; 72,500; 75,000; 77,500; 80,000; 82,500; 85,000; 87,500; 90,000; 92,500; 95,000; 97,500; or about 100,000 ppm. Other concentrations of polyamines can be useful in the compositions and methods of the invention, depending in part on factors including the specific polyamine used, the presence of potentiating agents if any, or the species of microorganisms that are targeted.

As discussed above, the exemplary polyamine compounds and compositions shown herein are not intended to be limiting.

Synthesis

A general procedure for synthesis is provided in Example 1.

The synthesis of diaminopropane substituted backbones is straightforward from the known mono-Boc protected diaminopropane and commercially available aldehydes. This three-step synthetic procedure proceeds via reductive amination (Baxter, E. W. & Reitz, A. B. Reductive Aminations of Carbonyl Compounds with Borohydride and Borane Reducing Agents. *Org Reac* 1, 59 (2004)) and acidic removal of the Boc group. Norspermidine analog $R^a$ side chains can be prepared in a similar manner from the mono-Boc protected norspermidine. No purification is required until a final recrystallization of the HCl salt, which has allowed easy preparation of these compounds on larger scale.

The method of synthesis may include reacting a polyamine with di-t-butyldicarbonate compound [(Boc)$_2$O] to protect at least one terminal amine group of the polyamine, while leaving at least one terminal amine group of the polyamine unprotected. The resulting Boc-polyamine having at least one unprotected terminal amine is reacted with a substituted aryl aldehyde. Then, the resulting product is reduced, such as by a hydride reducing agent (e.g., NaBH$_4$ or LiAlH$_4$) to provide a corresponding polyamine conjugate having the terminal amine group on at least one hydrophilic polyamine chain Boc-protected. The Boc-protected terminal amine group is then deprotected, such as by acid hydrolysis, to provide the polyamine compound a hydrophobic aryl group and at least one hydrophilic polyamine chain.

Applications and Related Compositions

As described herein, biofilms can also affect a wide variety of biological, medical, and processing operations. Methods and treatments using a polyamine compound, or a combination of a polyamine compound with another compound, may include killing, dispersing, treating, reducing biofilms or preventing or inhibiting biofilm formation.

In some embodiments, the invention provides a method for dispersing or killing a biofilm, the method comprising a step of treating the biofilm with an anti-biofilm composition, thereby effectively dispersing or killing the biofilm; wherein the method comprises, consists essentially of, or consists of using a polyamine compound or composition as set forth in any of the embodiments or aspects described herein.

In some aspects, the step of treating the biofilm with an anti-biofilm composition effectively disperses the biofilm.

In another embodiment, the invention provides a method for inhibiting formation of a biofilm, the method comprising a step of treating planktonic bacteria with a polyamine composition as set forth in any of the embodiments or aspects herein, thereby inhibiting incorporation of the planktonic bacteria into the biofilm.

In some embodiments, the polyamine compounds may exhibit enhanced antimicrobial effect on biofilms comprised of Gram-negative or Gram-positive bacteria. The polyamine compounds may exhibit enhanced antimicrobial effect on biofilms consisting of mycobacteria.

In some aspects, the method of killing, dispersing, dislodging, treating, or reducing biofilms, or preventing or inhibiting biofilm formation, includes contacting the biofilm with an effective amount of a composition of the present invention.

In some aspects, the formation of a biofilm is inhibited. In other aspects, a previously formed biofilm is dispersed. In still other aspects, substantially all of the cells comprising a biofilm are killed.

In some embodiments, the invention provides a method of killing, dispersing, treating, or reducing biofilms, or preventing or inhibiting biofilm formation, the method comprising contacting a biofilm or a surface having a biofilm disposed thereon with an effective amount of a polyamine compound.

In some aspects, a surface comprises a medical device, a wound dressing, a contact lens, or an oral device. In some aspects, the medical device is selected from a clamp, forceps, scissors, skin hook, tubing, needle, retractor, scaler, drill, chisel, rasp, saw, catheter, orthopedic device, artificial heart valve, prosthetic joint, voice prosthetic, stent, shunt, pacemaker, surgical pin, respirator, ventilator, and an endoscope and combinations thereof.

In some aspects, the method described herein comprises, consists essentially of, or consists of using the polyamine compound or composition described in any of the embodiments or aspects herein.

In some aspects, the invention provides a method that comprises, consists essentially of, or consists of using a polyamine compound or composition from any of the embodiments or aspects described herein.

In some embodiments, the invention provides a method for enhancing wound healing, the method comprising a step of treating a patient with a antibacterial composition, thereby enhancing healing of a wound in the patient;
    wherein the anti-biofilm composition comprises, consists essentially of, or consists of a polyamine compound selected from any of the embodiments or aspects described herein.

In some embodiments, the invention provides a method for dispersing or killing a biofilm, the method comprising a step of treating the biofilm with an anti-biofilm composition, thereby effectively dispersing or killing the biofilm;
    wherein the anti-biofilm composition comprises, consists essentially of, or consists of a polyamine compound selected from any of the embodiments or aspects described herein.

In some embodiments, the polyamine compound or combination of a polyamine compound and at least one other composition may be used to treat Gram negative and Gram positive bacteria (including strains that are resistant to conventional antibiotics), mycobacteria (including *Mycobacterium tuberculosis*), enveloped viruses, fungi and even transformed or cancerous cells.

The compounds, compositions, and methods described herein can be used to kill, disperse, treat, reduce biofilms, or prevent or inhibit biofilm formation. In exemplary methods, the biofilms are formed by biofilm-forming bacteria. The bacteria can be a gram-negative bacterial species or a gram-positive bacterial species. Nonlimiting examples of such bacteria include a member of the genus *Actinobacillus* (such as *Actinobacillus actinomycetemcomitans*), a member of the genus *Acinetobacter* (such as *Acinetobacter baumannii*), a member of the genus *Aeromonas*, a member of the genus *Bordetella* (such as *Bordetella pertussis, Bordetella bronchiseptica*, or *Bordetella parapertussis*), a member of the genus *Brevibacillus*, a member of the genus *Brucella*, a member of the genus *Bacteroides* (such as *Bacteroides fragilis*), a member of the genus *Burkholderia* (such as *Burkholderia cepacia* or *Burkholderia pseudomallei*), a member of the genus *Borelia* (such as *Borelia burgdorferi*), a member of the genus *Bacillus* (such as *Bacillus anthracis* or *Bacillus subtilis*), a member of the genus *Campylobacter* (such as *Campylobacter jejuni*), a member of the genus *Capnocytophaga*, a member of the genus *Cardiobacterium* (such as *Cardiobacterium hominis*), a member of the genus *Citrobacter*, a member of the genus *Clostridium* (such as *Clostridium tetani* or *Clostridium difficile*), a member of the genus *Chlamydia* (such as *Chlamydia trachomatis, Chlamydia pneumoniae*, or *Chlamydia psiffaci*), a member of the genus *Eikenella* (such as *Eikenella corrodens*), a member of the genus *Enterobacter*, a member of the genus *Escherichia* (such as *Escherichia coli*), a member of the genus *Francisella* (such as *Francisella tularensis*), a member of the genus *Fusobacterium*, a member of the genus *Flavobacterium*, a member of the genus *Haemophilus* (such as *Haemophilus ducreyi* or *Haemophilus influenzae*), a member of the genus *Helicobacter* (such as *Helicobacter pylori*), a member of the genus *Kingella* (such as *Kingella kingae*), a member of the genus *Klebsiella* (such as *Klebsiella pneumoniae*), a member of the genus *Legionella* (such as *Legionella pneumophila*), a member of the genus *Listeria* (such as *Listeria monocytogenes*), a member of the genus *Leptospirae*, a member of the genus *Moraxella* (such as *Moraxella catarrhalis*), a member of the genus *Morganella*, a member of the genus *Mycoplasma* (such as *Mycoplasma hominis* or *Mycoplasma pneumoniae*), a member of the genus *Mycobacterium* (such as *Mycobacterium tuberculosis* or *Mycobacterium leprae*), a member of the genus *Neisseria* (such as *Neisseria gonorrhoeae* or *Neisseria meningitidis*), a member of the genus *Pasteurella* (such as *Pasteurella multocida*), a member of the genus *Proteus* (such as *Proteus vulgaris* or *Proteus mirablis*), a member of the genus *Prevotella*, a member of the genus *Plesiomonas* (such as *Plesiomonas shigelloides*), a member of the genus *Pseudomonas* (such as *Pseudomonas aeruginosa*), a member of the genus *Providencia*, a member of the genus *Rickettsia* (such as *Rickettsia rickettsii* or *Rickettsia typhi*), a member of the genus *Stenotrophomonas* (such as *Stenotrophomonas maltophila*), a member of the genus *Staphylococcus* (such as *Staphylococcus aureus* or *Staphylococcus epidermidis*), a member of the genus *Streptococcus* (such as *Streptococcus viridans, Streptococcus pyogenes* (group A), *Streptococcus agalactiae* (group B), *Streptococcus bovis*, or *Streptococcus pneumoniae*), a member of the genus *Streptomyces* (such as *Streptomyces hygroscopicus*), a member of the genus *Salmonella* (such as *Salmonella enteriditis, Salmonella typhi*, or *Salmonella typhimurium*), a member of the genus *Serratia* (such as *Serratia marcescens*), a member of the genus *Shigella*, a member of the genus *Spirillum* (such as *Spirillum minus*), a member of the genus *Treponema* (such as *Treponema pallidum*), a member of the genus *Veillonella*, a member of the genus *Vibrio* (such as *Vibrio cholerae, Vibrio parahaemolyticus*, or *Vibrio vulnificus*), a member of the genus *Yersinia* (such as *Yersinia enter ocolitica, Yersinia pestis*, or *Yersinia pseudotuberculosis*), and a member of the genus *Xanthomonas* (such as *Xanthomonas maltophilia*).

In some embodiments, the biofilm exposed to the compounds, compositions, or methods of the present invention may comprise Gram-negative or Gram-positive bacteria. In some embodiments, the bacteria are mycobacteria.

In some aspects, the biofilm comprises an antibiotic-resistant bacterial species.

The antimicrobial compounds, compositions, and methods comprising a polyamine compound may be used to control, prevent or kill biofilms in various environments. In some embodiments, they may be used for treating biofilms in subjects that include human or other animals. In some embodiments, they may be used for treating biofilms in medical applications such as medical devices, wound dressings, contact lens, oral devices, etc. In some embodiments, they may be used for treating or preventing a biofilm-related disorder. In some embodiments, they may be used for treating biofilms in industrial applications such as oil pipelines, water pipelines, water treatment at manufacturing sites, industrial flush solution, industrial wash water, industrial coatings, etc. In some embodiments, they may be used for household and hygiene applications. In some embodiments, they may be used for agricultural applications, such as water remediation, crop treatment, etc. In some embodiments, they may be used for food preparation applications, such as meat sprays, fruit and vegetable sanitizers.

In some aspects, the method comprises a step of coating an object with the anti-biofilm composition. In some aspects, the method comprises a step of treating a contact lens with the anti-biofilm composition.

In some embodiments, the polyamine compound or combination of a polyamine compound and at least one other composition are directed for use in industrial applications, for example oil pipelines, water treatment, water pipelines, fracking water sanitation, milk production facility pipeline flush solution, oil fields, paper and pulp production, machining fluids, ship coatings, shipping, paint, handrail sanitizers, water filtration, biofouling and biocorrosion, natural gas pipeline treatment, HVAC units, etc.

In some embodiments, the polyamine compound or combination of a polyamine compound and at least one other composition are directed for use in household applications, for example, sanitizing wipes, cleansers, toilet bowl inserts, baby care products, toys, etc.

In some embodiments, the polyamine compound or combination of a polyamine compound and at least one other composition are directed for use in environmental applications, for example, agriculture, water remediation, water treatment, crop treatment, etc.

In some aspects, the method comprises a step of treating a pipe with the anti-biofilm composition. In some aspects, the method comprises a step of treating a heating or cooling tower with the anti-biofilm composition.

In some embodiments, the polyamine compound or combination of a polyamine compound and at least one other composition are directed for use in food production, for example, fruit and vegetable sanitizers, water systems in food production facilities, meat sprays, cooling system sanitizers, air filtration units, feed, packaging, etc.

In some aspects, the anti-biofilm composition is a paint.

In some aspects, the method comprises a step of treating a patient with a biofilm-related disorder. In some aspects, the patient is not immunocompromised. In some alternative aspects, the patient is immunocompromised (e.g., diabetic).

Some aspects of this disclosure is directed to methods of treating a biofilm-related disorder in a subject in need thereof, the method comprising administering to the subject an effective amount of a polyamine compound of the present invention.

In some embodiments, the composition is administered to a surface of the subject selected from the group of dermal and mucosal surfaces and combinations thereof. In other embodiments, the surface is an oral surface, a skin surface, a urinary tract surface, a vaginal tract surface, or a lung surface.

In some embodiments, the composition is administered to the subject via subcutaneous, intra-muscular, intra-peritoneal, intravenous, oral, nasal, or topical administration, and a combination thereof.

In some aspects, a subject is treated. A subject can be a mammal including, but not limited to, a primate (e.g., a monkey, such as a cynomolgous monkey, a chimpanzee, and a human). A subject can be a non-human animal such as a bird (e.g., a quail, chicken, or turkey), a farm animal (e.g., a cow, goat, horse, pig, or sheep), a pet (e.g., a cat, dog, or guinea pig, rat, or mouse), or laboratory animal (e.g., an animal model for a disorder). Non-limiting representative subjects can be a human infant, a pre-adolescent child, an adolescent, an adult, or a senior/elderly adult.

In some embodiments, the subject is a human.

In some instances, a subject in need of treatment can be one afflicted with one or more of the infections or disorders described herein. In some aspects, the subject is at risk of developing a biofilm on or in a biologically relevant surface, or already has developed such a biofilm. Such a subject at risk can be a candidate for treatment with a polyamine compound, or combination of a polyamine compound with another compound, in order to inhibit the development or onset of a biofilm-production-related disorder/condition or prevent the recurrence, onset, or development of one or more symptoms of a biofilm-related disorder or condition. Such a subject can be harboring an immature biofilm that is clinically evident or detectable to the skilled artisan, but that has not yet fully formed. A subject at risk of developing a biofilm can also be one in which implantation of an indwelling device, such as a medical device, is scheduled. The risk of developing a biofilm can also be due to a propensity of developing a biofilm-related disease (such as the presence of a channel transporter mutation associated with cystic fibrosis). In such subjects, a biofilm-related disorder can be at an early stage, e.g., no bacterial infection or biofilm formation is yet detected.

In some embodiments a biofilm-related disorder is selected from a wound with a bacterial infection, pneumonia, cystic fibrosis, otitis media, chronic obstructive pulmonary disease, and a urinary tract infection and combinations thereof. In other embodiments, the biofilm-related disorder is a medical device-related infection. In further embodiments, the biofilm-related disorder is a periodontal disease, such as gingivitis, periodontitis or breath malodor. In still further embodiments, the biofilm-related disorder is caused by bacteria. In some embodiments, the bacteria are Gram-negative or Gram-positive bacteria. In still other embodiments, the bacteria are of the genus *Actinobacillus, Acinetobacter, Aeromonas, Bordetella, Brevibacillus, Brucella, Bacteroides, Burkholderia, Borelia, Bacillus, Campylobacter, Capnocytophaga, Cardiobacterium, Citrobacter, Clostridium, Chlamydia, Eikenella, Enterobacter, Escherichia, Entembacter, Francisella, Fusobacterium, Flavobacterium, Haemophilus, Helicobacter, Kingella, Klebsiella, Legionella, Listeria, Leptospirae, Moraxella, Morganella, Mycoplasma, Mycobacterium, Neisseria, Pasteurella, Proteus, Prevotella, Plesiomonas, Pseudomonas, Providencia, Rickettsia, Stenotrophomonas, Staphylococcus, Streptococcus, Streptomyces, Salmonella, Serratia, Shigella, Spirillum, Treponema, Veillonella, Vibrio, Yersinia,* or *Xanthomonas.*

Non-limiting examples of biofilm-related disorders include otitis media, prostatitis, cystitis, bronchiectasis, bacterial endocarditis, osteomyelitis, dental caries, periodontal disease, infectious kidney stones, acne, Legionnaire's disease, chronic obstructive pulmonary disease (COPD), and cystic fibrosis. In one specific example, subjects with cystic fibrosis display an accumulation of biofilm in the lungs and digestive tract. Subjects afflicted with COPD, such as emphysema and chronic bronchitis, display a characteristic inflammation of the airways wherein airflow through such airways, and subsequently out of the lungs, is chronically obstructed.

Biofilm-related disorders can also encompass infections derived from implanted/inserted devices, medical device-related infections, such as infections from biliary stents, orthopedic implant infections, and catheter-related infections (kidney, vascular, peritoneal). An infection can also originate from sites where the integrity of the skin or soft tissue has been compromised. Non-limiting examples include dermatitis, ulcers from peripheral vascular disease, a burn injury, and trauma. For example, a Gram-positive bacterium, such as *S. pneumoniae*, can cause opportunistic infections in such tissues. The ability of *S. pneumoniae* to infect burn wound sites, e.g., is enhanced due to the breakdown of the skin, burn-related immune defects, and antibiotic selection.

In yet other embodiments, a biofilm-related disorder is pneumonia, cystic fibrosis, otitis media, chronic obstructive pulmonary disease, or a urinary tract infection. In some embodiments, the biofilm-related disorder is a medical device-related infection.

In other aspects, this disclosure features compounds, compositions, or methods, such as industrial, therapeutic or pharmaceutical compositions, comprising polyamine compounds in combination with one or more additional active compositions.

In some instances a polyamine compound can be administered alone or in combination with a second agent, e.g. a biocide, an antibiotic, or an antimicrobial agent, to thereby kill, disperse, treat, reduce prevent, or inhibit bacterial biofilms. An antibiotic can be co-administered with the polyamine compound either sequentially or simultaneously.

The antibiotic can be any compound known to one of ordinary skill in the art that can inhibit the growth of, or kill, bacteria. Useful, non-limiting examples of antibiotics include lincosamides (clindomycin); chloramphenicols; tetracyclines (such as tetracycline, chlortetracycline, demeclocycline, methacycline, doxycycline, minocycline); aminoglycosides (such as gentamicin, tobramycin, netilmicin, smikacin, kanamycin, streptomycin, neomycin); beta-lactams (such as penicillins, cephalosporins, imipenem, aztreonam); glycopeptide antibiotics (such as vancomycin); polypeptide antibiotics (such as bacitracin); macrolides (erythromycins), amphotericins; sulfonamides (such as sulfanilamide, sulfamethoxazole, sulfacetamide, sulfadiazine, sulfisoxazole, sulfacytine, sulfadoxine, mafenide, p-aminobenzoic acid, trimethoprim-sulfamethoxazole); methenamin; nitrofurantoin; phenazopyridine; trimethoprim; rifampicins; metronidazoles; cefazolins; lincomycin; spectinomycin; mupirocins; quinolones (such as nalidixic acid, cinoxacin, norfloxacin, ciprofloxacin, perfloxacin, ofloxacin, enoxacin, fleroxacin, levofloxacin); novobiocins; polymixins; gramicidins; and antipseudomonals (such as carbenicillin, carbenicillin indanyl, ticarcillin, azlocillin, mezlocillin, piperacillin) or any salts or variants thereof. Such antibiotics are commercially available, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

Additional known biocides include biguanide, chlorhexidine, triclosan, chlorine dioxide, and the like.

Useful examples of antimicrobial agents include, but are not limited to, Pyrithiones, especially the zinc complex (ZPT); Octopirox®; dimethyldimethylol hydantoin (Glydant®); methylchloroisothiazolinone/methylisothiazolinone (Kathon CG®); sodium sulfite; sodium bisulfite; imidazolidinyl urea (Germall 115®), diazolidinyl urea (Germaill II®); benzyl alcohol; 2-bromo-2-nitropropane-1,3-diol (Bronopol®); formalin (formaldehyde); iodopropenyl butylcarbamate (Polyphase PI 00®); chloroacetamide; methanamine; methyldibromonitrile glutaronitrile (1,2-dibromo-2,4-dicyanobutane or Tektamer®); glutaraldehyde; 5-bromo-5-nitro-1,3-dioxane (Bronidox®); phenethyl alcohol; o-phenylphenol/sodium o-phenylphenol; sodium hydroxymethylglycinate (Suttocide A®); polymethoxy bicyclic oxazolidine (Nuosept C®); dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether (Triclosan®. or TCS); 2,2'-dihydroxy-5,5'-dibromo-diphenyl ether; phenolic compounds; phenol; 2-methylphenol; 3-methylphenol; 4-methylphenol; 4-ethylphenol; 2,4-dimethylphenol; 2,5-dimethylphenol; 3,4-dimethylphenol; 2,6-dimethylphenol; 4-n-propylphenol; 4-n-butylphenol; 4-n-amylphenol; 4-tert-amylphenol; 4-n-hexylphenol; 4-n-heptylphenol; mono- and poly-alkyl and aromatic halophenols; p-chlorophenol; methyl p-chlorophenol; ethyl p-chlorophenol; n-propyl p-chlorophenol; n-butyl p-chlorophenol; n-amyl p-chlorophenol; sec-amyl p-chlorophenol; cyclohexyl p-chlorophenol; n-heptyl p-chlorophenol; n-octyl p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl-p-chlorophenol; o-phenylethyl-p-chlorophenol; o-phenylethyl-m-methyl p-chlorophenol; 3-methyl p-chlorophenol; 3,5-dimethyl p-chlorophenol; 6-ethyl-3-methyl p-chlorophenol; 6-n-propyl-3-methyl-p-chlorophenol; 6-isopropyl-3-methyl-p-chlorophenol; 2-ethyl-3,5-dimethyl p-chlorophenol; 6-sec-butyl-3-methyl p-chlorophenol; 2-isopropyl-3, 5-dimethyl p-chlorophenol; 6-diethylmethyl-3-methyl p-chlorophenol; 6-isopropyl-2-ethyl-3-methyl p-chlorophenol; 2-sec-amyl-3, 5-dimethyl p-chlorophenol; 2-diethylmethyl-3, 5-dimethyl p-chlorophenol; 6-sec-octyl-3-methyl p-chlorophenol; p-chloro-m-cresol: p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl-o-bromophenol; 2-phenylphenol; 4-chloro-2-methylphenol; 4-chloro-3-methyl phenol; 4-chloro-3,5-dimethyl phenol; 2,4-dichloro-3,5-dimethylphenol; 3,4,5,6-tetrabromo-2-methyl-phenol; 5-methyl-2-pentylphenol; 4-isopropyl-3-methylphenol; p-chloro-m-xylenol (PCMX); chlorothymol; phenoxyethanol; phenoxyisopropanol; 5-chloro-2-hydroxydiphenyl-methane; resorcinol and its derivatives; resorcinol; methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro 2,4-dihydroxydiphenyl methane; 4'-chloro 2,4-dihydroxydiphenyl methane; 5-bromo 2,4-dihydroxydiphenyl methane;

4'-bromo 2,4-dihydroxydiphenyl methane; bisphenolic compounds; 2,2'-methylene bis-(4-chlorophenol); 2,2'-methylene bis-(3,4,6-trichlorophenol); 2,2'-methylene bis(4-chloro-6-bromophenol); bis(2-hydroxy-3,5-dichlorophenyl) sulfide; bis(2-hydroxy-5-chlorobenzyl)sulfide; benzoic esters (parabens); methylparaben; propylparaben; butylparaben; ethylparaben; isopropylparaben; isobutylparaben; benzylparaben; sodium methylparaben; sodium propylparaben; halogenated carbanilides; 3,4,4'-trichlorocarbanilides (e.g., Triclocarban® or TCC); 3-trifluoromethyl-4,4'-dichlorocarbanilide; 3,3',4-trichlorocarbanilide; chlorohexidine and its digluconate; diacetate and dihydrochloride; undecenoic acid; thiabendazole, hexetidine; and poly(hexamethylenebiguanide) hydrochloride (Cosmocil®).

In some embodiments of any methods described herein, the method further comprises administering a biocide. In some embodiments, the biocide is an antibiotic.

In instances where a polyamine compound, or combination of a polyamine compound with another compound, is to be administered to a subject, the compound or composition herein can be incorporated into pharmaceutical compositions. The polyamine compound, or combination of a polyamine compound with another compound, can be incorporated into pharmaceutical compositions as pharmaceutically acceptable salts or derivatives. Some pharmaceutically acceptable derivatives of the polyamine compounds of the present invention may include a chemical group, which increases aqueous solubility. As used herein, a "pharmaceutically acceptable carrier" means a carrier that can be administered to a subject together with a polyamine compound, or combination of a polyamine compound with another compound, described herein, which does not destroy the pharmacological activity thereof. Pharmaceutically acceptable carriers include, for example, solvents, binders, dispersion media, coatings, preservatives, colorants, isotonic and absorption delaying agents, and the like, compatible with pharmaceutical administration. Supplementary active compounds can also be incorporated into the compositions.

Non-limiting examples of pharmaceutically acceptable carriers that can be used include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid (PLGA), polycaprolactone, polyvalerolactone, poly (anhydrides), copolymers of polycaprolactone with polyethylene glycol, copolymers of polylactic acid with polyethylene glycol, polyethylene glycol; and combinations and blends thereof.

Other carriers include, e.g., an aqueous gelatin, an aqueous protein, a polymeric carrier, a cross-linking agent, or a combination thereof. In other instances, the carrier is a matrix. In yet another instances, the carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-human amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTPA, a chelating agent for a divalent metal ion, a chelating agent for a trivalent metal ion, glutathione, pharmaceutically acceptable nonspecific serum albumin, or combinations thereof.

In other embodiments, the compositions can also comprise a pharmaceutically acceptable carrier. In still other embodiments the effective amount is an amount effective to treat or prevent a biofilm-related disorder. In some embodiments, an effective amount comprises and amount effective to treat or prevent a biofilm on a surface.

In some embodiments, the compositions discussed herein further comprises an agent suitable for application to the surface. In other embodiments, the composition is formulated as a wash solution, a dressing, a wound gel, or a synthetic tissue. In further embodiments, the composition is formulated as tablets, pills, troches, capsules, aerosol spray, solutions, suspensions, gels, pastes, creams, or foams. In some embodiments, the composition is formulated for parenteral (e.g., intravenous), intradermal, subcutaneous, oral (e.g., inhalation), transdermal (topical), transmucosal, vaginal, or rectal administration.

Another aspect of this disclosure is directed to biofilm resistant medical devices, comprising a surface likely to contact a biological fluid and a polyamine compound. In some embodiments, the medical device further comprises a polyamine compound, or combinations of a polyamine compound and at least one other composition, that is coated on or impregnated into said surface.

In some embodiments, the polyamine compound or combination of a polyamine compound and at least one other composition is formulated as a slow-release formulation.

In some embodiments, the polyamine compound or combination of a polyamine compound and at least one other composition are directed for use in medical applications, for example, active release or passive antimicrobial coatings for medical devices, lavage solutions for open wounds, oral mouthwashes, toothpaste additives, hand sanitizers, systemic prophylactic antibiotics, lock solutions for catheters, eye drop solutions for irrigation and contact lens cleaners, prophylactic dental inserts, high level disinfectants, gastrointestinal (GI) tract oral medications for the treatment of infections such as those caused by *Shigella, Cryptosporidium, Vibrio cholerae*, or *Clostridium difficile*, cancer treatment including multiple myeloma, osteosarcoma, lymphoma or other forms of cancer, topical ointments to treat dermatological complications including infection, canker sores, psoriasis, herpes, chronic wounds, diaper rash, onychomycosis (athletes foot), tinea unguium (toenail fungus), ulcers, or acne, etc.

In some embodiments, the base is selected from a liquid, gel, paste, or powder. In further embodiments, the composition is selected from shampoos, bath additives, hair care preparations, soaps, lotions, creams, deodorants, skin-care preparations, cosmetic personal care preparations, intimate hygiene preparations, foot care preparations, light protective preparations, skin tanning preparations, insect repellants, antiperspirants, shaving preparations, hair removal preparations, fragrance preparations, dental care, denture care and mouth care preparations and combinations thereof.

A pharmaceutical composition containing a polyamine compound, or combination of a polyamine compound with another compound, can be formulated to be compatible with its intended route of administration as known by those of ordinary skill in the art. Nonlimiting examples of routes of administration include parenteral, e.g., intravenous, intradermal, subcutaneous, oral {e.g., inhalation), transdermal (topical), transmucosal, vaginal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition can be sterile and can be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be desirable to include isotonic agents, for example, sugars, polyalcohols such as mannitol, sorbitol, or sodium chloride in the composition. Prolonged absorption of the injectable compositions can be accomplished by including in the composition an agent that delays absorption, for example, aluminum monostearate and gelatin (see, e.g., Remington: The Science and Practice of Pharmacy, 21st edition, Lippincott Williams & Wilkins, Gennaro, ed. (2006)).

Sterile injectable solutions can be prepared by incorporating a polyamine compound, or combination of a polyamine compound with another compound, in the required amount in an appropriate solvent with one or a combination of ingredients enumerated above, as required, followed by filtered sterilization. Generally, dispersions are prepared by incorporating an active compound into a sterile vehicle that contains a basic dispersion medium and the required other ingredients from those enumerated above. In the case of sterile powders for the preparation of sterile injectable solutions, the methods of preparation include, without limitation, vacuum drying and freeze-drying which yields a powder of the active ingredient plus any additional desired ingredient from a previously sterile-filtered solution thereof.

Oral compositions may include an inert diluent or an edible carrier or binders. For the purpose of oral therapeutic administration, a polyamine, or a combination of a polyamine compound, or combination of a polyamine compound with another compound, can be incorporated with excipients and used in the form of tablets, pills, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, polyamine compound, or combination of a polyamine compound with another compound, can be delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, but are not limited to, for example, for transmucosal administration, detergents, bile salts, and fusidic acid derivatives. Transmucosal administration can be accomplished through the use of nasal sprays or suppositories. For transdermal administration, the active compounds and compositions are formulated into pharmaceutically acceptable formulation embodiments, such as ointments, salves, gels, or creams as generally known in the art.

For treatment of acute or chronic wounds, polyamine compound, or combination of a polyamine compound with another compound, can be formulated as a dressing, a wash solution, gel, or a synthetic tissue, etc.

The pharmaceutical compositions containing a polyamine compound, or combination of a polyamine compound with another compound, can also be prepared in the form of suppositories (e.g., with conventional suppository bases such as cocoa butter and other glycerides) or retention enemas for rectal delivery.

Some pharmaceutical compositions containing a polyamine compound, or combination of a polyamine compound with another compound, can be prepared with a carrier that protects the polyamine compound, or combination of a polyamine compound with another compound, against rapid elimination from the body, such as a controlled release formulation, including implants and microencapsulated delivery systems as described, e.g., in Tan et al., Pharm. Res. 24:2297-2308 (2007).

Additionally, biodegradable, biocompatible polymers can be used, such as ethylene vinyl acetate, polyanhydrides, polyglycolic acid, collagen, polyorthoesters, and polylactic acid. Methods for preparation of such formulations are apparent to those skilled in the art. The materials can also be obtained commercially (e.g., from Alza Corp., Mountain View, Calif.). Liposomal suspensions (including liposomes targeted to particular cells with monoclonal antibodies to cell surface antigens) can also be used as pharmaceutically acceptable carriers. These can be prepared according to methods known to those skilled in the art, e.g., as described in U.S. Pat. No. 4,522,811.

Toxicity and therapeutic efficacy of such compounds and compositions can be determined by standard pharmaceutical procedures in cell cultures or experimental animals, e.g., for determining the $LD_{50}$ (the dose lethal to 50%> of the population) and the ED$_{50}$ (the dose therapeutically effective in 50% of the population). The dose ratio between toxic and therapeutic effects is the therapeutic index and it can be expressed as the ratio LD$_{50}$/ED$_{50}$. While compounds and compositions that exhibit toxic side effects can be used, care should be taken to design a delivery system that targets active components to the site of affected tissue in order to minimize potential damage to normal cells and, thereby, reduce side effects.

The data obtained from the cell culture assays and animal studies can be used in formulating a range of dosage for use in humans. The dosage of such compounds and compositions lies generally within a range of circulating concentrations that include the ED$_{50}$ with little or no toxicity. The dosage can vary within this range depending upon the dosage form employed and the route of administration utilized. For any compounds or compositions used in the methods described herein, the therapeutically effective dose can be estimated initially from cell culture assays. A dose can be formulated in animal models to achieve a circulating plasma concentration range that includes the IC$_{50}$ (i.e., the concentration of the test compound or composition that achieves a half-maximal inhibition of symptoms) as determined in cell culture. Such information can be used to more accurately determine useful doses in humans. Levels in plasma can be measured, for example, by high performance liquid chromatography. Information for preparing and testing such compositions are known in the art. See, e.g., Remington: The Science and Practice of Pharmacy, 21st ed., Lippincott Williams & Wilkins, Gennaro, ed. (2006).

A physician will appreciate that certain factors may influence the dosage required to effectively treat a subject, including but not limited to the severity of the disease or disorder, previous treatments, the general health or age of the subject, and other diseases present. Moreover, treatment of a subject with a therapeutically effective amount of a polyamine compound, or combination of a polyamine compound with another compound, can include a single treatment or a series of treatments.

The compounds or pharmaceutical compositions can be included in a container, pack, or dispenser together with instructions for administration. A person of ordinary skill in the art will appreciate that the compounds or pharmaceutical compositions described herein can be formulated as single-dose vials.

Polyamine compounds, or combination of a polyamine compound with another compound, may be suitable as antibiofilm active substances in personal care preparations, for example shampoos, bath additives, hair care preparations, liquid and solid soaps (based on synthetic surfactants and salts of saturated or unsaturated fatty acids), lotions and creams, deodorants, other aqueous or alcoholic solutions, e.g. cleansing solutions for the skin, moist cleaning cloths, oils or powders.

Any suitable amount of polyamine can be used in the compositions and methods of the invention. In general, the polyamines are used in concentrations ranging from about 1 ppm to about 100,000 ppm, or higher. The concentration of a polyamine used in a composition or method of the invention can be, for example, from about 1 to about 100,000 ppm, or from about 10 to about 10,000 ppm, or from about 100 to about 1,000 ppm, or from about 1 to about 100 ppm, or from about 1,000 to about 10,000 ppm, or from about 10,000 to about 100,000 ppm. The concentration of a polyamine can be about 1; 2; 3; 4; 5; 6; 7; 8; 9; 10; 15; 20; 25; 30; 35; 40; 45; 50; 55; 60; 65; 70; 75; 80; 85; 90; 95; 100; 125; 150; 175; 200; 225; 250; 275; 300; 325; 350; 375; 400; 425; 450; 475; 500; 525; 550; 575; 600; 625; 650; 675; 700; 725; 750; 775; 800; 825; 850; 875; 900; 925; 950; 975; 1000; 1500; 2000; 2500; 3000; 3500; 4000; 4500; 5000; 5500; 6000; 6500; 7000; 7500; 8000; 8500; 9000; 9500; 10,000; 12,500; 15,000; 17,500; 20,000; 22,500; 25,000; 27,500; 30,000; 32,500; 35,000; 37,500; 40,000; 42,500; 45,000; 47,500; 50,000; 52,500; 55,000; 57,500; 60,000; 62,500; 65,000; 67,500; 70,000; 72,500; 75,000; 77,500; 80,000; 82,500; 85,000; 87,500; 90,000; 92,500; 95,000; 97,500; or about 100,000 ppm. Other concentrations of polyamines can be useful in the compositions and methods of the invention, depending in part on factors including the specific polyamine used, the presence of other active agents if any, or the species of microorganisms that are targeted.

There is thus disclosed compounds, compositions, or methods comprising novel polyamine compounds, or combinations of polyamine compounds with other compounds, that have antimicrobial activity and dispersing activity against a variety of bacterial strains capable of forming biofilms, and methods of using the same.

EXAMPLES

The following examples serve to explain embodiments of the present disclosure in more detail. These examples should not be construed as being exhaustive or exclusive as to the scope of this disclosure.

Example 1: General Procedure for Preparation of Polyamines

To a stirring solution of a dicarbaldehyde (e.g., 5'-(tert-butyl)-[1,1':3',1''-terphenyl]-4,4''-dicarbaldehyde: 2.12 g, 6.22 mmol, 1 equiv.) in MeOH (100 mL) and DCE (25 mL) at 0° C. was added a diamine (e.g., N1-(3-aminopropyl)-N3-(2-ethylbutyl)propane-1,3-diamine: 3.61 g, 16.79 mmol, 2.7 equiv.) portion wise over the span of 20 min. The solution was then left to stir for 16 h. NaBH$_4$ (0.95 g, 24.88, 1 equiv.) was subsequently added portion wise over the span of 20 min and the reaction was allowed to stir for an additional hour. The solvent was then evaporated, and the crude solid was partitioned between EtOAc (500 mL) and 10% NaOH (250 mL). The NaOH phase was then washed with EtOAc (500 mL), and the combined organics were dried over Na$_2$SO$_4$. If desired, column chromatography can be performed using gradient conditions starting at (300:16:1 CH$_2$Cl$_2$:MeOH:NH$_4$OH). The free base was acidified with HCl in MeOH (100 mL) and then placed at 0° C. for 1 h to precipitate. The corresponding precipitate was filtered and dried to afford the crude HCl salt as a white solid (25-52%). If the subsequent HCl salt remains impure, recrystallization with H$_2$O (solvent) and iPrOH (anti-solvent) helps ensure purity.

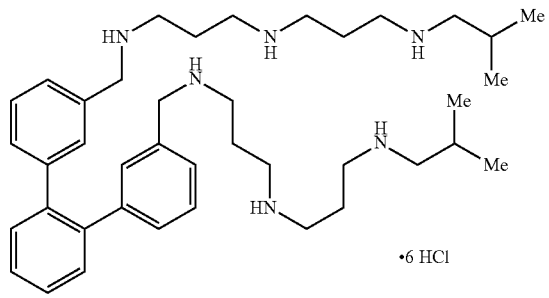 [SMILES: CC(C)CNCCCNCCCNCc1cccc(-c2ccccc2-c2cccc(CNCCCNCCCNCC(C)C)c2)c1]

CZ-01-152: N$^1$,N$^{1'}$-([1,1':2',1''-terphenyl]-3,3''-diyl-bis(metylbis(methylene))bis(N$^3$-(3-(isobutylamino)propyl)propane-1,3-diamine), hydrochloride salt $^1$H NMR (500 MHz, D$_2$O) δ ppm 7.64-7.58 (m, 4H), 7.43-7.38 (m, 6H), 7.30-7.28 (m, 2H), 4.23 (s, 4H), 3.24-3.13 (m, 16H), 2.97 (d, J=7.5 Hz, 4H), 2.22-2.14 (m, 8H), 2.06 (sept, J=6.5 Hz, 2H), 1.04 (d, J=7.0 Hz, 12H). $^{13}$C NMR (125 MHz, D$_2$O) δ ppm 142.0, 139.4, 131.2, 131.1, 130.5, 130.4, 128.9, 128.4, 128.1, 54.9, 51.0, 48.9, 44.7, 44.6, 43.8, 25.6, 22.6, 22.5, 19.0. LRMS Calculated for C$_{40}$H$_{64}$N$_6$ m/z 629.5 [M+H]$^+$, Obsd. 315.2 [M+H]$^+$/2.

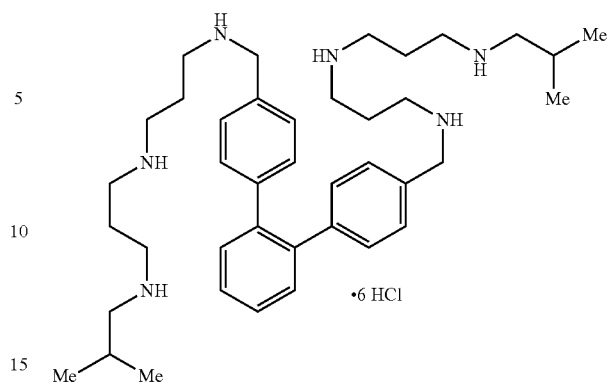

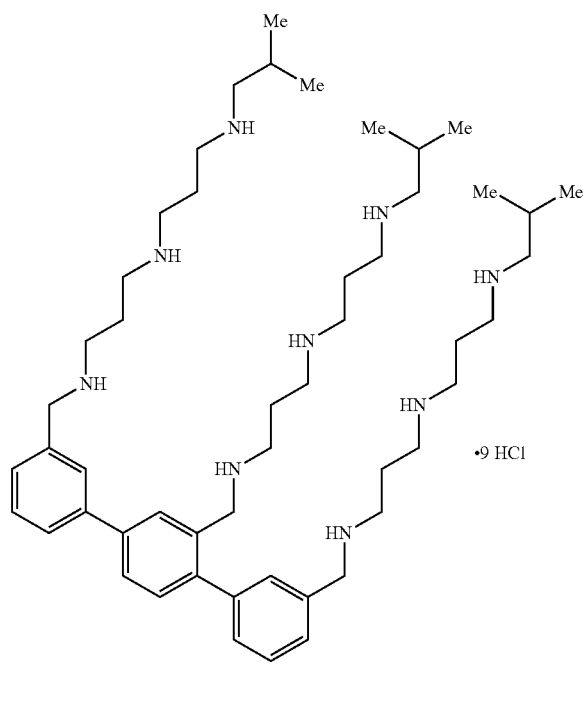 [SMILES: CC(C)CNCCCNCCCNCc1cccc(-c2ccc(-c3cccc(CNCCCNCCCNCC(C)C)c3)c(CNCCCNCCCNCC(C)C)c2)c1]

CZ-01-153: N$^1$,N$^{1'}$,N$^{1'''}$-([1,1':4',1''-terphenyl]-2',3,3''-triyltris(methylene))tris(N$^3$-(3-(isobutylamino)propyl)propane-1,3-diamine), hydrochloride salt $^1$H NMR (500 MHz, D$_2$O) δ ppm 7.94-7.90 (m, 3H), 7.81-7.80 (m, 2H), 7.75-7.60 (m, 6H), 4.44-4.43 (m, 6H), 3.36-3.06 (m, 24H), 2.98-2.97 (m, 6H), 2.29-2.03 (m, 15H), 1.05 (d, J=6.5 Hz, 18H). $^{13}$C NMR (125 MHz, D$_2$O) δ ppm 142.5, 140.9, 140.2, 140.1, 131.3, 131.2, 130.7, 130.3, 130.0, 129.4, 128.5, 128.4, 127.7, 127.1, 54.9, 51.2, 48.0, 44.8, 44.6, 44.7, 44.5, 44.3, 44.2, 44.1, 25.6, 22.6, 22.5, 19.0. LRMS Calculated for C$_{51}$H$_{89}$N$_9$ m/z 828.7 [M+H]$^+$, Obsd. 414.8 [M+H]$^+$/2.

CZ-01-154: N$^1$,N$^{1'}$-([1,1':2',1''-terphenyl]-4,4''-diyl-bis(methylene))bis(N$^3$-(3-(isobutylamino)propyl)propane-1,3-diamine), hydrochloride salt $^1$H NMR (500 MHz, D$_2$O) δ ppm 7.63-7.58 (m, 4H), 7.41 (d, J=8.0 Hz, 4H), 7.33 (d, J=8.5 Hz, 4H), 4.29 (s, 4H), 3.26-3.18 (m, 16H), 2.97 (d, J=7.5 Hz, 4H), 2.23-2.13 (m, 8H), 2.08 (sept, J=7.0 Hz, 2H), 1.05 (d, J=7.0 Hz, 12H). $^{13}$C NMR (125 MHz, D$_2$O) δ ppm 142.5, 139.4, 130.6, 130.5, 129.5, 128.9, 128.3, 54.9, 50.9, 44.8, 44.6, 43.9, 25.6, 22.6, 22.5, 19.0. LRMS Calculated for C$_{40}$H$_{64}$N$_6$ m/z 629.6 [M+H]$^+$, Obsd. 629.5.

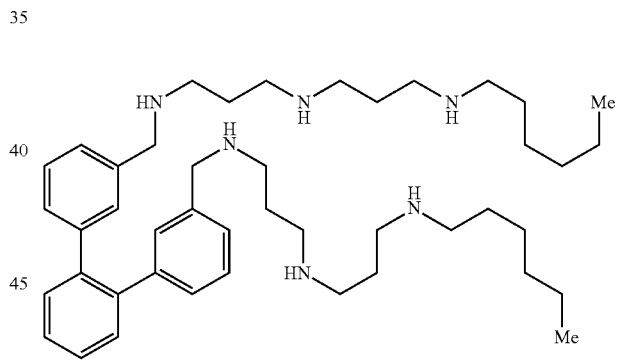

CZ-01-155: N$^1$,N$^{1'}$-([1,1':2',1''-terphenyl]-3,3''-diyl-bis(methylene))bis(N$^3$-(3-(hexylamino)propyl)propane-1,3-diamine), hydrochloride salt $^1$H NMR (500 MHz, D$_2$O) δ ppm 7.63-7.58 (m, 4H), 7.44-7.38 (m, 6H), 7.29 (d, J=7.0 Hz, 2H), 4.24 (s, 4H), 3.27-3.11 (m, 20H), 2.22-2.16 (m, 8H), 1.74 (pent, J=7.0 Hz, 4H), 1.45-1.36 (m, 12H), 0.93 (t, J=6.0 Hz, 6H). $^{13}$C NMR (125 MHz, D$_2$O) δ ppm 142.0, 139.4, 131.2, 131.1, 130.6, 130.4, 128.9, 128.4, 128.1, 51.0, 47.9, 44.7, 44.6, 44.2, 43.8, 30.4, 25.4, 25.3, 22.6, 22.6, 21.7, 13.2. LRMS Calculated for C$_{44}$H$_{72}$N$_6$ m/z 685.6 [M+H]$^+$, Obsd. 685.4.

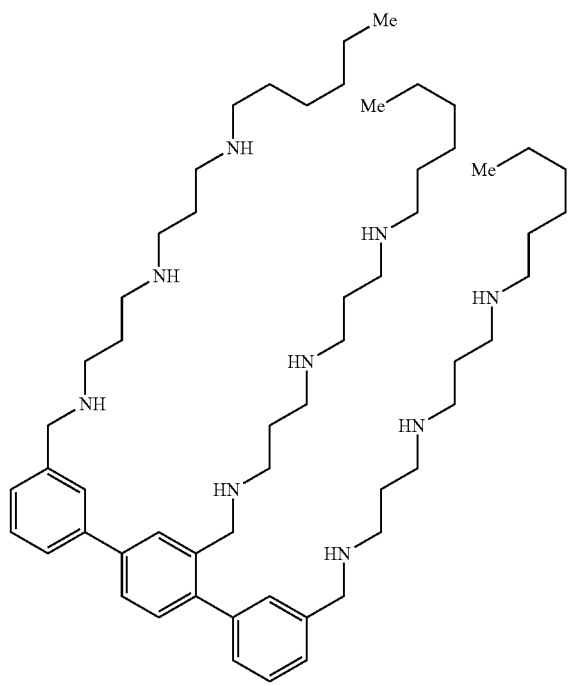 [SMILES: CCCCCCNCCCNCCCNCc1cccc(-c2ccc(-c3cccc(CNCCCNCCCNCCCCCC)c3)c(CNCCCNCCCNCCCCCC)c2)c1]

CZ-01-156: N¹,N¹',N¹''-([1,1':4',1''-terphenyl]-2',3,3'-triyltris(methylene))tris(N³-(3-(hexylamino)propyl)propane-1,3-diamine), hydrochloride salt $^1$H NMR (500 MHz, D$_2$O) δ ppm 7.92-7.88 (m, 3H), 7.81-7.78 (m, 2H), 7.74-7.66 (m, 3H), 7.63-7.60 (m, 3H), 4.45-4.43 (m, 6H), 3.37-3.06 (m, 30H), 2.31-2.06 (m, 12H), 1.76-1.71 (m, 6H), 1.44-1.34 (m, 18H), 0.92 (t, J=6.5 Hz, 9H). $^{13}$C NMR (125 MHz, D$_2$O) δ ppm 142.5, 140.9, 140.2, 140.0, 131.3, 131.2, 130.8, 130.7, 130.4, 130.0, 129.8, 129.4, 129.3, 128.5, 128.3, 127.6, 127.1, 51.2, 51.2, 48.0, 47.9, 44.7, 44.7, 44.5, 44.3, 44.2, 44.2, 44.1, 30.4, 25.4, 25.3, 22.7, 22.6, 22.5, 21.7, 13.2. LRMS Calculated for C$_{57}$H$_{101}$N$_9$ m/z 912.8 [M+H]$^+$, Obsd. 456.8 [M+H]$^+$/2.

CZ-01-157: N¹,N¹'-([1,1':3',1''-terphenyl]-4,4''-diyl-bis(methylene))bis(N³-(3-(isobutylamino)propyl)propane-1,3-diamine), hydrochloride salt $^1$H NMR (500 MHz, D$_2$O) δ ppm 7.97 (s, 1H), 7.86 (d, J=8.0 Hz, 4H), 7.77 (d, J=7.5 Hz, 2H), 7.68-7.64 (m, 5H), 4.38 (s, 4H), 3.31-3.17 (m, 16H), 2.96 (d, J=7.5 Hz, 4H), 2.25-2.15 (m, 8H), 2.06 (sept, J=7.0 Hz, 2H), 1.03 (d, J=6.5 Hz, 12H). $^{13}$C NMR (125 MHz, D$_2$O) δ ppm 141.5, 140.4, 130.5, 129.9, 129.8, 127.7, 126.6, 125.4, 54.9, 50.9, 44.8, 44.6, 43.9, 25.6, 22.6, 22.5, 19.0. LRMS Calculated for C$_{40}$H$_{64}$N$_6$ m/z 629.5 [M+H]$^+$, Obsd. 629.4.

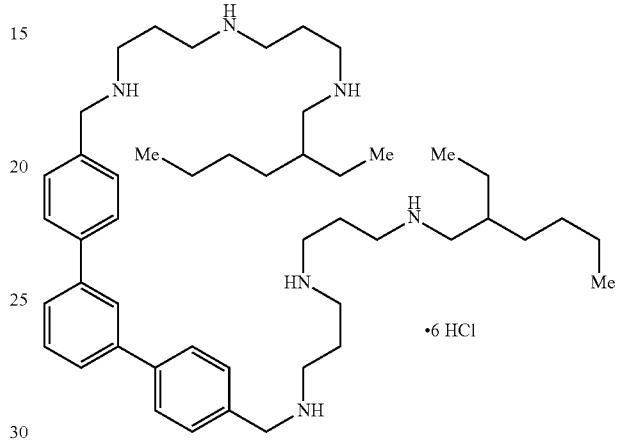

CZ-01-161: N¹,N¹'-([1,1':3',1''-terphenyl]-4,4''-diyl-bis(methylene))bis(N³-(3-((2-ethylhexyl)amino)propyl)propane-1,3-diamine), hydrochloride salt $^1$H NMR (500 MHz, D$_2$O) δ ppm 8.06 (t, J=1.5 Hz, 1H), 7.91 (d, J=8.0 Hz, 4H), 7.84-7.82 (m, 2H), 7.72 (t, J=7.5 Hz, 1H), 7.68 (d, J=8.0 Hz, 4H), 4.41 (s, 4H), 3.30 (t, J=8.0 Hz, 4H), 3.26-3.17 (m, 12H), 3.04 (d, J=7.0 Hz, 4H), 2.25-2.18 (m, 8H), 1.76 (sept, J=6.0 Hz, 2H), 1.48-1.33 (m, 16H), 0.94-0.91 (m, 12H). $^{13}$C NMR (125 MHz, D$_2$O) δ ppm 141.4, 140.3, 130.5, 129.8, 129.7, 127.7, 126.6, 125.4, 51.3, 50.8, 44.8, 44.5, 43.8, 36.1, 29.4, 27.5, 22.8, 22.5, 22.4, 22.1, 13.2, 9.3. LRMS Calculated for C$_{48}$H$_{80}$N$_6$ m/z 741.6 [M+H]$^+$, Obsd. 371.3. [M+H]$^+$/2.

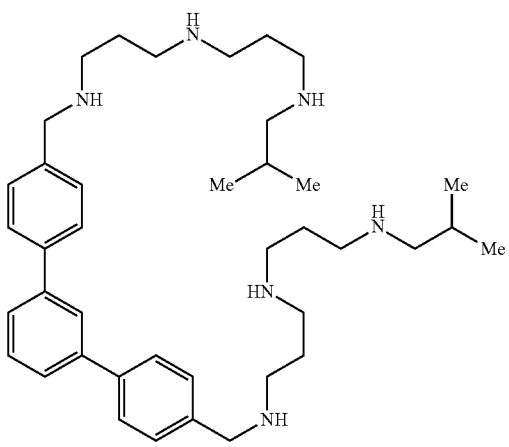 [SMILES: CC(C)CNCCCNCCCNCc1ccc(-c2cccc(-c3ccc(CNCCCNCCCNCC(C)C)cc3)c2)cc1]

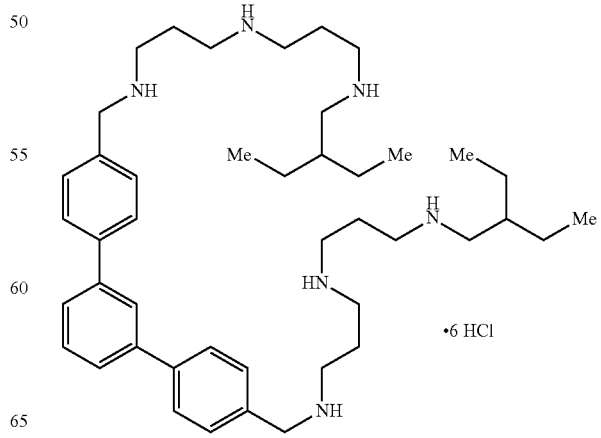

CZ-01-164: N¹,N¹'-([1,1':3',1''-terphenyl]-4,4''-diyl-bis(methylene))bis(N³-(3-((2-ethylbutyl)amino)propyl)propane-1,3-diamine), hydrochloride salt $^1$H NMR (500 MHz, D$_2$O) δ ppm 7.97 (t, J=1.5 Hz, 1H), 7.83 (d, J=8.0 Hz, 4H), 7.75-7.73 (m, 2H), 7.64 (t, J=7.0 Hz, 1H), 7.60 (d, J=8.0 Hz, 4H), 4.33 (s, 4H), 3.23 (t, J=8.0 Hz, 4H), 3.19-3.10 (m, 12H), 2.97 (d, J=7.0 Hz, 4H), 2.19-2.08 (m, 8H), 1.64 (sept, J=6.5 Hz, 2H), 1.37 (p, J=7.0 Hz, 8H), 0.85 (t, J=7.5 Hz, 12H). $^{13}$C NMR (125 MHz, D$_2$O) δ ppm 141.5, 140.4, 130.4, 129.8, 129.7, 127.7, 126.6, 125.5, 50.9, 50.8, 44.8, 44.5, 43.8, 37.6, 22.6, 22.3, 22.4, 9.3. LRMS Calculated for C$_{44}$H$_{72}$N$_6$ m/z 685.6 [M+H]$^+$, Obsd. 343.1 [M+H]$^+$/2.

CZ-01-174: N¹,N¹'-((pyrimidine-2,4-diylbis(4,1-phenylene))bis(methylene))bis(N³-(3-(isopentylamino)propyl)propane-1,3-diamine), hydrochloride salt $^1$H NMR (500 MHz, D$_2$O) δ ppm 8.91 (d, J=5.5 Hz, 1H), 8.36 (d, J=8.0 Hz, 2H), 8.27 (d, J=7.5 Hz, 2H), 7.96 (d, J=5.5 Hz, 1H), 7.72 (d, J=7.0 Hz, 4H), 4.43 (s, 2H), 4.42 (s, 2H), 3.35-3.20 (m, 16H), 3.14 (t, J=8.0 Hz, 4H), 2.28-2.16 (m, 8H), 1.72 (sept, J=6.5 Hz, 2H), 1.65-1.60 (m, 4H), 0.97 (d, J=6.5 Hz, 12H). $^{13}$C NMR (125 MHz, D$_2$O) δ ppm 164.5, 163.4, 157.7, 137.6, 136.9, 133.8, 133.4, 130.5, 130.4, 129.0, 128.4, 116.4, 50.8, 50.8, 46.4, 44.7, 44.6, 44.2, 44.2, 44.1, 34.1, 25.2, 22.6, 21.3. LRMS Calculated for C$_{40}$H$_{66}$N$_8$ m/z 659.5 [M+H]$^+$, Obsd. 659.4.

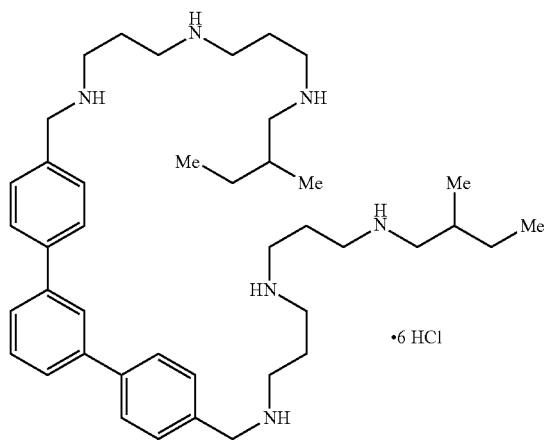 [SMILES: CCC(C)CNCCCNCCCNCc1ccc(-c2cccc(-c3ccc(CNCCCNCCCNCC(C)CC)cc3)c2)cc1]

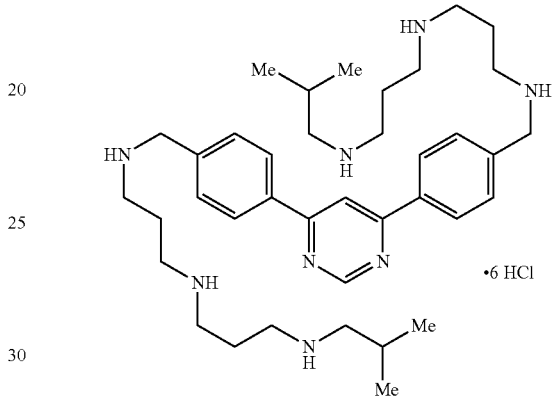

CZ-01-166: N¹,N¹'-([1,1':3',1''-terphenyl]-4,4''-diyl-bis(methylene))bis(N³-(3-((2-methylbutyl)amino)propyl)propane-1,3-diamine), hydrochloride salt $^1$H NMR (500 MHz, D$_2$O) δ ppm 7.86 (t, J=1.5 Hz, 1H), 7.78 (d, J=8.5 Hz, 4H), 7.71-7.67 (m, 2H), 7.63-7.58 (m, 6H), 4.36 (s, 4H), 3.31-3.18 (m, 16H), 3.07 (dd, J=6.0, 12 Hz, 2H), 2.93 (dd, J=8.5, 12.5 Hz, 2H), 2.26-2.17 (m, 8H), 1.89-1.82 (m, 2H), 1.52-1.44 (m, 2H), 1.34-1.25 (m, 2H), 1.03 (d, J=6.5 Hz, 6H), 0.95 (t, J=8.0 Hz, 6H). $^{13}$C NMR (125 MHz, D$_2$O) δ ppm 141.4, 140.3, 130.5, 129.8, 129.7, 127.7, 126.6, 125.4, 53.5, 50.9, 44.8, 44.6, 43.9, 31.8, 26.2, 22.6, 22.5, 16.0, 10.1. IR (neat): 3342 (bs), 2963, 2766, 1457 (all s) cm$^{-1}$. mp decomposition (232-234° C.). LRMS Calculated for C$_{42}$H$_{68}$N$_6$ m/z 657.6 [M+H]$^+$, Obsd. 657.4.

CZ-01-176: N¹,N¹'-((pyrimidine-4,6-diylbis(4,1-phenylene))bis(methylene))bis(N³-(3-(isobutylamino)propyl)propane-1,3-diamine), hydrochloride salt $^1$H NMR (500 MHz, D$_2$O) δ ppm 9.22 (s, 1H), 8.37 (s, 1H), 8.16 (d, J=8.5 Hz, 4H), 7.71 (d, J=8.0 Hz, 4H), 4.39 (s, 4H), 3.28 (t, J=8.5 Hz, 4H), 3.23-3.15 (m, 12H), 2.93 (d, J=7.0 Hz, 4H), 2.23-2.12 (m, 8H), 2.02 (sept, J=7.0 Hz, 2H), 1.00 (d, J=6.5 Hz, 12H). $^{13}$C NMR (125 MHz, D$_2$O) δ ppm 164.6, 157.6, 136.9, 133.7, 130.6, 128.4, 115.6, 54.8, 50.7, 44.7, 44.6, 44.6, 44.1, 25.5, 22.6, 22.5, 19.0. LRMS Calculated for C$_{38}$H$_{62}$N$_8$ m/z 631.5 [M+H]$^+$, Obsd. 631.9.

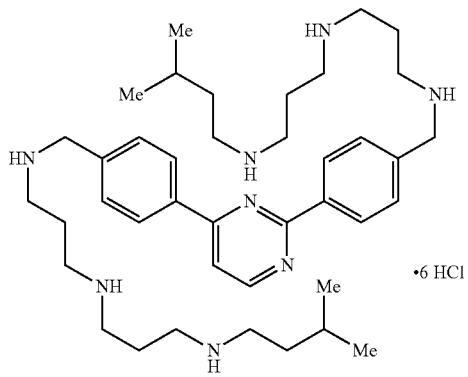 [SMILES: CC(C)CCNCCCNCCCNCc1ccc(-c2ccnc(-c3ccc(CNCCCNCCCNCCC(C)C)cc3)n2)cc1]

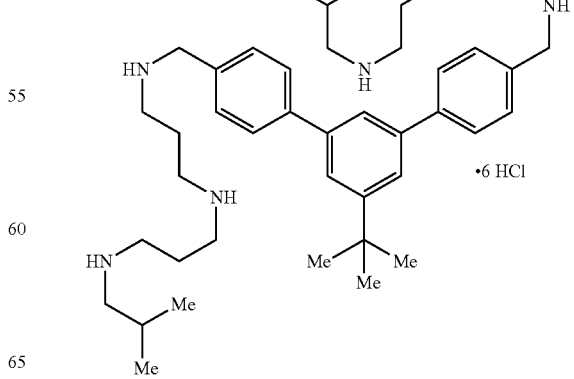

CZ-01-177: N¹,N¹'-((5'-(tert-butyl)-[1,1':3',1''-terphenyl]-4,4''-diyl)bis(methylene))bis(N³-(3-(isobutylamino)propyl)propane-1,3-diamine), hydrochloride salt ¹H NMR (500 MHz, D$_2$O) δ ppm 7.78 (d, J=7.5 Hz, 4H), 7.74 (d, 2H), 7.71 (s, 1H), 7.60 (d, J=8.0 Hz, 4H), 4.34 (s, 4H), 3.28-3.14 (m, 16H), 2.93 (d, J=7.0 Hz, 4H), 2.22-2.12 (m, 8H), 2.02 (sept, J=7.0 Hz, 2H), 1.39 (s, 9H), 1.00 (d, J=6.5 Hz, 12H). ¹³C NMR (125 MHz, D$_2$O) δ ppm 153.4, 141.8, 140.5, 130.4, 129.7, 127.8, 123.8, 122.9, 54.9, 50.9, 44.7, 44.6, 43.9, 34.5, 30.5, 25.5, 22.6, 22.5, 19.0. LRMS Calculated for C$_{44}$H$_{72}$N$_6$ m/z 685.6 [M+H]$^+$, Obsd. 343.3 [M+H]$^+$/2.

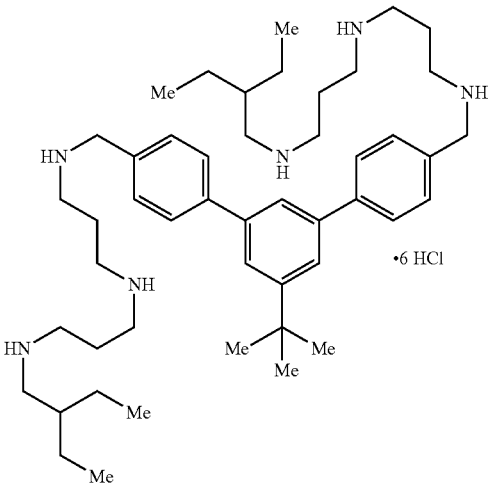

CZ-01-178: N¹,N¹'-((5'-(tert-butyl)-[1,1':3',1''-terphenyl]-4,4''-diyl)bis(methylene))bis(N³-(3-((2-methylbutyl)amino)propyl)propane-1,3-diamine), hydrochloride salt

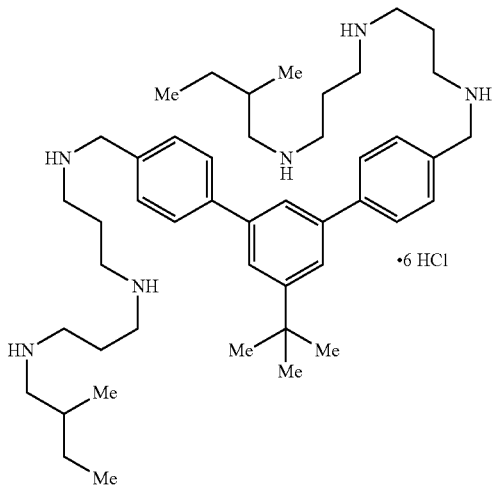 [SMILES: CCC(C)CNCCCNCCCNCc1ccc(-c2cc(-c3ccc(CNCCCNCCCNCC(C)CC)cc3)cc(C(C)(C)C)c2)cc1]

¹H NMR (500 MHz, D$_2$O) δ ppm 7.65 (d, J=7.5 Hz, 4H), 7.59 (s, 2H), 7.57-7.52 (m, 5H), 4.27 (s, 4H), 3.22-3.09 (m, 16H), 2.98 (dd, J=6.0, 12.0 Hz, 2H), 2.84 (dd, J=8.5, 12.0 Hz, 2H), 2.18-2.09 (m, 8H), 1.77 (hex, J=6.0 Hz, 2H), 1.39 (sept, J=7.0 Hz, 2H), 1.27 (s, 9H), 1.23-1.19 (m, 2H), 0.94 (d, J=6.0 Hz, 6H), 0.86 (t, J=7.5 Hz, 6H). ¹³C NMR (125 MHz, D$_2$O) δ ppm 153.2, 141.7, 140.2, 130.4, 129.6, 127.7, 123.6, 122.8, 53.4, 50.9, 48.8, 44.8, 44.6, 43.9, 34.4, 31.7, 30.5, 26.2, 22.6, 22.5, 15.9, 10.0. LRMS Calculated for C$_{46}$H$_{76}$N$_6$ m/z 713.6 [M+H]$^+$, Obsd. 356.6 [M+H]$^+$/2.

CZ-1-179: N¹,N¹'-((5'-(tert-butyl)-[1,1':3',1''-terphenyl]-4,4''-diyl)bis(methylene))bis(N³-(3-((2-ethylbutyl)amino)propyl)propane-1,3-diamine), hydrochloride salt ¹H NMR (500 MHz, D$_2$O) δ ppm 7.78-7.69 (m, 7H), 7.61 (bs, 4H), 4.38 (s, 4H), 3.26-3.20 (m, 16H), 3.01 (s, 4H), 2.17 (bs, 8H), 1.67 (bs, 2H), 1.38 (bs, 17H), 0.88 (s, 12H). ¹³C NMR (125 MHz, D$_2$O) δ ppm 153.4, 141.8, 140.4, 130.4, 129.7, 127.8, 123.8, 122.9, 50.9, 50.9, 44.9, 44.6, 43.9, 37.6, 34.4, 30.5, 22.6, 22.4, 22.4, 9.4. IR (neat): 3334 (bs), 2963, 2766, 1457 (all s) cm$^{-1}$. mp decomposition (180-184° C.). LRMS Calculated for C$_{48}$H$_{80}$N$_6$ m/z 741.6 [M+H]$^+$, Obsd. 370.7 [M+H]$^+$/2.

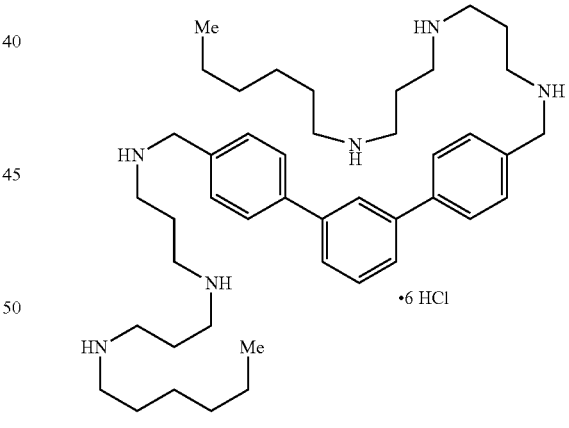

CZ-01-180: N1,N1'-([1,1':3',1''-terphenyl]-4,4''-dihybis(methylene))bis(N3-(3-(hexylamino)propyl) propane-1,3-diamine), hydrochloride salt ¹H NMR (500 MHz, D$_2$O) δ ppm 8.62-8.55 (m, 1H), 8.50 (d, J=8.5 Hz, 4H), 8.39 (d, J=7.5 Hz, 2H), 8.34-8.29 (m, 5H), 4.87 (s, 4H), 3.77 (t, J=7.5 Hz, 4H), 3.72-3.64 (m, 12H), 3.57 (t, J=7.5 Hz, 4H), 2.75-2.62 (m, 8H), 2.28-2.22 (m, 4H), 1.99-1.88 (m, 12H), 1.53 (t, J=6.5 Hz, 6H). LRMS Calculated for C$_{44}$H$_{72}$N$_6$ m/z 685.6 [M+H]$^+$, Obsd. 342.5 [M+H]$^+$/2.

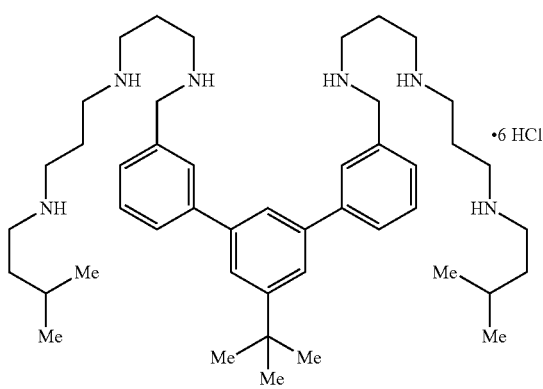 [SMILES: CC(C)CCNCCCNCCCNCc1cccc(-c2cc(-c3cccc(CNCCCNCCCNCCC(C)C)c3)cc(C(C)(C)C)c2)c1]

CZ-01-182: $N^1,N^{1''}$-((5'-(tert-butyl)-[1,1':3',1''-terphenyl]-3,3''-diyl)bis(methylene))bis($N^3$-(3-(isopentylamino)propyl)propane-1,3-diamine), hydrochloride salt $^1$H NMR (500 MHz, D$_2$O) δ ppm 7.86-7.82 (m, 6H), 7.63 (t, J=7.5 Hz, 2H), 7.53 (d, J=7.5 Hz, 2H), 4.37 (s, 4H), 3.26-3.05 (m, 20H), 2.20-2.07 (m, 8H), 1.65 (sept, J=6.5 Hz, 2H), 1.57-1.53 (m, 4H), 1.43 (s, 9H), 0.90 (d, J=7.0 Hz, 12H). $^{13}$C NMR (125 MHz, D$_2$O) δ ppm 153.6, 141.5, 140.8, 131.1, 129.8, 128.9, 128.6, 128.5, 123.8, 123.1, 51.2, 46.3, 44.5, 44.1, 43.9, 34.5, 34.1, 30.5, 25.1, 22.6, 22.6, 21.2. IR (neat): 3367 (bs), 2957, 1457 (all s) cm$^{-1}$. mp decomposition (218-220° C.). LRMS Calculated for C$_{46}$H$_{76}$N$_6$ m/z 713.6 [M+H]$^+$, Obsd. 713.5 [M+H]$^+$.

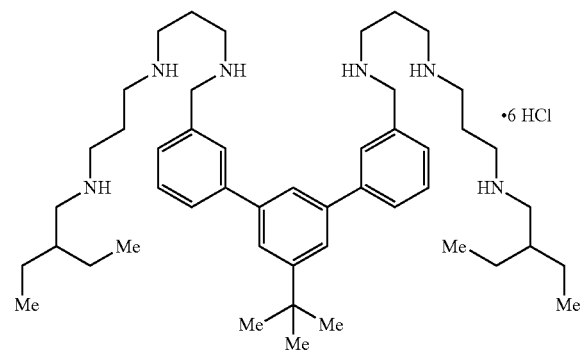 [SMILES: CCC(CC)CNCCCNCCCNCc1cccc(-c2cc(-c3cccc(CNCCCNCCCNCC(CC)CC)c3)cc(C(C)(C)C)c2)c1]

CZ-01-183: $N^1,N^{1''}$-((5'-(tert-butyl)-[1,1':3',1''-terphenyl]-3,3''-diyl)bis(methylene))bis($N^3$-(3-((2-ethylbutyl)amino)propyl)propane-1,3-diamine), hydrochloride salt $^1$H NMR (500 MHz, D$_2$O) δ ppm 7.80-7.68 (m, 7H), 7.59-7.50 (m, 4H), 4.32 (s, 4H), 3.24-3.13 (m, 16H), 2.99 (d, J=6.5 Hz, 4H), 2.18-2.14 (m, 8H), 1.66 (pent, J=5.5 Hz, 2H), 1.38 (s, 17H), 0.87 (t, J=6.5 Hz, 12H). $^{13}$C NMR (125 MHz, D$_2$O) δ ppm 153.4, 141.4, 140.5, 131.0, 129.8, 128.9, 128.5, 128.3, 123.6, 122.9, 51.2, 50.9, 44.8, 44.6, 43.9, 37.6, 34.5, 30.5, 22.6, 22.4, 22.4, 9.4. LRMS Calculated for C$_{48}$H$_{80}$N$_6$ m/Z 741.6 [M+H]$^+$, Obsd. 741.6 [M+H]$^+$.

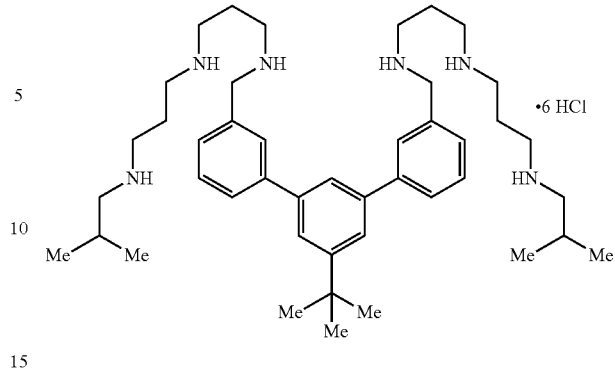

CZ-01-184: $N^1,N^{1''}$-((5'-(tert-butyl)-[1,1':3',1''-terphenyl]-3,3''-diyl)bis(methylene))bis($N^3$-(3-(isobutylamino)propyl)propane-1,3-diamine), hydrochloride salt $^1$H NMR (500 MHz, D$_2$O) δ ppm 7.75 (s, 2H), 7.71-7.67 (m, 4H), 7.63 (s, 1H), 7.54 (t, J=8.0 Hz, 2H), 7.46 (d, J=6.5 Hz, 2H), 4.28 (s, 4H), 3.23-3.10 (m, 16H), 2.89 (d, J=7.0 Hz, 4H), 2.19-2.08 (m, 8H), 1.98 (sept, J=6.5 Hz, 2H), 1.34 (s, 9H), 0.96 (d, J=7.0 Hz, 12H). LRMS Calculated for C$_{44}$H$_{72}$N$_6$ m/z 685.6 [M+H]$^+$, Obsd. 685.4 [M+H]$^+$.

Example 2: Antibacterial Activity of Triaryl Polyamines

The polyamine compounds were tested for antibacterial activity against four strains of bacteria: MRSA, *P. aeruginosa*, *A. baumannii*, and *E. coli*.

Materials and Methods

A clinical strain of MRSA, isolated from a patient who underwent arthroscopic knee surgery and characterized by ARUP Laboratories, Salt Lake City, Utah, was used for this study in addition to *Pseudomonas aeruginosa* ATCC 27853 and *Alcanivorax borkumensis* ATCC 700651. *P. aeruginosa* was resuspended in BHI broth, grown overnight at 37° C. and transferred to fresh BHI with 30% glycerol for storage at −80° C. The MRSA isolate was likewise stored in BHI with 30% glycerol at −80° C. Notably, the clinical MRSA isolate was not passaged more than three times prior to or during the study. Before performing MIC analysis and biofilm experiments, the frozen stocks of MRSA and *P. aeruginosa* were streaked onto Columbia blood agar plates and grown overnight at 37° C. *A. borkumensis* ATCC 700651 was resuspended from a lyophilized pellet into marine broth, grown overnight at 30° C. and passaged on marine agar plates prior to experimentation.

MIC Analysis

To determine the MIC of polyamine compounds, the protocol described herein was used. The MIC is defined as being the concentration of antimicrobial (in μg/mL) required to reduce the number of bacteria in a solution from 10$^5$ colony forming units (CFU)/mL to 10$^2$ CFU/mL in a 24-hour period.

In brief, a 0.5 McFarland of each bacterial isolate was made. A 0.5 McFarland is a measure of turbidity in a liquid sample that contains approximately 1×10$^{8}$ CFU/mL. The 0.5 McFarland standard was diluted in cation adjusted Mueller Hinton Broth (CAMHB), and 50 μL of broth were added to a well of a 96-well plate. In addition, 50 μL of CAMHB that contained a desired concentration of antimicrobial were also added to the well for a final volume of 100 µL and a final concentration of approximately $5\times10^4$ CFU/well (which equated to approximately $5\times10^5$ CFU/mL). Each well contained a desired amount of polyamine compound in order to experimentally determine the MIC. Each 96-well plate was incubated at 37° C. for 24 hours. The contents of each well were plated on tryptic soy agar (TSA). TSA plates were incubated for 37° C. for 24 hours after which the number of CFU were counted and used to calculate the CFU/mL that remained after exposure to varying concentrations of compound. This procedure was repeated n=8 times for each concentration of antimicrobial. The concentration of polyamine compound that reduced bacteria from $10^5$ CFU/mL to $10^2$ CFU/mL in 24 hours was considered the MIC.

MICs from selected triaryl polyamine compounds are provided in Tables 1 and 2.

TABLE 1

MIC, MBEC and EBEC of Polyamines Against MRSA and *P. aeruginosa*.

| | MRSA | | | *P. aeruginosa* | | |
|---|---|---|---|---|---|---|
| Compound | MIC (µg/mL) | MBC (µg/mL) | EBEC (µg/mL) | MIC (µg/mL) | MBC (µg/mL) | EBEC (µg/mL) |
| CZ-1-152 | 16 | 16 | | 32 | 32 | |
| CZ-1-153 | 16 | 16 | | >64 | >64 | |
| CZ-1-154 | 4 | 4 | | 32 | >32 | |
| CZ-1-155 | 16 | 16 | | 16 | 16 | |
| CZ-1-156 | 2 | 2 | | 32 | 32 | |
| CZ-1-157 | 4 | 4 | >750 | 16 | 16 | |
| CZ-1-161 | 1 | 2 | | 16 | 16 | |
| CZ-1-164 | 1 | 1 | | 16 | 16 | |
| CZ-1-166 | 1 | 1 | | 4 | 8 | |
| CZ-1-174 | 8 | 16 | | 64 | >64 | |
| CZ-1-176 | 32 | 32 | | 64 | 64 | |
| CZ-1-177 | 1 | 1 | 250 | 1 | >4 | |
| CZ-1-178 | 1 | 1 | <250 | 1 | >4 | |
| CZ-1-179 | 0.5 | 1 | 250 | 4 | 4 | |
| CZ-1-180 | | | | | | |
| CZ-1-182 | 0.25 | | 100 | 4 | | 150 |
| CZ-1-183 | 0.5 | | | 8 | | |
| CZ-1-184 | 0.5 | | | 16 | | |

TABLE 2

MIC, MBEC and EBEC of Polyamines Against *A. baumannii* and *E. coli*.

| | *A. baumannii* | | | *E. coli* | | |
|---|---|---|---|---|---|---|
| Compound | MIC (µg/mL) | MBC (µg/mL) | EBEC (µg/mL) | MIC (µg/mL) | MBC (µg/mL) | EBEC (µg/mL) |
| CZ-1-152 | | | | | | |
| CZ-1-153 | | | | | | |
| CZ-1-154 | | | | 16 | 16 | |
| CZ-1-155 | | | | | | |
| CZ-1-156 | | | | 16 | 16 | |
| CZ-1-157 | | | | | | |
| CZ-1-161 | 4 | 4 | | 1 | 1 | |
| CZ-1-164 | | | | | | |
| CZ-1-166 | | | | | | |
| CZ-1-174 | | | | | | |
| CZ-1-176 | | | | | | |
| CZ-1-177 | 8 | 16 | 500 | | | |
| CZ-1-178 | 2 | 4 | 500 | | | |
| CZ-1-179 | 2 | 4 | 500 | | | |
| CZ-1-180 | | | | | | |
| CZ-1-182 | 32 | | 300 | | | |
| CZ-1-183 | 16 | | | | | |
| CZ-1-184 | 64 | | | | | |

MBEC Analysis

To determine the MBEC of each polyamine compound, the MBEC Inoculation Tray by Innovotech, formerly known as the Calgary biofilm device, was used. Within this device, biofilms grow on the surface of polystyrene pegs, 96 of which are attached to a lid. These pegs are inserted into a flat bottom 96-well plate. In this instance, the MBEC of a molecule was defined as the concentration of compound (in µg/mL) required to reduce $10^5$ or $10^6$ CFU/peg (biofilm levels varied by isolate) to $10^2$ CFU/peg in a 24-hour period.

Following the manufacturer's guidelines, biofilms were grown on the surface of each peg by first making a 0.5 McFarland of each isolate. The 0.5 McFarland was diluted 1:100 in CAMHB. Into each well of a flat bottom 96-well plate, 150 µL of broth were pipetted. The plate was shaken at 100 rpm for 24 hours (*P. aeruginosa* and *A. baumannii*) or 48 hours (MRSA). The pegs were then placed into a separate flat bottom 96-well plate for 10 seconds with 200 µL of phosphate buffered saline (PBS) in each well to remove nonadherent cells. The lid was then placed into a 96-well plate that contained varying concentrations of antimicrobial with 200 µL per well. The plate was incubated for 24 hours at 37° C. after which time 100 µL of broth were plated on TSA. TSA plates were incubated 24 hours at 37° C. and the number of CFU counted to calculate the CFU/peg. In this instance, the MBEC was defined as the concentration of antimicrobial required to reduce $10^5$ or $10^6$ CFU/peg to $10^2$ CFU/peg in a 24 hour period.

The MBEC data are also presented in Tables 1 and 2 above.

EBEC Analysis

To determine the efficacy of polyamine compounds against high number biofilms, biofilms were grown on the surface of polyetheretherketone (PEEK) membranes using a membrane biofilm reactor. This reactor was similar to the CDC biofilm reactor, but rather than growing biofilms on coupon surfaces, the reactor was modified to hold PEEK membranes. In short, to grow biofilms within this system, 500 mL of brain heart infusion (BHI) broth were inoculated with 1 mL of a 0.5 McFarland. The reactor was placed on a hot plate set at 34° C. and the bacteria were grown under batch conditions for 24 hours. Following this protocol, biofilms typically grow to $10^9$ CFU/PEEK membrane, so each PEEK membrane had a high number of biofilms A solution of 10% BHI was then flowed through the reactor at a rate of 6.94 mL/min for an additional 24 hours. PEEK membranes were then removed and placed into 2 mL of CAMHB that contained a desired concentration of polyamine compound or antibiotic. The EBEC was defined as the concentration of antimicrobial required to reduce a biofilm from approximately $10^9$ CFU/PEEK membrane to approximately $10^2$ CFU/PEEK membrane in a 24-hour period.

The EBEC data are also presented in Tables 1 and 2 above.

Example 3: Wound Healing Study

Biofilm-impaired, difficult-to-treat wounds constitute a significant challenge that affect nearly all military and civilian healthcare facilities, and pose a unique challenge in the case of decubitus ulcers. Calhoun et al., CORR, 2008; Murray, J Trauma, 200; Murray, Crit Car Med, 2008. Compounding the problem is the current global threat of antibiotic resistance. CDC Threat Report, 2013; Wolcott et al., J Wound Care, 2010; Williams and Costerton, JBMR, 2011. To address these problems, a unique, first-in-class series of antibiofilm antibiotics has been developed that demonstrates a 2-in-1 ability to disperse and kill bacterial biofilms. These agents are referred to as CZ compounds and have been shown to display broad spectrum activity with reduced risk of resistance and focused activity against biofilms. In this study, in vivo analysis was performed using a porcine excision wound model to assess the efficacy of a leading CZ (CZ-1-179) as a topical agent against both planktonic and well-established biofilms that were used as initial inocula.

Methods

An IACUC-approved in vivo analysis utilized an excision wound model in swine. Up to 32 partial thickness wounds were created/animal using a 1 cm biopsy punch (FIG. 1A). Wounds were inoculated with ~1×10$^8$ colony forming units (CFU) of *A. baumannii* in the planktonic or biofilm phenotype. Well-established biofilms were grown on the surface of bio-absorbable collagen in a modified CDC biofilm reactor for 8 days (FIG. 1B). An n=8 wounds were used for each treatment group. Positive controls of infection were established and confirmed that infection would develop in wounds inoculated with either phenotype.

For the treatment groups, infection was allowed to establish in each wound for 5 days after which time treatment with an antimicrobial began. In one set of wounds, CZ-1-179 (2% concentration formulated in hyaluronic acid) was applied once daily for 2 weeks. A second set of wounds was treated with silver sulfadiazine (SSD) daily for 2 weeks. In a separate pig, wounds were inoculated as above and a combination of colistin/imipenem (2.5 mg/each) was administered IV for 14 days for comparison to the current clinical standard of care for *A. baumannii*. Lastly, a final pig was used wherein wounds were inoculated as above, IV colistin/imipenem was administered in combination with topical CZ-1-179 or SSD. Swine were monitored for 28 days. Wound size was measured daily. Culture swabs were collected regularly. At the time of necropsy, a 5 mm biopsy punch was used to collect tissue and calculate CFU/g using standard microbiological procedure. ANOVA analysis was used to compare differences in data with alpha 0.05.

TABLE 3

CFU/g of Tissue from the Various Wound Sets Inoculated with Planktonic Bacteria.

| (A) Planktonic Phenotype Group | CFU/g Tissue |
|---|---|
| Positive Control | 2.44 × 104 |
| Colistin/Imipenem only | 2.74 × 102 |
| SSD only | 0.00 |
| CZ 1-179 only | 0.00 |
| Colistin/Imipenem + SSD | 0.00 |
| Colistin/Imipenem + CZ 1-179 | 0.00 |

TABLE 4

CFU/g of Tissue from the Various Wound Sets Inoculated with Biofilm Bacteria.

| B) Biofilm Phenotype Group | CFU/g Tissue |
|---|---|
| Positive Control | 5.21 × 106 |
| Colistin/Imipenem only | 3.32 × 102 |
| SSD only | 0.00 |
| CZ 1-179 only | 0.00 |
| Colistin/Imipenem + SSD | 0.00 |
| Colistin/Imipenem + CZ 1-179 | 0.00 |

Figure 4:
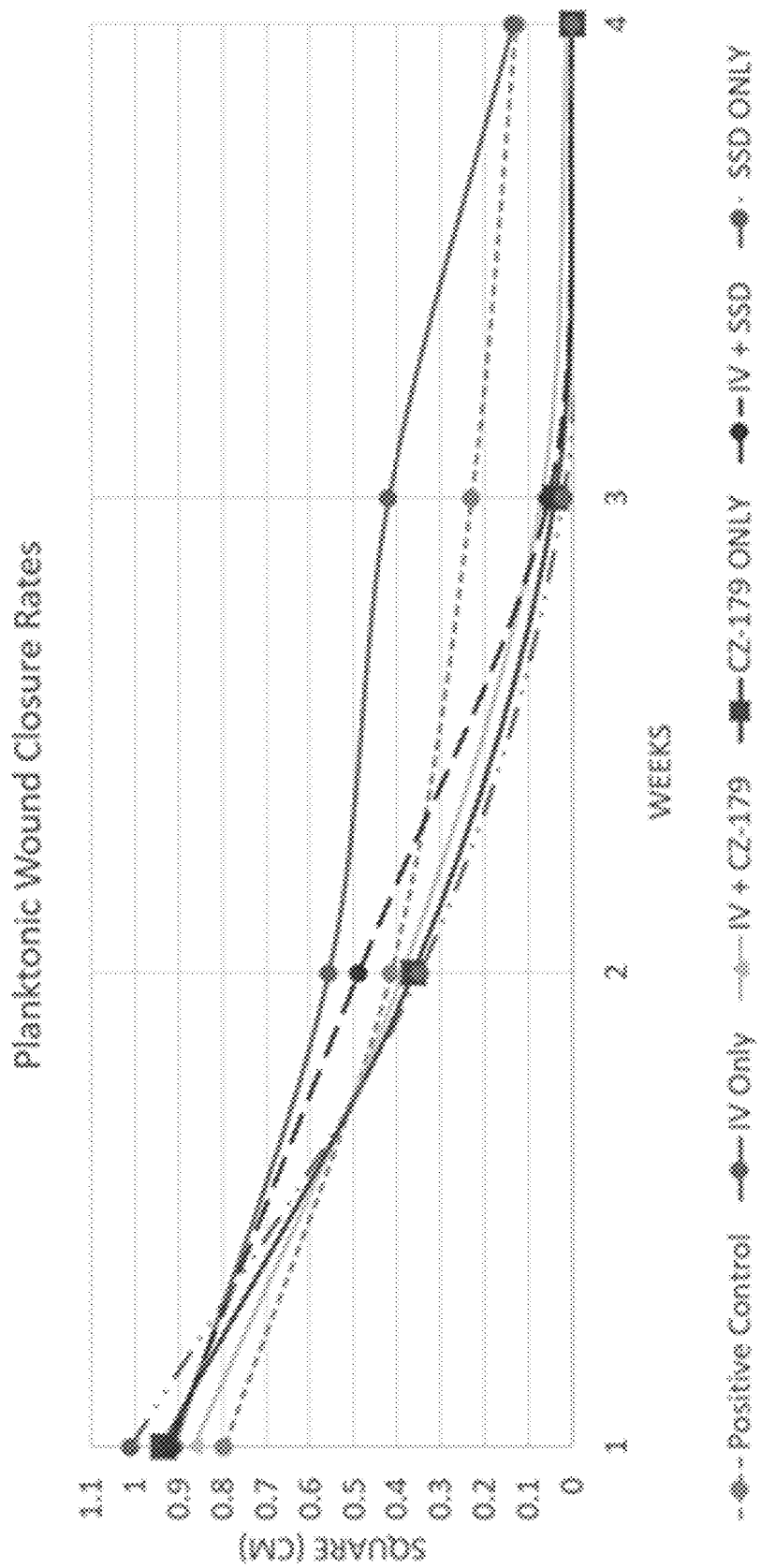
FIG. 4 shows the wound closures rates from the biofilm inoculations of Example 3 with controls.

The data indicated that wound closure rates were slowest in the pig that received IV only treatment (FIG. 4). Wounds that were inoculated with biofilms were on average ~0.1 cm$^2$ larger than wounds that had been inoculated with planktonic bacteria (FIG. 4).

Data further showed that wounds inoculated with well-established biofilms had ~2 log$_{10}$ units more bacteria compared to those inoculated with planktonic bacteria ($p<0.05$: see Tables 3 & 4). Wound infections on the swine treated with IV antibiotics resolved, however *A. baumannii* were never fully eradicated, leaving wound beds still colonized with the bacteria (~3×10$^2$ CFU/g tissue). In the swine treated with both IV and topical antimicrobials, SSD took 2 days longer to clear bacteria in wounds compared to CZ-1-179.

In this study, wounds inoculated with bacteria in the biofilm phenotype may harbor increased numbers of bacteria and had slower rates of closure. Data also indicated that a combination of therapies, e.g., IV+topical, can be more beneficial to treat and prevent biofilm-related infection, given that IV-only treatment allowed *A. baumannii* to remain colonized in wounds even after 2 weeks of therapy. CZ-1-179 appeared to eradicate *A. baumannii* faster than SSD. These data demonstrated that the inventive antimicrobial compounds are a promising advancement for treating and preventing biofilm-impaired wounds that are caused by well-established biofilms.

Example 4: Synthesis of CZ-1-179

To a stirring solution of a dicarbaldehyde (e.g., 5'-(tert-butyl)-[1,1':3',1''-terphenyl]-4,4''-dicarbaldehyde: 2.12 g, 6.22 mmol, 1 equiv.) in MeOH (100 mL) and DCE (25 mL) at 0° C. was added a diamine (e.g., N1-(3-aminopropyl)-N3-(2-ethylbutyl)propane-1,3-diamine: 3.61 g, 16.79 mmol, 2.7 equiv.) portion wise over the span of 20 min. The solution was then left to stir for 16 hr. NaBH$_4$ (0.95 g, 24.88, 1 equiv.) was subsequently added portion wise over the span of 20 min and the reaction was allowed to stir for an additional 1 hr. The solvent was then evaporated, and the crude solid was partitioned between EtOAc (500 mL) and 10% NaOH (250 mL). The NaOH phase was then washed with EtOAc (500 mL), and the combined organics were dried over Na$_2$SO$_4$. If desired, column chromatography can be performed using gradient conditions starting at (300:16:1 CH$_2$Cl$_2$:MeOH:NH$_4$OH).

The free base was acidified with HCl in MeOH (100 mL), then placed at 0° C. for 1 hr to precipitate. The corresponding precipitate was filtered and dried to afford the crude HCl salt as a white solid (25-52%). If the subsequent HCl salt remained impure, recrystallization with H$_2$O (solvent) and iPrOH (anti-solvent) helped ensure purity.

Synthesis of CZ-1-179 was successful and resulted in a unique antibiofilm compound N$^1$,N$^{1''}$-((5'-(tert-butyl)-[1,1': 3',1''-terphenyl]-4,4''-diyl)bis(methylene))bis(N$^3$-(3-((2-ethylbutyl)amino)propyl)propane-1,3-diamine), hydrochloride salt with the following characteristics: $^1$H NMR (500 MHz, D$_2$O) δ ppm 7.78-7.69 (m, 7H), 7.61 (bs, 4H), 4.38 (s, 4H), 3.26-3.20 (m, 16H), 3.01 (s, 4H), 2.17 (bs, 8H), 1.67 (bs, 2H), 1.38 (bs, 17H), 0.88 (s, 12H). $^{13}$C NMR (125 MHz, D$_2$O) δ ppm 153.4, 141.8, 140.4, 130.4, 129.7, 127.8, 123.8, 122.9, 50.9, 50.9, 44.9, 44.6, 43.9, 37.6, 34.4, 30.5, 22.6, 22.4, 22.4, 9.4. IR (neat): 3334 (bs), 2963, 2766, 1457 (all s) cm$^{-1}$. mp decomposition (180-184° C.). LRMS Calculated for C$_{48}$H$_{80}$N$_6$ m/z 741.6 [M+H]$^+$, Obsd. 370.7 [M+H]$^+$/2.

Example 5: In Vitro Efficacy of CZ-1-179

During screening of the CZ series, CZ-1-179 displayed broad spectrum activity against biofilms of methicillin-resistant *Staphylococcus aureus* and *Pseudomonas aeruginosa*. Given its promising activity, a focused approach was taken in this study to assess the efficacy of CZ-1-179 against *Acinetobacter baumannii* in the planktonic and biofilm phenotype. Before testing CZ-1-179 in an in vivo pig model, in vitro activity against *A. baumannii* was determined. This was conducted using the isolate in both the planktonic and biofilm phenotypes.

Methods

Silver sulfadiazine (SSD) powder was used for in vitro analyses The bacterial isolate was from the American Type Culture Collection (ATCC) and was *A. baumannii* ATCC BAA 1605. The isolate was maintained on Columbia blood agar and passaged as necessary with overnight incubation at 37° C. Sodium hyaluronate (HA; Research Grade HA15M 1.01 MDa-1.8 MDa) was used. Vascular access ports (VAP), VAP catheters (7 French size×36") and accompanying Posi-Grip Huber point needles (22 gauge at ¾") were used in two sizes—ClearPort Medium or SwirlPort Max—with the SwirlPort Max being the better option for locating the device subdermally. Digital images were collected using a Nikon D90 camera.

Planktonic Efficacy

Minimum inhibitory concentration (MIC) testing against the planktonic phenotype was performed first. To do so, a modified protocol of the Clinical and Laboratory Standards Institute (CLSI) guideline M100 was used. In short, using a fresh overnight culture of bacteria, a 0.5 McFarland standard was made in PBS using a nephelometer, then diluted to achieve a concentration of ~7.5×10$^5$ CFU/mL. A 96-well plate was set up such that a final volume of 100 μL was present in each well. Column 1 served as the negative control of growth (antibiotic only without bacteria added) and Column 11 served as the positive control of growth (bacteria only, no antibiotic).

To accomplish this, 100 μL of CAMHB that contained CZ-1-179 only (256 μg/mL stock) was pipetted into each well of column 1. Into columns 2-11, 50 μL of CAMHB were added to each well. Subsequently, 50 μL of CAMHB that contained a concentration of 256 μg/mL CZ-1-179 were added to each well of column 2 using a multi-channel pipet. The solution was mixed, then 50 μL were removed and added to wells of column 3. This 1:2 dilution process was continued through column 10. Lastly, into each well of columns 2-11, 50 μL of the prepared bacterial solution were added. This process resulted in a range of antibiotic testing from 64 μg/mL to 0.0625 μg/mL. The 96-well plate was covered with adhesive film and incubated 24 hr at 37° C. The concentration of antibiotic that inhibited pellet formation or turbidity was considered the MIC. MIC determination was likewise performed with SSD using the same procedure.

Biofilm Efficacy

Biofilms were grown on polycarbonate coupons in a CDC biofilm reactor following the manufacturer's recommendation. Once assembled and autoclaved, the reactor was inoculated. To do so, a fresh overnight culture of *A. baumannii* was used to make a 0.5 McFarland standard of the bacterial isolate (~5×10$^7$ CFU/mL). One mL of the 0.5 McFarland solution was inoculated into 500 mL of BHI in the CDC biofilm reactor. The reactor was placed on a hot plate set at 34° C. and a baffle rotation of 130 rpm for 24 hr. After 24 hr batch growth, a continuous flow of 10% BHI was flowed through the reactor at ~6.9 mL/min for an additional 168 hr (7 days).

Following 192 hr (8 days) of total growth, coupons were aseptically removed and placed into 2 mL of CAMHB that contained CZ-1-179. CZ-1-179 was tested at multiple concentrations—0.00125% (12.5 μg/mL), 0.0025% (25 μg/mL), 0.005% (50 μg/mL), 0.00625% (62.5 μg/mL), 0.0125% (125 μg/mL), 0.025% (250 μg/mL) 0.05% (500 μg/mL), 1.0% (10 mg/mL) and 2.0% (20 mg/mL)—in order to obtain a profile of in vitro efficacy. Biofilms were exposed to CZ-1-179 for 24 hr at 37° C. after which time coupons were vortexed for 1 min, sonicated at 42 kHz for 10 min and vortexed again for ~10 sec. A 100 μL aliquot of broth was removed and plated using a 10-fold dilution series in order to quantify the CFU/coupon that remained. Testing was performed with n=3 repeats per concentration. A baseline of growth was determined by quantifying n=3 coupons/reactor immediately following growth.

After obtaining the initial profile of CZ-1-179 antibiofilm efficacy in broth solution, additional testing was performed to confirm that when formulated in a gel, CZ-1-179 would maintain activity against biofilms. A CDC biofilm reactor was once again used to grow biofilms for analysis. In this case, biofilms were grown on absorbable collagen to more closely model a physiological environment. To grow biofilms on collagen, blank reactor arms were modified to hold collagen plugs. Specifically, four holes of 8.5 mm diameter each were drilled in the lower portion of a blank polypropylene holder. Collagen was aseptically removed from packaging and cut into coupons (1 cm diameter×0.3 cm height) using a sterile scalpel. Coupons were sterilely loaded into modified reactor arms that had been autoclaved previously. Once assembled, the CDC biofilm reactor was inoculated and biofilms were grown as described.

CZ-1-179 was formulated in a gel by combining the antibiotic powder in sterile PBS to a final concentration of 2% (20 mg/mL) and mixing thoroughly. HA powder was then added to a final concentration of 1.5% and mixed by shaking until dissolved. The formulation was allowed to gel at room temperature for a minimum of 2 hr, but had best results when allowed to gel overnight (air bubbles were no longer present). Approximately 1 mL of CZ-1-179 gel was placed into a single well of a 12-well plate. A collagen plug was removed from the CDC biofilm reactor and placed on the gel. The collagen plug was then covered with an additional ~1 mL of gel so that the biofilms on collagen were submerged in ~2 mL of gel. Samples were incubated 24 hr at 37° C., then quantified as described above to determine the remaining CFU/coupon. Data were collected with n=3 repeats and CZ-1-179 was tested at both 1% and 2% concentrations in the gel formulation.

To compare CZ-1-179 to an agent that is commonly used clinically in topical formulations, antibiofilm efficacy of SSD was also determined. Biofilms were grown on collagen as described. The efficacy of SSD was tested first in broth solution at concentrations of 0.05% (500 μg/mL) and 0.025% (250 μg/mL) following the procedures above. In addition to broth susceptibility testing, efficacy testing was also performed with clinically-relevant SSD cream (final concentration of 1% SSD) following the same 12-well plate method outlined above.

In Vitro Analyses

The MIC of CZ-1-179 against *A. baumannii* was 2 μg/mL. The MIC of SSD was also 2 μg/mL. Baseline biofilm growth on polycarbonate coupons resulted in ~7.5×10$^7$ CFU/coupon. SEM images showed that biofilms of *A. baumannii* grew to maturity and formed three-dimensional sheet-like structures across the surface. When exposed to CZ-1-179 in CAMHB, full eradication of biofilms was achieved at concentrations from 2% (20 mg/mL) down to 0.005% (50 μg/mL). When exposed to CZ-1-179 at 0.0025% (25 μg/mL), there were ~4.8×10$^3$ CFU/coupon (~4 log$_{10}$ reduction), and at 0.00125% (12.5 µg/mL) there were ~9.2×10$^5$ CFU/coupon (~2 log$_{10}$ reduction). Biofilms exposed to SSD in CAMHB were not fully eradicated. At 0.025% (250 µg/mL) there were ~5×10$^3$ CFU/coupon (~4 log$_{10}$ reduction) and at 0.05% (500 µg/mL) there were ~2.5×10$^3$ CFU/coupon (~4 log$_{10}$ reduction).

Baseline biofilm growth on collagen coupons resulted in ~5.8×10$^7$ CFU/coupon, which was similar to growth levels on polycarbonate. At 1% and 2% concentrations, CZ-1-179 gel eradicated biofilms of *A. baumannii* completely. In contrast, when exposed to SSD cream (at 1%), biofilms were reduced by ~3 log$_{10}$ units to ~5.9×10$^4$ CFU/coupon. The in vitro outcomes supported advancement of CZ-1-179 toward in vivo analysis.

Example 6: In Vivo Efficacy of CZ-1-179

In vivo efficacy of CZ-1-179 was tested in a porcine excision wound model. Animal models of biofilm-impaired wound infections have primarily been developed using planktonic bacteria as initial inocula. Wounds inoculated with bacteria in the biofilm phenotype, however, may harbor increased numbers of bacteria and have slower rates of closure.

CZ-1-179 was formulated as the active ingredient in a topical formulation for in vivo evaluation of its ability to treat and prevent wound infection caused by *A. baumannii* in both the planktonic and biofilm phenotypes. For comparison, current standards of care including IV (colistin/imipenem) and topical (silver sulfadiazine) therapies were also tested.

Animal Acclimation and Surgical Procedure

Four Yorkshire pigs with weight in the range of approximately 40-50 kg were quarantined for a minimum of 7 days. Positive reinforcement (Swedish Fish®, marshmallows, Snickers® bars, fruit and/or other treats) was provided once daily to help the pigs become accustom to having their back manipulated—e.g., a back scratch with a soft brush—by a research team member. A custom-fit jacket was also placed on pigs during the acclimation period to allow them to become aware of the covering that would be on their body.

The night before a surgical procedure was to be performed, pigs were fasted. To perform surgery, pigs were anesthetized initially with a combination of tiletamine-zolazepam (Telazol®; 4.4 mg/kg), Ketamine (2.2 mg/kg) and Xylazine (2.2 mg/kg). Pigs were intubated, given isoflurane inhalant at 0.5-5.0%, transported to a surgical suite, placed in sternal recumbency and clipped/razor-shaved of hair in the region where excision wounds would be created. Pigs were rotated to dorsal recumbency and the jugular vein area was sterilely prepped using alternating betadine/isopropyl alcohol. Once prepped, the site was sterilely draped and a VAP was implanted. To do so, a ventral midline incision was made to isolate the jugular vein. A catheter was placed in the vein and secured. A second incision was made on the dorsal side of the neck and a tunnel created along the subcutaneous space from the second incision to the jugular vein. The catheter was passed through the tunnel. A VAP was anchored subdermally in the dorsal neck space with non-absorbable suture (e.g., Proline). The catheter was connected to the VAP and secured in the jugular vein. Both incision sites were closed using absorbable suture (e.g., Vicryl). One of the four pigs (i.e., the one used for positive and negative control wounds) did not have a VAP implanted, as it did not require blood draws or injections.

With a VAP in place, a pig was rotated to sternal recumbency. The back was sterilely prepped for surgery, then draped. Using a 1 cm biopsy punch, excision wounds were created with a separation of approximately 2 cm between each wound. Wounds were organized into three or four sections with n=8 wounds/section (see FIG. 5). To reduce bleeding during wound creation, wound beds were treated with µL quantities of dilute epinephrine (1 mg/mL) as needed by the surgeon. Sterile saline-soaked gauze sponges were placed on excised wounds to maintain moisture as additional wounds were created. Once created, wounds were inoculated with bacteria (with the exception of negative control wounds) in either the planktonic or biofilm phenotype (see FIG. 5).

Bacterial Inoculation

For wounds inoculated with planktonic bacteria, 2-3 colonies from a fresh overnight culture of *A. baumannii* were adjusted to a turbidity of 10% (~1×10$^9$ CFU/mL) in sterile PBS using a nephelometer. One hundred L were pipetted into wound beds on the left flank of an animal (see FIG. 5). This resulted in an inoculum of ~1×10$^8$ CFU of planktonic bacteria/wound.

Biofilm inoculation was performed by first growing biofilms on absorbable collagen for a total of 192 hrs (8 days) as described and transported to the OR in approved containers. Once the excision wounds were created, biofilm-containing collagen coupons were aseptically placed into wounds (one coupon/wound) on the right flank of an animal (see FIG. 1). Notably, a subset of collagen coupons from each reactor run were kept in the lab and quantified in order to obtain a baseline of biofilm growth. Following inoculation, tincture of benzoin was applied to the border of each wound section to help maintain bandage adherence. Wounds were bandaged with a non-stick Telfa pad and Tegaderm. A custom jacket was also placed to further protect bandaging. Pigs were recovered and allowed to eat and drink ad libitum.

All wounds were reinoculated with planktonic or biofilm bacteria once daily for 3 days following the surgical procedure (total of 4 inoculations). Multiple inoculations were found to result in delayed healing and increased infection signal in each wound set. To perform the reinoculations, planktonic bacteria were made fresh each day. Likewise, multiple biofilm reactors were set up sequentially such that wounds were reinoculated with biofilms that had been grown for a total of 8 days in each case.

Study Design, Antibiotic Administration and Bandage Changes

The in vivo portion of this study was designed to determine the efficacy of CZ-1-179 as a stand-alone topical gel product and as an adjunct therapy with clinically-relevant IV antibiotics. An additional objective of this study was to compare the efficacy of a CZ-1-179 gel to a clinically-relevant SSD cream. As a general overview, wounds in Pig 1 served as positive and negative controls of infection (see FIG. 1). Wounds in Pig 2 were treated with topical CZ-1-179 gel (2% active) or SSD cream (1% active; see FIG. 1). Pig 3 received IV antibiotics only (FIG. 1). Wounds in Pig 4 were treated with both topical products and IV antibiotics (FIG. 1).

All antibiotic therapies began on Day 5 following surgery. To outline the specifics of antibiotic administration, in Pig 2-0.3 mL of CZ-1-179 gel was applied to each wound in sections 1 & 2, and ~0.3 mL of SSD cream applied to each wound in sections 3 & 4 once daily for 14 days (see FIG. 1). In Pig 3, colistin and imipenem were administered IV (via the VAP) in combination, with each at a dose of 2.5 mg/kg, twice daily for 14 days. These same regimens were followed for Pig 4 with both topical and IV antibiotics being administered in the same pig (see FIG. 1).

To maintain the VAPs in those pigs that had one, after it was initially implanted, it was locked with heparin solution (~5 mL with heparin at a concentration of 100 IU/mL). Following each use, it was flushed/locked with ~5 mL of heparin solution. When not in use, the VAP was flushed every 7-10 days with heparin solution.

Bandages were changed once daily on each pig. To do so, a trough/bucket was filled with feed and topped with treats for positive reinforcement. As the pig ate, the jacket and bandaging were aseptically removed. Digital pictures were taken of each wound section. A ruler was placed against the skin allowing for wound size measurements to be made. Culture swabs were collected of each wound (approximately twice weekly) to qualitatively confirm the presence of the inoculum, *A. baumannii*. Half of the wounds in each wound set were lightly debrided with sterile forceps and saline, whereas the other half remained undebrided. The rationale was to determine the influence that debridement would have on levels of bacteria in either the planktonic or biofilm phenotype. Following debridement or lack thereof, topical antibiotic therapy was applied. Wounds were bandaged once again and the jacket replaced. In pigs that received IV antibiotics, they were administered after the jacket was in place.

Necropsy and Microbiology

Each pig was monitored to an endpoint of 28 days after which each was sedated initially (as above) and humanely euthanized. To perform necropsy, bandages were aseptically removed. Culture swabs were taken of each wound site, plated on Columbia blood agar and incubated overnight for semi-quantitative and morphological analysis. Digital images were collected and wound sizes (height and width) measured. A 0.5 cm biopsy punch was then used to collect a tissue sample of each excised wound. For undebrided wounds, eschar, if present, was removed first, then a tissue punch collected. This prevented quantification of bacteria/biofilm that may have resided in eschar. To collect a tissue sample, the outer rim of a sterile biopsy punch was placed on the outer-most edge of the original wound margin. Each tissue sample was weighed, then placed in a tissue grinder tube that contained 1 mL of sterile saline. Tissue was ground for approximately 2 minutes. An aliquot of 100 μL was removed and plated using a 10-fold dilution series to quantify CFU/g of tissue.

Statistical Analysis

Bacterial counts and wound measurements were compared between groups and sections using a one-way ANOVA analysis with alpha level at 0.05. Descriptive statistics and LSD Post-hoc analysis were used for interpretations. Data were analyzed in SPSS v17.0 software.

In Vivo Analyses

Infection Signal

Figure 6:
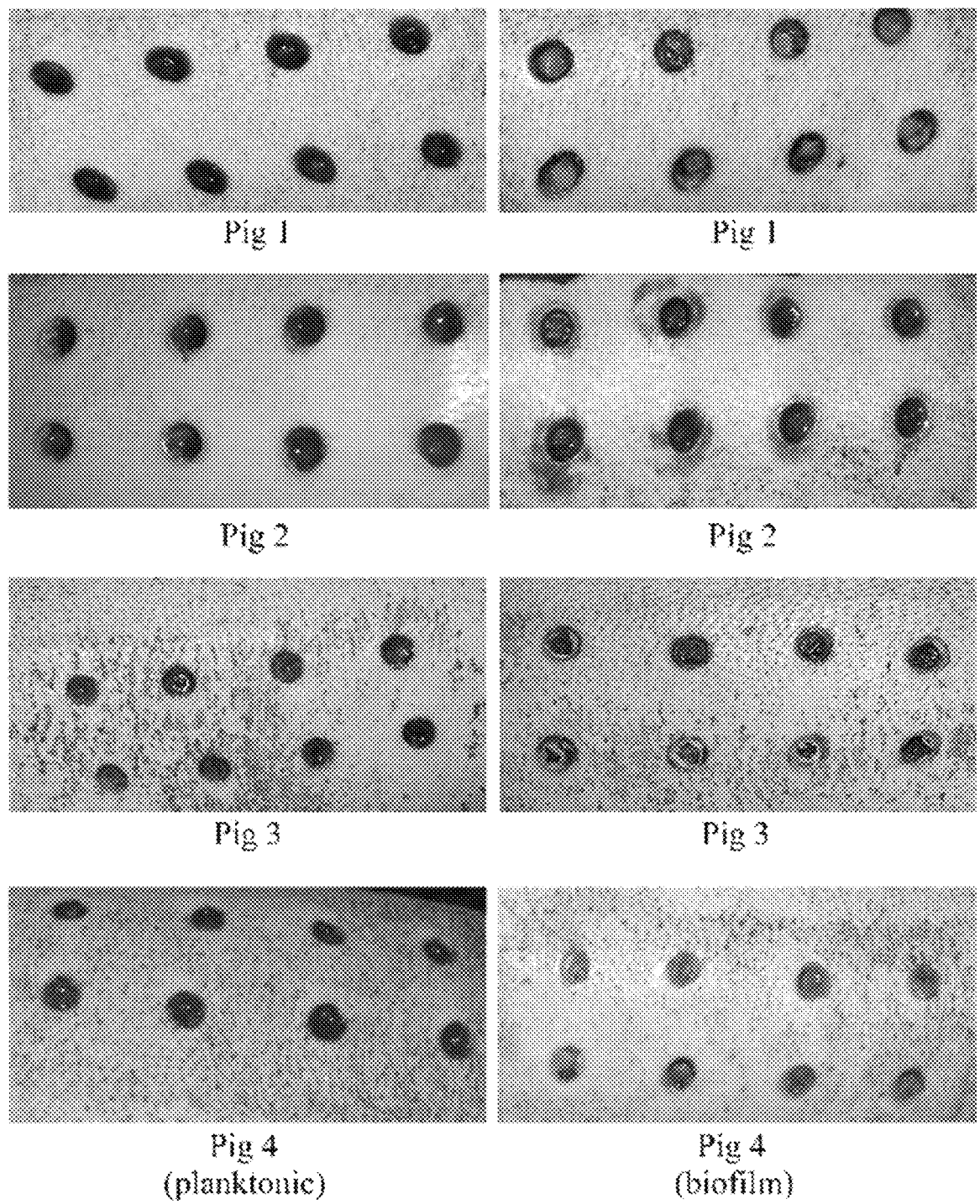
FIG. 6 provides representative images of infected wounds 3-4 days after surgery. Wounds inoculated with planktonic bacteria are shown in the left panel. Wounds inoculated with well-established biofilms are shown in the right panel. In Pig 1 (right panel), wounds are shown that had been lightly cleansed of discharge and inoculated with fresh collagen plugs on which biofilms were grown. Pig 2 had noticeably more redness develop around wound borders with biofilm versus planktonic bacteria inocula. The wounds of Pig 3 and 4 demonstrate the noticeable amount of purulence in biofilm wounds compared to planktonic wounds, which predominantly had serous discharge.
Figure 7:
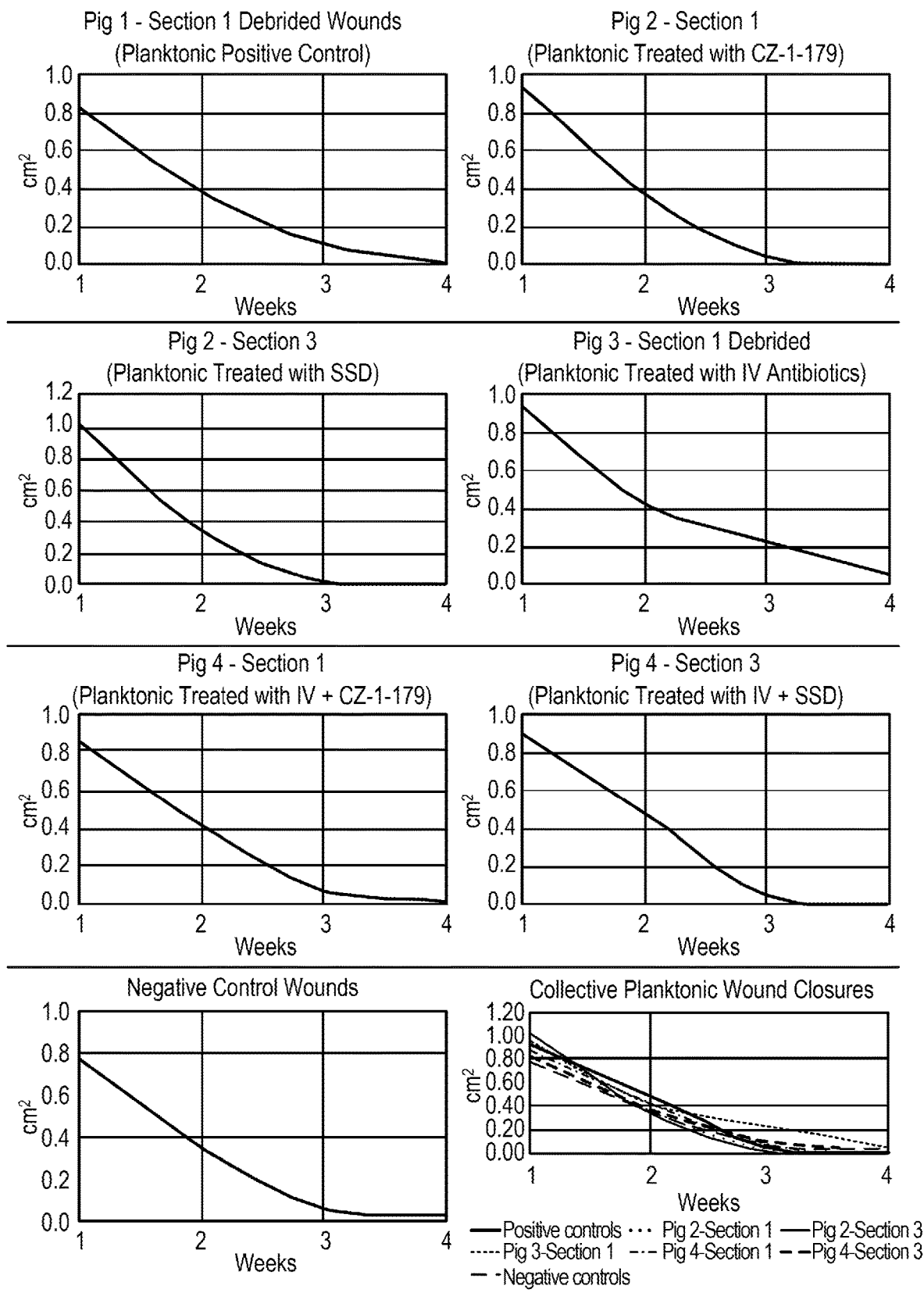
FIG. 7 provides measurements of planktonic bacteria-inoculated wounds over the course of the monitoring period. Each section of a pig back and its treatment regimen (see FIG. 5) is represented individually and in comparison on a collective graph. Data showed that wounds treated with IV antibiotics closed at the slowest rate. Wound diameters in Pigs 1, 2 & 4 varied slightly from Weeks 1 to 3, but were similar by the endpoint.

In all pigs, a modest positive signal of infection developed in each wound that was inoculated with bacteria of either phenotype. In the early stages of infection (2-3 days post-surgery), wounds inoculated with planktonic bacteria had moist, serous discharge with raised borders, redness and inflammation (FIG. 6). In contrast, wounds inoculated with biofilms had a dryer wound bed appearance, notable purulence with less serous discharge compared to planktonic wounds. In general, wounds inoculated with biofilms had slightly more pronounced irritation, redness and inflammation, in particular in Pig 2 (FIG. 6).

Infection Resolution, Wound Closure and Reepithelialization

In Pig 1 (control wounds) clinical signs of infection began to resolve in debrided planktonic and biofilm wounds by Day 10 and 8, respectively. Early granulation tissue and contraction were observed by those times. By Day 20 and beyond, all debrided positive control wounds were largely healed with no clinical signs of infection. To try and define the point at which infection resolved in undebrided wounds would not have been accurate as the wound bed, granulation, reepithelialization and contraction levels could not be deciphered with confidence due to the presence of eschar. In negative control wounds, granulation tissue began to develop by Day 6. Reepithelialization and contraction were obvious by Day 10.

Figure 8:
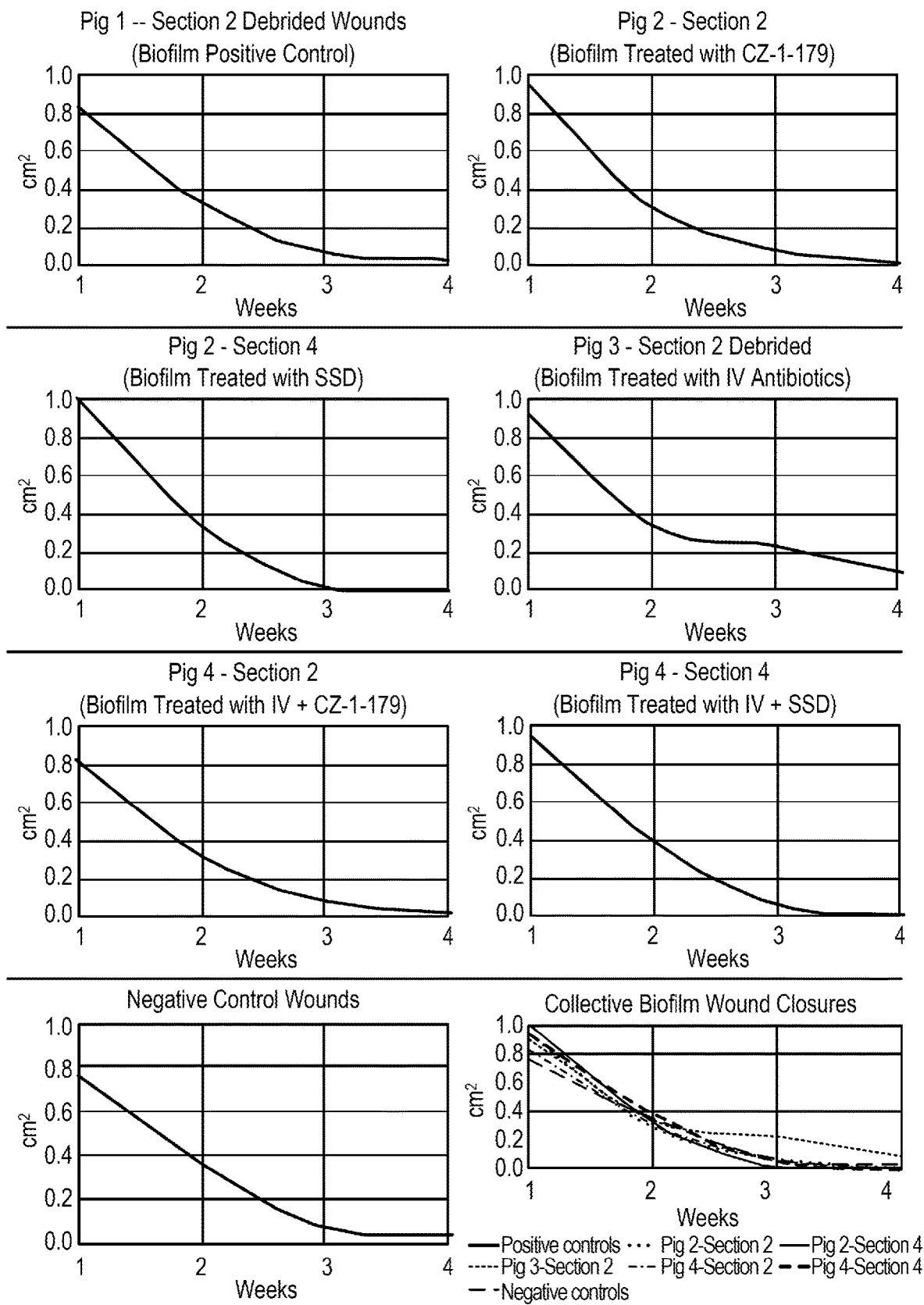
FIG. 8 provides measurements of biofilm-inoculated wounds over the course of the monitoring period. Each section of a pig back and its treatment regimen (see FIG. 5) is represented individually and in comparison on a collective graph. Similar to planktonic wounds, data showed that wounds treated with IV antibiotics closed at the slowest rate. Wound diameters in Pigs 1, 2 & 4 varied slightly from Weeks 1 to 3, but were similar by the endpoint.

Wound measurements of Pig 1 were collected on debrided wounds only. Measurements of undebrided wounds would have been skewed due to presence of eschar. However, qualitative observation indicated that undebrided wounds, particularly those inoculated with biofilms, took noticeably longer to heal/reepithelialize, did not have a healthy appearance for up to three weeks and harbored more bacteria as shown by culture data (see below). Closure of debrided wounds progressed steadily until the 28-day (4-week) timepoint (FIGS. 8 & 9). Wound diameters of planktonic and biofilm wounds were not statistically significantly different by Week 3 or 4 ($p=0.07$). Similarly, diameters of negative control wounds were not significantly different than positive controls by Week 3 or 4 ($p=0.06$).

In Pig 2 (topical treatments only), wounds that were treated with CZ-1-179 gel had mild redness around borders on Day 6 (24 hours after the first application), but no pus or discharge. Early granulation tissue was observed in planktonic and biofilm wounds. By Day 8 all CZ-1-179-treated wounds had taken a noticeable shift toward healing. Granulation tissue was abundant and contraction had advanced in all wounds. Wounds that were treated with SSD cream took roughly one day longer to clear infection. Signs of infection were present in particular in planktonic wounds on Day 7 with pus, discharge and redness along borders. However, similar to CZ-1-179 gel-treated wounds, by Day 8 wounds treated with SSD had taken a notable shift toward healing. Granulation tissue was abundant and contraction was obvious.

Figure 5:
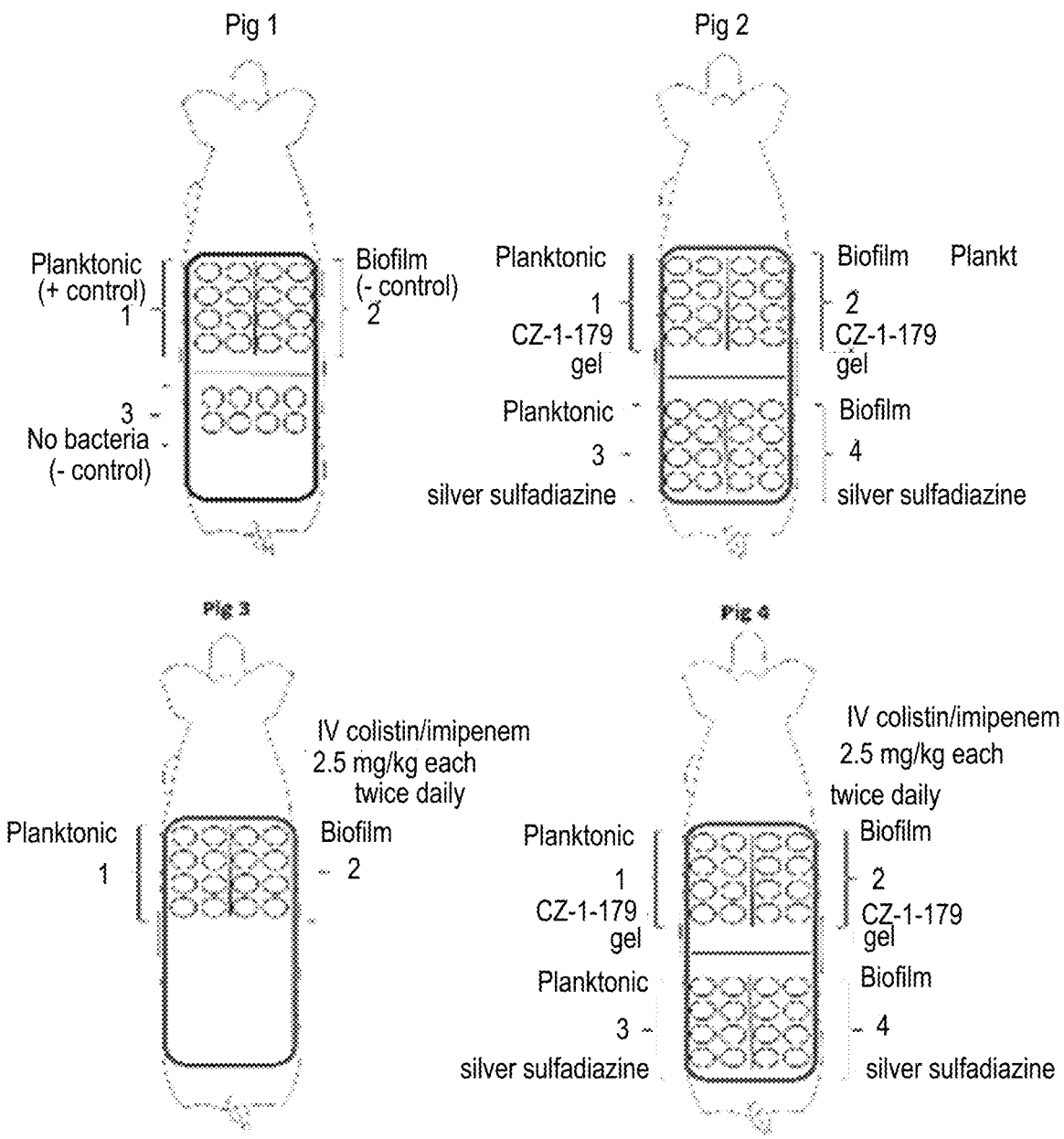
FIG. 5 provides a schematic of each pig, inoculation patterns and antimicrobial treatments that were given. Wounds on the left flank of each pig were inoculated with planktonic bacteria and wounds on the right flank of each pig were inoculated with well-established biofilms. Wounds were divided into 2-4 sections on each pig back with n=8 wounds/section.

All wounds in Pig 2 reepithelialized almost fully (>90%) by Week 3 (FIGS. 5 & 6). Compared to other animals on study, Pig 2 wounds closed soonest (see FIGS. 8 & 9) and were the healthiest visually. By the endpoint, there were no statistically significant differences in diameters between wounds treated with CZ-1-179 or SSD, or when compared to positive control wounds ($p>0.09$ in all cases). Notably, CZ-1-179 gel did not cause rash, necrosis or adversely affect healing.

In Pig 3 (IV antibiotics only), clinical signs of infection in both planktonic and biofilm wounds that were debrided had resolved by Day 9. Granulation tissue and contraction had begun by Day 9 as well. Interestingly, wound closure stagnated during the period that IV antibiotics were administered, in particular in biofilm wounds (FIGS. 8 & 9). Wounds in Pig 3 had the largest diameters, were the slowest to close for both planktonic and biofilm wounds (FIGS. 8 & 9), and diameters were significantly different compared to all wounds in Pig 1, 2 and 4 by the endpoint ($p<0.008$ in all cases).

In Pig 4 (IV+topical products), signs of infection in wounds that were treated with topical CZ-1-179 resolved by Day 6. The beginning of wound contraction was notable by Day 7 in both planktonic and biofilm-inoculated wounds and as in Pig 2, by Day 8 healing was obvious. In contrast, wounds that were treated with SSD had significant infection (i.e., pus, discharge, redness) on Day 6 and did not resolve until Day 10. Wound contraction was notable by Day 9 in planktonic wounds and notable in biofilm wounds by Day 10. Healing was obvious by Day 12. By the endpoint, the only significant difference in wound diameters of Pig 4 was between Pig 3 (p=0.001) and negative control wounds (p=0.007).

In summary, wounds treated with CZ-1-179 gel were clear of infection 1 to 3 days sooner than wounds treated with SSD cream in planktonic or biofilm inoculated wounds. CZ-1-179 also cleared signs of infection 3-4 days sooner than the host alone.

Culture Data

Culture data showed distinct differences between debrided and undebrided wounds in Pig 1. In Pig 3, bacteria were cultured in all wound types throughout the course of the study, which indicated that although infection resolved in wounds of Pig 3 that were treated with IV antibiotics, bacteria still colonized the wounds. Topical products used in Pigs 2 and 4 kept wounds moist and debridement was largely unnecessary as little to no eschar formed. Nevertheless, data from Pigs 2 and 4 in this section is presented as debrided versus undebrided wounds for ease of comparison. Culture data for debrided wounds is presented in Table 5. Data for undebrided wounds is presented in Table 6.

In Pig 1, *A. baumannii* was identified in at least one positive control wound throughout the 28-day monitoring period (Table 5). However, the host immune system was largely able to eradicate planktonic bacteria in debrided wounds. Only one colony of *A. baumannii* was detected by culture at necropsy, whereas tissue samples were negative (Table 5). In contrast, wounds that had been inoculated with biofilms and that were debrided had greater than $10^5$ CFU/g tissue at necropsy (Table 5). Undebrided wounds harbored more bacteria in both the biofilm and planktonic phenotype, with biofilm wounds having a higher bioburden (Table 6).

Culture swabs that were collected from Pig 2 (topical agents only) showed that on Day 6 post-surgery, CZ-1-179 gel had eradicated the majority of *A. baumannii* in all wounds (Tables 5 & 6). *A. baumannii* was detected in 2/8 wounds that were inoculated with planktonic bacteria and 3/8 wounds that were inoculated with biofilms. Beyond Day 6, *A. baumannii* was no longer detected by culture swab in wounds that were treated with CZ-1-179. Tissue samples collected at necropsy (Day 28) were also negative for growth (Tables 5 & 6). In the case of wounds in Pig 2 that were treated with topical SSD, on Day 6 post-surgery *A. baumannii* was cultured in 2/8 wounds that had been inoculated with planktonic bacteria, and 7/8 wounds that were inoculated with biofilms. After Day 12, *A. baumannii* was no longer detected by culture, and tissue samples collected at necropsy were also negative (Tables 5 & 6).

In Pig 3 (IV antibiotics only), *A. baumannii* was detected in all wounds throughout the 28-day monitoring period. Tissue samples collected at necropsy had approximately $10^2$ CFU/g in all wounds inoculated with planktonic or biofilm bacteria (Tables 5 & 6).

Culture data from Pig 4 (IV+topical products) showed that on Day 6, none of the wounds treated with CZ-1-179 had detectable *A. baumannii*. However, 10 days post-surgery a culture swab identified 3 colonies of *A. baumannii* in one of the biofilm-inoculated wounds, 14 days post-surgery cultures identified an additional few colonies in a second biofilm-inoculated wound, and 17 days post-surgery one wound that had been inoculated with planktonic bacteria identified a few colonies (see Tables 5 & 6). Tissue samples were negative for growth at necropsy (Tables 5 & 6). Wounds in Pig 4 that were treated with SSD all had significant growth on Day 6 post-surgery. On Day 10, one debrided wound that had been inoculated with biofilms had 2 colonies of growth, on Day 15 a single colony was identified in a wound that had been inoculated with planktonic bacteria, on Day 17 one colony was identified in a biofilm wound, and on Day 28 a single colony was identified in a biofilm wound (Tables 5 & 6). Tissue samples that were collected and quantified at necropsy showed no positive growth for *A. baumannii*.

ANOVA analysis showed that the number of bacteria in undebrided biofilm wounds of Pig 1 were significantly different than the number of bacteria in all other wound groups amongst all pigs (highest p=0.001). No statistically significant differences were found in bacterial numbers between any other wound groups of any pigs (lowest p=0.79).

In summary, the topical products used alone and in combination were able to eradicate bacteria in both the planktonic and biofilm phenotypes more effectively than IV antibiotics alone. CZ-1-179 gel reduced the bioburden of planktonic and biofilm bacteria slightly faster than SSD cream, yet both were able to treat infection, assisted wound healing and did not adversely affect host tissue.

Discussion

The infection signal in young healthy pigs was mild (FIG. 6), but significant enough to assess outcome measures. Pig 1 was able to clear infection and rid wounds of planktonic bacteria naturally, in particular in debrided wounds (Table 5). However, wounds inoculated with well-established biofilms harbored more bacteria in both debrided and undebrided wounds (Tables 5 & 6). These results supported the hypothesis that wounds inoculated with well-established biofilms would harbor more bacteria, and indicated that there may be important differences to consider in wounds inoculated/contaminated with biofilms versus planktonic bacteria. Similar differences have been observed in sheep studies wherein planktonic or biofilm bacteria were used as initial inocula.

In vivo data from Pig 2 indicated that CZ-1-179 gel was effective. The gel maintained moist wound beds, reduced eschar formation, eradicated bacteria in both phenotypes and expedited closure. SSD cream performed similarly, but required slightly longer time intervals, in particular when used in combination with IV antibiotics, to eradicate bacteria. It was important to note that CZ-1-179 gel did not adversely affect wound healing or lead to necrotic tissue.

Wounds in Pig 3 treated with IV antibiotics struggled to heal fully. A two-week course of IV colistin/imipenem antibiotics failed to reduce planktonic bacteria in debrided wounds to a greater degree than positive control planktonic wounds that were debrided (Table 5). The antibiotics were successful at reducing bioburden to a greater degree in the other wound types (Tables 5 & 6). Nevertheless, the finding that bacteria in both the planktonic and biofilm phenotype were still present in wounds that were treated with IV antibiotics could be important to consider. More specifically, although infection resolved, wounds were still colonized with bacteria and suggested that IV antibiotic therapy may not be sufficient to fully eradicate bacteria from a wound. Recurring infection can be a problem in wounds, and is a hallmark indicator of biofilm-related infection. There is a rule of thumb, specifically for planktonic bacteria, that at a concentration of $10^5$ CFU/g tissue, infection will develop. In this case, IV antibiotics reduced planktonic bacteria to less than $10^5$ CFU/g tissue, but in those wounds inoculated with well-established biofilms of *A. baumannii*, they were at concentrations greater than $10^5$ CFU/g (Tables 5 & 6). The data collected herein suggested that IV antibiotics may not fully eradicate biofilms of *A. baumannii* to an acceptable level. This could be an important consideration in wound management.

When CZ-1-179 was used in combination with IV antibiotics (Pig 4), bioburden was reduced completely within two weeks. *A. baumannii* was found at the endpoint in at least one wound treated with SSD/IV antibiotics. Although not tested directly, results indicated that CZ-1-179 did not adversely affect IV antibiotics, but rather improved outcomes.

TABLE 5

Microbiological results of wounds that were debrided regularly.

| Pig # | Wound Section | Bacterial Phenotype | Treatments | Last Day that A. baumannii was Detected in At Least One Wound by Culture Swab | Log$_{10}$ Transformed CFU/g Tissue at Necropsy (Day 28) |
|---|---|---|---|---|---|
| 1 | 1 | Planktonic | Positive controls | 28 | 0 |
|   | 2 | Biofilm | Positive controls | 28 | 5.8 ± 6.1 |
|   | 3 | N/A | Negative controls | 0 | 0 |
| 2 | 1 | Planktonic | CZ-1-179 | 5 | 0 |
|   | 2 | Biofilm | CZ-1-179 | 5 | 0 |
|   | 3 | Planktonic | SSD | 5 | 0 |
|   | 4 | Biofilm | SSD | 12 | 0 |
| 3 | 1 | Planktonic | Colistin/imipenem (IV) | 28 | 2.4 ± 2.7 |
|   | 2 | Biofilm | Colistin/imipenem (IV) | 28 | 2.5 ± 2.8 |
| 4 | 1 | Planktonic | CZ-1-179 + colistin/imipenem (IV) | 17 | 0 |
|   | 2 | Biofilm | CZ-1-179 + colistin/imipenem (IV) | 10 | 0 |
|   | 3 | Planktonic | SSD + colistin/imipenem (IV) | 7 | 0 |
|   | 4 | Biofilm | SSD + colistin/imipenem (IV) | 28 | 0 |

TABLE 6

Microbiological results of wounds that were undebrided.

| Pig # | Wound Section | Bacterial Phenotype | Treatments | Last Day that A. baumannii was Detected in At Least One Wound | Log$_{10}$ Transformed CFU/g Tissue at Necropsy (Day 28) |
|---|---|---|---|---|---|
| 1 | 1 | Planktonic | Positive controls | 28 | 4.5 ± 4.7 |
|   | 2 | Biofilm | Positive controls | 28 | 7.0 ± 7.3 |
|   | 3 | N/A | Negative controls | 0 | 0 |
| 2 | 1 | Planktonic | CZ-1-179 | 5 | 0 |
|   | 2 | Biofilm | CZ-1-179 | 5 | 0 |
|   | 3 | Planktonic | SSD | 5 | 0 |
|   | 4 | Biofilm | SSD | 5 | 0 |
| 3 | 1 | Planktonic | Colistin/imipenem (IV) | 28 | 2.5 ± 2.4 |
|   | 2 | Biofilm | Colistin/imipenem (IV) | 28 | 2.5 ± 2.7 |
| 4 | 1 | Planktonic | CZ-1-179 + colistin/imipenem (IV) | 15 | 0 |
|   | 2 | Biofilm | CZ-1-179 + colistin/imipenem (IV) | 15 | 0 |
|   | 3 | Planktonic | SSD + colistin/imipenem (IV) | 17 | 0 |
|   | 4 | Biofilm | SSD + colistin/imipenem (IV) | 17 | 0 |

While this invention has been described in some embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A triaryl polyamine compound selected from the group consisting of an $A^{1\text{-}6}$ ring

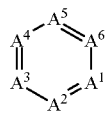

and a salt thereof;

wherein:
each $A^1$, $A^2$, $A^3$, $A^4$, $A^5$, and $A^6$ is independently selected from the group consisting of $CR^r$, $CR^a$, and $CR^b$;
wherein two of the $A^{1\text{-}6}$ ring members are each an independently selected $CR^r$;
each $R^r$ is an independently selected $A^{7\text{-}11}$ ring

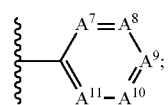

each $A^{7\text{-}11}$ ring member $A^7$, $A^8$, $A^9$, $A^{10}$, and $A^{11}$ is independently selected from the group consisting of $CR^a$ and $CR^b$;
wherein for each $R^r$, one $A^{7\text{-}11}$ ring member is an independently selected $CR^a$;

wherein the triaryl polyamine compound comprises two independently selected CR$^a$ or three independently selected CR$^a$;

each R$^a$ is an independently selected group of Formula III:

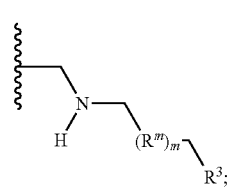

III each R$^m$ is a member independently selected from the group consisting of —CR$^{2a}$R$^{2b}$— and —C(R$^{2a}$)(R$^{2b}$)-L-C(R$^{2c}$)(R$^{2d}$)—;

each m is an integer independently selected from 1 to 3;

each L is a bond;

each R$^3$ is a member independently selected from the group consisting of —Z$^1$-R$^4$, —Z$^1$—Y$^1$-R$^4$, —Z$^1$—Y$^1$—Y$^2$-R$^4$, and —Z$^1$—Y$^1$-Y$^2$—Y$^3$-R$^4$;

each R$^4$ is a member independently selected from the group consisting of hydrogen, unsubstituted alkyl and alkyl substituted with fluoro, hydroxy, alkoxy, amino, alkylamino, acylamino or alkylthio;

each Y$^1$, Y$^2$, and Y$^3$ is an independently selected group of Formula IA:

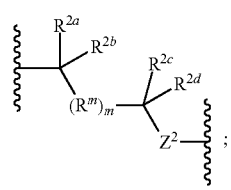

IA each R$^{2a}$, R$^{2b}$, R$^{2c}$, and R$^{2d}$ is a member independently selected from the group consisting of hydrogen, alkyl, and fluoroalkyl;

each Z$^1$ and Z$^2$ is —NH—; and each R$^b$ is a member independently selected from hydrogen, alkyl, hydroxyl, alkoxy, aryl, aryloxy, halo, fluoroalkyl, and fluoroalkyloxy.

2. The compound of claim 1, wherein each R$^4$ is alkyl.

3. The compound of claim 1, wherein:
each R$^m$ is —CR$^{2a}$R$^{2b}$—; and
each m is 3.

4. The compound of claim 1, wherein the compound is selected from the group consisting of

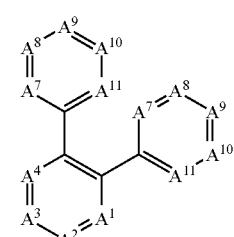

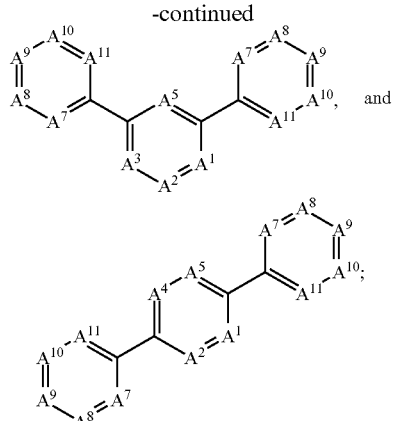

or a salt thereof wherein:
each A$^1$, A$^2$, A$^3$, A$^4$, and A$^5$ is independently selected from the group consisting of CR$^a$ and CR$^b$;

each A$^7$, A$^8$, A$^9$, A$^{10}$, and A$^{11}$ is independently selected from the group consisting of CR$^a$ and CR$^b$;

wherein for each A$^{7-11}$ ring, one A$^{7-11}$ ring member is an independently selected CR$^a$;

wherein the triaryl polyamine compound comprises two independently selected CR$^a$ or three independently selected CR$^a$;

each R$^a$ is an independently selected group of Formula III:

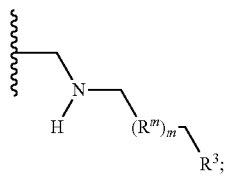

III each R$^m$ is —CH$_2$—;

each m is independently 1 or 2;

each R$^3$ is a member independently selected from the group consisting of —Z$^1$—R$^4$, —Z$^1$—Y$^1$-R$^4$, and —Z$^1$—Y$^1$-Y$^2$-R$^4$;

each R$^4$ is independently selected from the group consisting of n-butyl, isobutyl, 2-ethylbutyl, 2-methylbutyl, 3-methylbutyl, n-hexyl, isohexyl, and 2-ethylhexyl;

each Y$^1$ and Y$^2$ is an independently selected group of Formula IA:

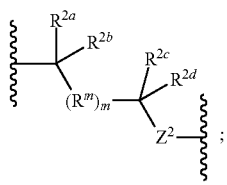

IA each R$^{2a}$, R$^{2b}$, R$^{2c}$, and R$^{2d}$ is hydrogen;

each Z$^1$ and Z$^2$ is —NH—; and each $R^b$ is a member independently selected from hydrogen, alkyl, hydroxyl, alkoxy, aryl, aryloxy, halo, fluoroalkyl, and fluoroalkyloxy.

5. The compound of claim 4, wherein the compound is

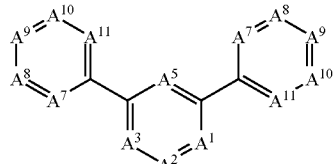

or a salt thereof
wherein:
the compound comprises two independently selected $CR^a$.

6. The compound of claim 4, wherein each $A^9$ is a $CR^a$.

7. The compound of claim 4, wherein $A^2$ is $CR^b$.

8. The compound of claim 7, wherein the $A^2$ $R^b$ is an alkyl selected from the group consisting of methyl, ethyl, n-propyl, isopropyl, n-butyl, iso-butyl, t-butyl, n-pentyl, and isopentyl.

9. The compound of claim 8, wherein the $A^2$ $R^b$ alkyl is t-butyl.

10. The compound of claim 4, wherein each $R^3$ is an independently selected $-Z^1-Y^1-R^4$.

11. The compound of claim 4, wherein:
each $R^a$ is $-CH_2[NH(CH_2)_n]_pNHR^4$;
each n is 3; and
each p is an integer independently selected from 1 to 3.

12. The compound of claim 4, wherein each $R^4$ is independently selected from the group consisting of n-butyl, isobutyl, 2-ethylbutyl, 2-methylbutyl, and 3-methylbutyl.

13. The compound of claim 4, wherein each $R^b$ is a member independently selected from the group consisting of hydrogen, alkyl, and hydroxyl.

14. The compound of claim 4, wherein each $R^b$ is a member independently selected from the group consisting of hydrogen and alkyl.

15. The compound of claim 4, wherein the compound is selected from the group consisting of

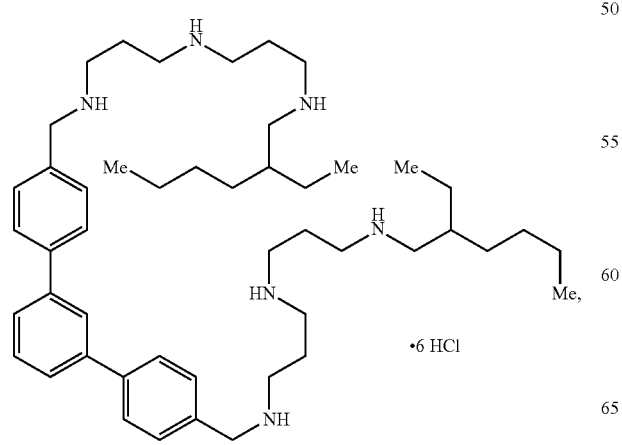

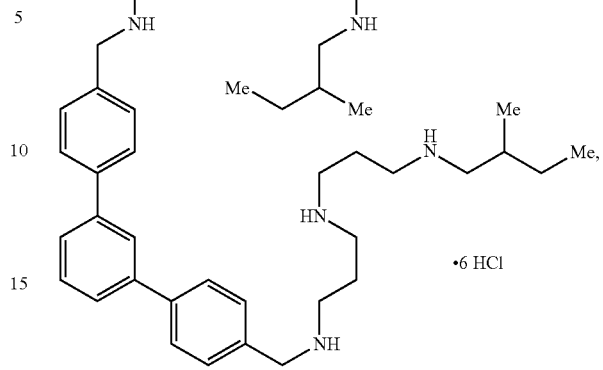

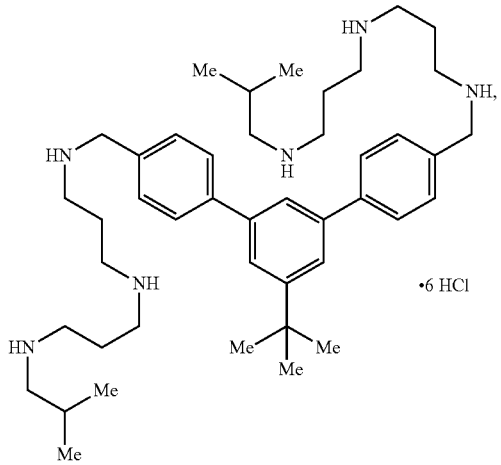

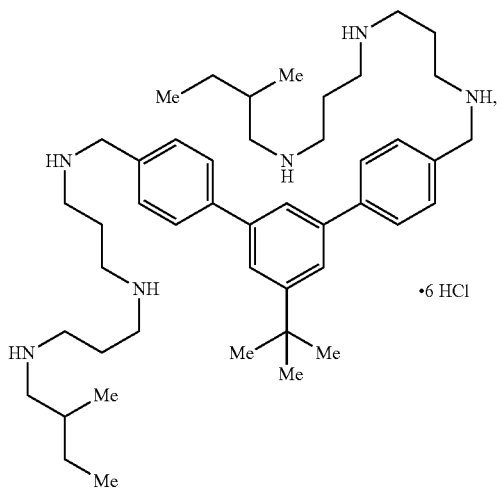

-continued

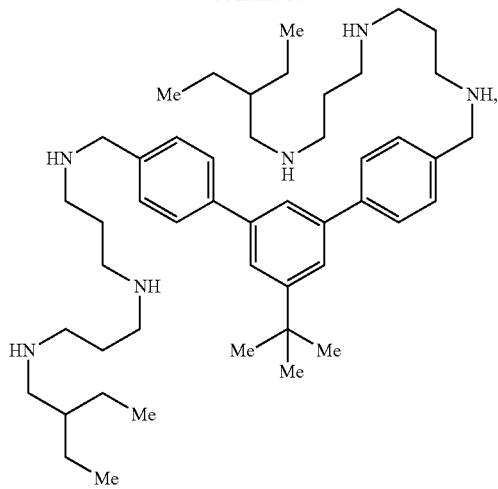

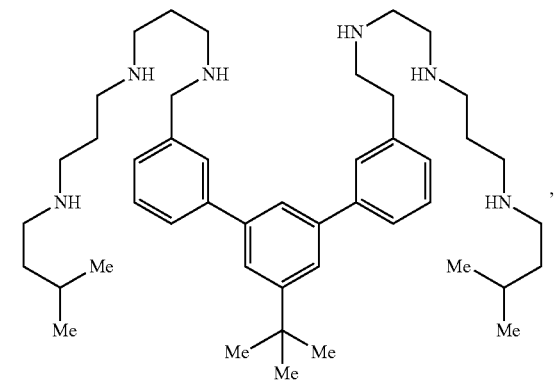

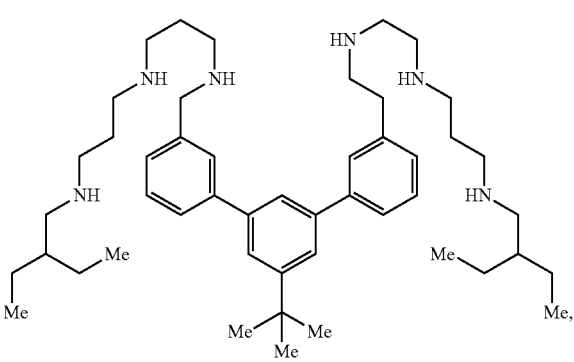

and a salt thereof.

16. The compound of claim 4, wherein the compound

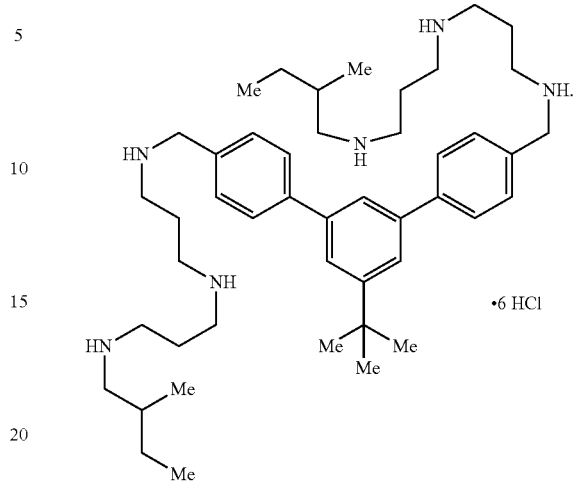

17. A method for inhibiting formation of a biofilm by inhibiting incorporation of planktonic bacteria, the method comprising a step of treating planktonic bacteria with the compound of claim 1, thereby inhibiting incorporation of the planktonic bacteria into the biofilm.

18. A method for enhancing wound healing, the method comprising a step of treating a patient with the compound of claim 1, thereby enhancing healing of a wound in the patient.

19. The method of claim 17, wherein the biofilm comprises an antibiotic-resistant bacterial species.

20. The compound of claim 1, wherein the compound is selected from the group consisting of

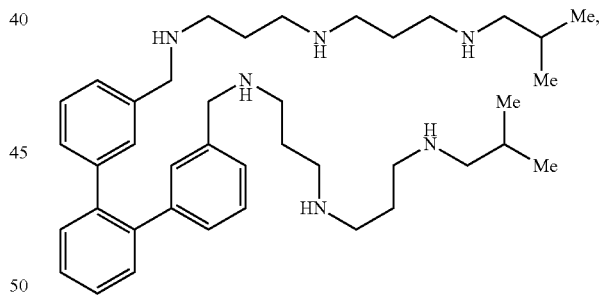

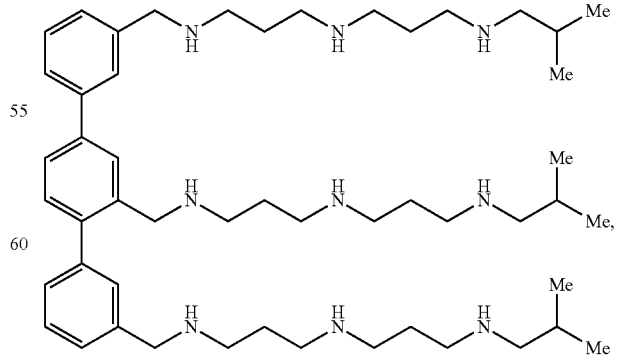

71
-continued
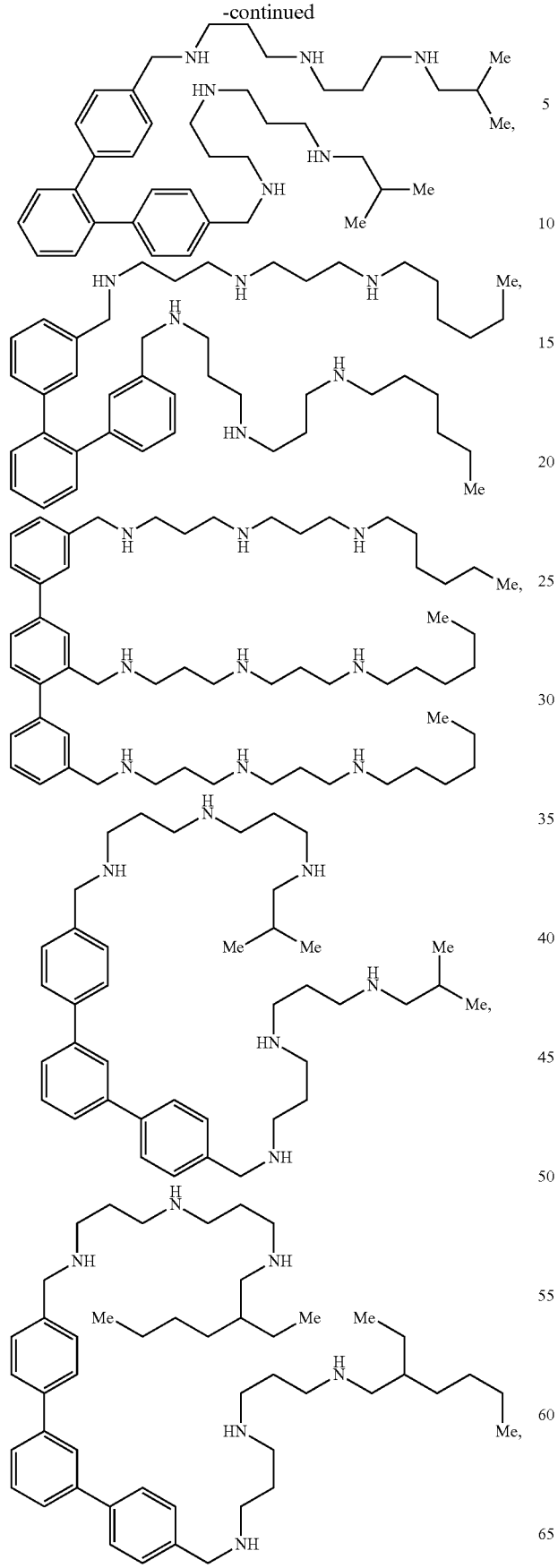
72
-continued
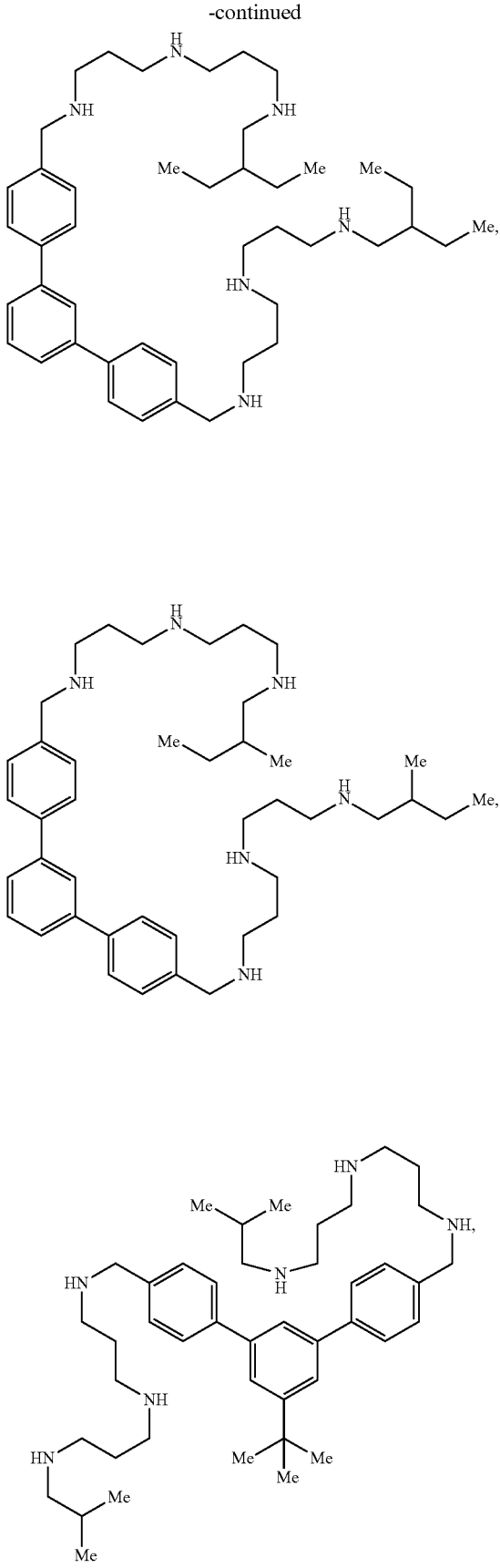

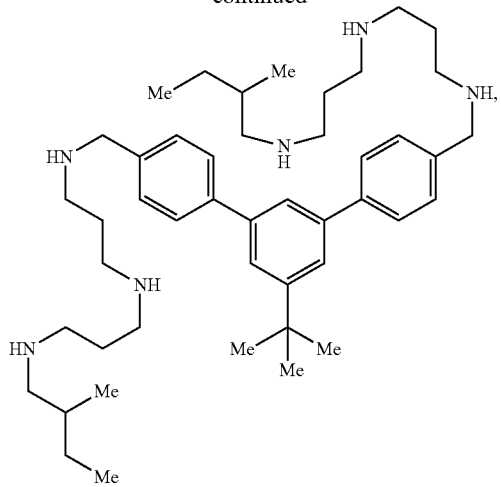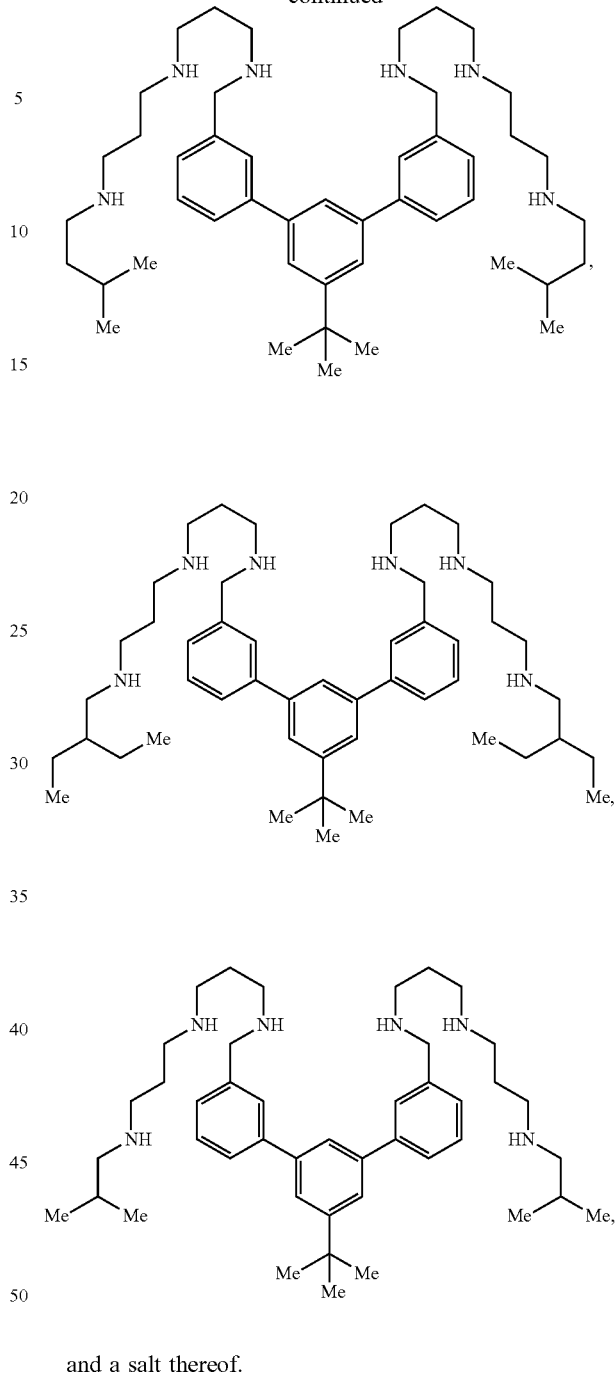
and a salt thereof.